United States Patent [19]
König et al.

[11] 3,974,142
[45] Aug. 10, 1976

[54] PENICILLINS

[75] Inventors: Hans-Bodo König; Wilfried Schröck; Karl-Georg Metzger, all of Wuppertal-Elberfeld, Germany

[73] Assignee: Bayer Aktiengesellschaft, Germany

[22] Filed: Sept. 3, 1974

[21] Appl. No.: 502,956

Related U.S. Application Data

[63] Continuation-in-part of Ser. Nos. 299,246, Oct. 20, 1972, abandoned, and Ser. No. 300,776, Oct. 20, 1972, abandoned.

[30] Foreign Application Priority Data

Oct. 23, 1971 Germany............................. 2152967
Oct. 23, 1971 Germany............................. 2152968

[52] U.S. Cl............................. 260/239.1; 424/271
[51] Int. Cl.$^2$......................................... C07D 499/46
[58] Field of Search............................. 260/239.1 A

[56] References Cited
UNITED STATES PATENTS

| | | | |
|---|---|---|---|
| 3,634,405 | 1/1972 | Holdrege | 260/239.1 A |
| 3,669,958 | 6/1972 | Holdrege | 260/239.1 A |

FOREIGN PATENTS OR APPLICATIONS

| | | | |
|---|---|---|---|
| 2,152,967 | 5/1973 | Germany | 260/239.1 A |
| 2,152,968 | 4/1973 | Germany | 260/239.1 A |

*Primary Examiner*—Alton D. Rollins
*Assistant Examiner*—D. B. Springer

[57] ABSTRACT

Arylmethyl- and cyclohexenylmethyl- penicillins, substituted on the $\alpha$-carbon atom of the side chain by a 2,3-disubstituted imidazolidinylcarbamido or a 2,3-disubstituted imidazolidinylthiocarbamido group, or by the corresponding 2,3-disubstituted 1,3-diazacyclohexylcarbamido or thiocarbamido groups are antibacterial agents.

85 Claims, No Drawings

PENICILLINS

CROSS REFERENCE

This is a continuation-in-part of our copending applications Ser. Nos. 299,264 and 300,776, each of which was filed Oct. 20, 1972 and each of which is now abandoned.

DETAILED DESCRIPTION

The present invention relates to new penicillin compounds, to processes for their production, to pharmaceutically acceptable compositions wherein such penicillins are the active agent, and to their use in human and veterinary medicine, as therapeutic agents in poultry and mammals, and as feedstuff additives and as growth-promoting agents in animals.

The new penicillins are valuable as therapeutic agents in poultry and mammals, and in man, in the treatment of infectious diseases caused by Gram-positive and Gram-negative bacteria and especially of those caused by bacteria from the group of the enterobacteria and pseudomonades. The penicillins of the present invention can be administered orally and parenterally.

Antibacterial agents, such as ampicillin (U.S. Pat. No. 2,985,648) have proved very effective in the treatment of infections caused by Gram-positive and Gram-negative bacteria. However, they are not able to combat infections which are caused, for example, by bacteria of the group of *Klebsiella-Aerobacter* or by indole-positive strains of Proteus.

Carbenicillin (U.S. Pat. Nos. 3,142,673 and 3,282,926) is only effective in man in the case of infections caused by *Klebsiella-Aerobacter* if administered in a continuous high dosage, such as is only achieved by infusion.

The penicillins of the present invention may be regarded as methylpenicillins which are substituted in the methyl group by a moiety B and an acyl-biureido moiety of which the carbonyl group in the acyl group can be replaced by a —SO$_2$— group:

$$\text{Acyl}-\overset{5}{\text{N}}-\overset{4}{\underset{\text{E}}{\text{C}}}-\overset{3}{\text{N}}-\overset{2}{\underset{\text{O(S)}}{\text{C}}}-\overset{1}{\text{N}}- \quad (\text{E is: }=\text{O}, =\text{S or }=\text{N}-)$$

6-($\alpha$-Biureido)-acetamido-penicillanic acids are described in U.S. Pat. No. 3,483,188 and in German Offenlegungsschrift No. 1,959,920, but none of the 6-($\alpha$-biureido)-acetamido-penicillanic acids described and claimed in these patents possesses an acyl radical on the nitrogen atom of the biureido radical which is located in the 5-position.

The present invention comprises new penicillins of the formula $$\text{A}-\text{Z}-\text{NH}-\overset{*}{\underset{\text{B}}{\text{CH}}}-\text{CO}-\text{NH}-\text{CH}-\text{CH} \begin{array}{c} \diagup \text{S} \diagdown \\ \phantom{x} \\ \diagdown \text{N} \diagup \end{array} \begin{array}{c} \diagup \text{CH}_3 \\ \text{C} \\ \diagdown \text{CH}_3 \end{array}$$

(with C=O and CH-COOH on the β-lactam ring)

or pharmaceutically acceptable non-toxic salts thereof, wherein

C is a carbon atom constituting a center of chirality;

A is a moiety of the formula $$N\equiv C-N\diagup\underset{Q_1}{\overset{Y}{\diagdown}}\diagdown N-, \quad N\equiv C-\underset{R_2}{N}-Y-\underset{R_3}{N}-,$$

$$R_1-X-N\diagup\underset{Q_1}{\overset{Y}{\diagdown}}\diagdown N-, \quad R_1-X-\underset{R_2}{N}-Y-\underset{R_3}{N}-,$$

$$R_1-\underset{\underset{Q_1}{N}}{\overset{Y}{\underset{\|}{C}}}-N-Y-\underset{R_3}{N}-, \quad R_1-X-\underset{Q_1}{N}-\overset{Y}{\underset{\|}{C}}-\underset{R_3}{N}-,$$

$$R_1-X-\underset{R_2}{N}-\overset{Y}{\underset{\|}{C}}-\underset{\underset{Q_1}{N}}{N}-, \quad X-\underset{Q_2}{\diagdown}N-Y-\underset{R_3}{N}-,$$

$$G-N\diagup\underset{X\diagdown Q_1}{\overset{Y}{\diagdown}}\diagdown N- \quad \text{or} \quad R_1-\overset{R_2}{\underset{\|}{C}}-N-Y-N-;\\ \phantom{xxxxxxxxxxxxx}N--C\diagup\\ \phantom{xxxxxxxxxxxxxxxx}G\phantom{x}G$$

wherein

X is $-\overset{O}{\underset{O}{\overset{\|}{\underset{\|}{S}}}}-,\ -\overset{O}{\overset{\|}{C}}-\text{or}\ -\overset{S}{\overset{\|}{C}}-;$ Y is $-\overset{O}{\overset{\|}{C}}-,\ -\overset{S}{\overset{\|}{C}}-,\ -\overset{NH}{\overset{\|}{C}}-,\ -\overset{N-R}{\overset{\|}{C}}-,$ $-\overset{N-Aryl}{\overset{\|}{C}}-,\ -\overset{N-SO_2-R}{\overset{\|}{C}}-$ or $-\overset{N-SO_2-Aryl}{\overset{\|}{C}}-$ wherein Aryl is an aryl moiety;

Z is $-\overset{O}{\overset{\|}{C}}-$ or $-\overset{S}{\overset{\|}{C}}-;$ $Q_1$ is $-(\overset{G}{\underset{G}{C}})_{2\ or\ 3}-,\ -\overset{G}{\underset{G}{C}}-CO-\overset{G}{\underset{G}{C}}-,\ -\overset{G}{\underset{G}{C}}-O-\overset{G}{\underset{G}{C}}-,$ $-\overset{G}{\underset{G}{C}}-\overset{G}{\underset{R}{N}}-\overset{G}{\underset{G}{C}}-,\ -(\overset{G}{\underset{G}{C}})_{0\ or\ 1}-\overset{G}{\underset{G}{C}}=\overset{G}{\underset{G}{C}}-$ or (phenyl ring) $\overset{G}{\underset{G}{\overset{\|}{C}}}$ or 1 ;

$Q_2$ is $-(\overset{G}{\underset{G}{C}})_{3\ or\ 4}-,\ -\overset{G}{\underset{G}{C}}-O-\overset{G}{\underset{G}{C}}-,\ -\overset{G}{\underset{G}{C}}-\overset{G}{\underset{R}{N}}-\overset{G}{\underset{G}{C}}-,$ $\leftarrow NH-(\overset{G}{\underset{G}{C}})_2-,\ \leftarrow N-(\overset{G}{\underset{R}{C}})_2-,\ -\overset{G}{\underset{G}{C}}-CO-\overset{G}{\underset{G}{C}}-,$

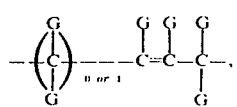

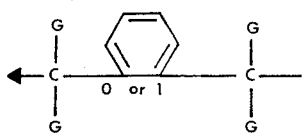

or

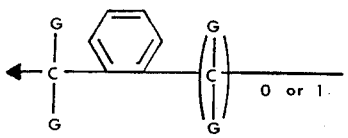

R is straight-chain or branched alkyl of 1 to 5 carbon atoms;

R₁ is alkyl preferably of 1 to 10 carbon atoms and especially lower alkyl, cycloalkyl preferably of 3 to 10 carbon atoms, alkenyl preferably of 2 to 10 carbon atoms, cycloalkenyl preferably of 3 to 10 carbon atoms, vinyl, arylvinyl, mono-, di- or tri-halo-lower alkyl, H₂N—, R—NH—, (R)₂N—, aryl-NH—, aryl-lower alkylamino, alkoxy preferably of 1 to 8 carbon atoms and especially lower alkoxy, aralkoxy preferably of 1 to 8 carbon atoms in the alkoxy portion, cycloalkoxy preferably of 3 to 7 carbon atoms, aryloxy preferably of 6 carbon atoms, R—O—V, R—S—V, N≡C—V—, R—O—CO—V—, H₂N—CO—V—, R—N-H—CO—V—, R—O—CO—NH—; R—SO₂NH—, (R)₂N—CO—V— wherein R is as above defined,

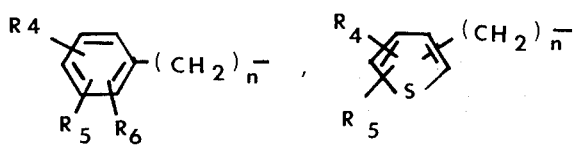

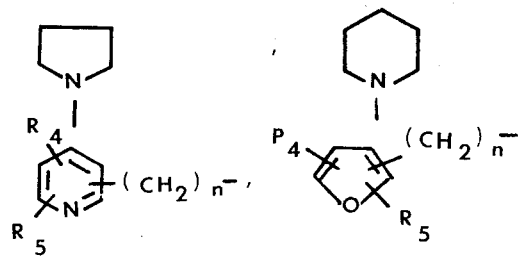

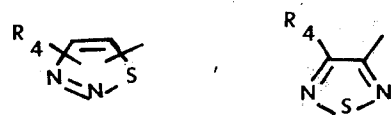

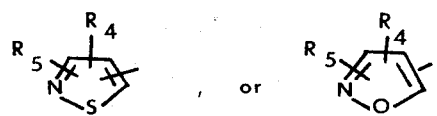

provided that when X is —SO₂—, R₁ is not alkoxy, aralkoxy, cycloalkoxy or aryloxy, and further provided that R₁ can also be hydrogen when X is —CO—;

V is a divalent organic radical of 1 to 3 carbon atoms;

n is 0, 1 or 2;

R₂ and R₃ are the same or different and are each hydrogen, alkyl preferably of 1 to 8 carbon atoms and especially lower alkyl, alkenyl preferably of 2 to 8 carbon atoms, vinyl, allyl, propenyl, cycloalkyl preferably of 3 to 6 carbon atoms, cycloalkenyl preferably of 3 to 6 carbon atoms, mono-, di- or tri-halo-lower alkyl or aryl;

R₄, R₅ and R₆ are the same or different and are each hydrogen, nitro, cyano, (R)₂N— (R)₂N—CO, R—CO—NH— R—O—CO—, R—CO—O—, R—, R—O—, wherein R is as above defined, H₂N—SO₂—, chlorine, bromine, iodine, fluorine, or trifluoromethyl;

G is hydrogen or straight- or branched-chain alkyl, preferably of 1 to 5 carbon atoms;

B is a moiety of the formula

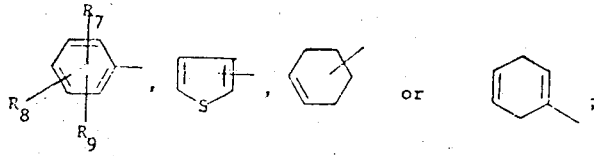

wherein

R₇, R₈ and R₉ are the same or different and are each hydrogen, halogen, nitro, hydroxy, R—, R—O—, R—S—, R—SO—, R—SO₂—, (R)₂N—, R—CO—NH—, or R—CO—O—, wherein R is as above defined.

The terms "lower alkyl" and "lower alkoxy" are intended to be understood in the present specification as meaning a straight-chain or branched-chain alkyl or alkoxy group of 1 to 6 carbon atoms. In connection with other groups, such as "di-lower alkylamino", the term "lower alkyl" only refers to the alkyl part of the group in question.

The arrow in the divalent linking group ↖O₂ means that the linkage of two atoms by the two free valencies of this group must take place as indicated by the arrow.

The present invention includes within its scope penicillins as defined above in which the chirality center C* is either the R- or the S- configuration, as well as mixtures of the diastereomers resulting from the two possible configurations.

According to one preferred embodiment of the present invention,

A is

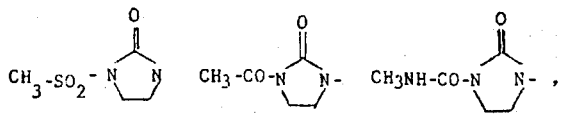

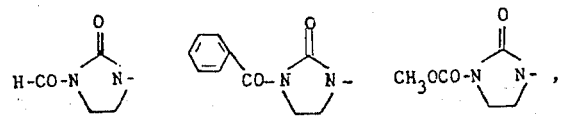

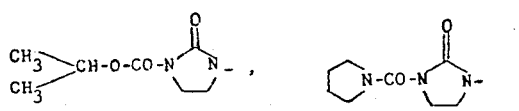

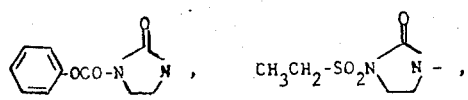

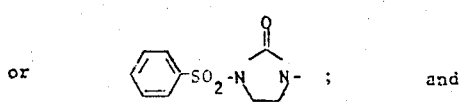

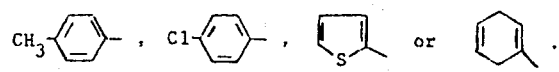

or 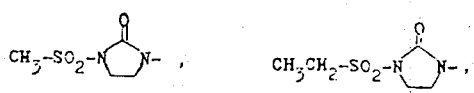 ; and

B is phenyl,

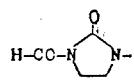 , 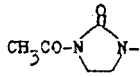 , 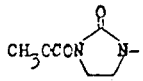 or 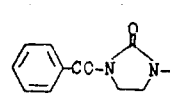 .

The chirality center C* is preferably in the R- configuration.

According to another preferred embodiment of the present invention,

A is

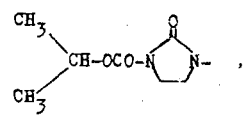

or $H_2NCC-N\underset{\smile}{\phantom{N}}N-$ ; and

B is phenyl, p-nitrophenyl, p-methylphenyl, p-chlorophenyl, p-hydroxyphenyl, thienyl-(2),

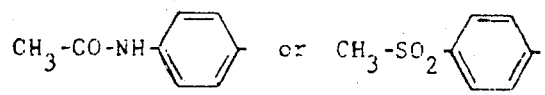

When the penicillins of the present invention are in the form of a pharmaceutically acceptable non-toxic salt, the preferred salts are formed at the carboxylic group and include sodium, potassium, magnesium, calcium, aluminum and ammonium salts, and substituted ammonium salts with amines, such as di- and tri-lower alkylamines, procaine, dibenzylamine, N,N'-dibenzylethylene-diamine, N-benzyl-β-phenylethylamine, N-methyl- and N-ethyl-morpholine, 1-ephenamine, dehydroabietylamine, N,N'-bis-dehydroabietylethylenediamine, and N-lower alkylpiperidine.

The alkali metal salts are particularly preferred, especially the sodium and potassium salts.

The present invention further provides a process for the production of the penicillins of formula I wherein a 6-amino-penicillanic acid derivative of the formula:

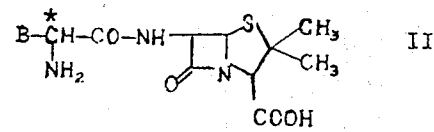

or a product of the condensation of such a derivative with a carbonyl compound, such product having the formula:

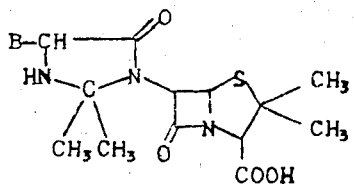

or a silyl or disilyl derivative of such derivative, of the formula:

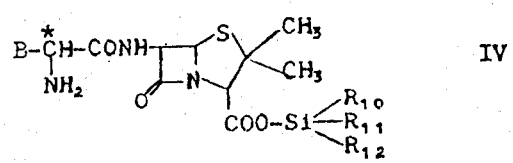

or

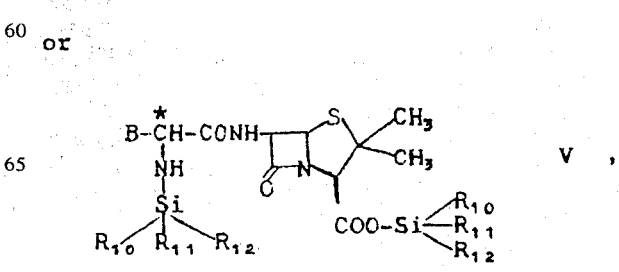

respectively, is reacted with a compound of the formula:

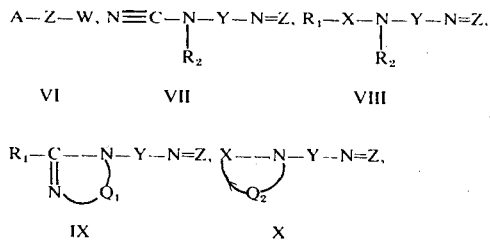

wherein $R_{10}$, $R_{11}$ and $R_{12}$ are the same or different and are each alkyl of 1 to 6 carbon atoms; A, B, C*, G, $Q_1$, $Q_2$, $R_1$, $R_2$, X, Y and Z are as above defined; and W is halogen, azide or

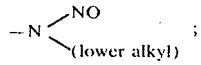

in an anhydrous or aqueous solvent in the presence of a base, when a compound of the Formula II or III is reacted, or in an anhydrous solvent free of hydroxyl groups, with or without a base, when a compound of the formula IV or V is reacted, at a temperature of −50° to +50° C.

The carbonyl compound may, for example, be acetone (see U.S. Pat. No. 3,198,804).

If a compound of the formula II or III is used as the starting material for the synthesis of the penicillins according to the present invention, and is reacted with a compound of the formula VI, VII, VIII, IX or X, the reaction can be carried out, for example, in a mixture of water and an organic solvent which is miscible with water, such as acetone, tetrahydrofuran, dioxane, acetonitrile, dimethylformamide, dimethylsulphoxide or isopropanol. During the reaction, the pH of the reacting mixture is preferably kept at between 2.0 and 9.0 by addition of a base or the use of a buffer solution. The reaction according to the invention is however preferably carried out at a pH of between 4.5 and 9.0 or between 2.0 and 3.0. It is also possible to carry out the reaction in a water-immiscible solvent, for example in chloroform or methylene chloride, with the addition of, preferably, triethylamine, diethylamine or N-ethylpiperidine. The reaction can further be carried out in a mixture of water and a water-immiscible solvent, such as ether, chloroform, methylene chloride, carbon disulphide, isobutyl methyl ketone, ethyl acetate or benzene, when it is preferred to stir the mixture vigorously and to keep the pH at between 4.5 and 9.0 or 2.0 and 3.0, by adding a base or using a buffer solution.

If a compound of the formula IV or V is used as the starting material for the process of the invention and is reacted with a compound of the formula VI, VII, VIII, IX or X, the reaction must be carried out in an anhydrous solvent free of hydroxyl groups. Examples of suitable solvents are methylene chloride, chloroform, benzene, tetrahydrofurane, acetone and dimethylformamide. The addition of a base is not necessary, but it can in some cases improve the yield and purity of the products. The base, if added, should generally be either a tertiary amine, such as pyridine or triethylamine, or a secondary amine which as a result of steric hindrance is difficult to acylate, such as dicyclohexylamine. The available choice of usable bases is therefore very wide.

As with most chemical reactions, higher or lower temperatures than those indicated in the Examples can be used. However, if the parameters given in the Examples are significantly exceeded, side-reactions will increasingly take place, which reduce the yield or adversely influence the purity of the products. On the other hand, excessively lowered reaction temperatures reduce the speed of reaction so greatly that reductions in yield can arise. Reaction temperatures in the range of −20° C to +50° C are therefore preferred, a temperature of 0° C to + 20° C being particularly preferred.

The reactants can be reacted with one another in equimolecular amounts. It may however be advisable to use one of the two reactants in excess in order to facilitate the purification, or pure preparation, of the desired penicillin and to increase the yield. For example, the reactants of the formula II or III can be employed in an excess of 0.1 to 0.3 mol equivalent and as a result a smaller degree of decomposition of the reactants of the formula VI, VII, VIII, IX or X in the aqueous solvent mixture can be achieved. The excess of the reactants of the formula II or III can easily be removed, because of their good solubility in aqueous mineral acid, when working up the reaction mixture. On the other hand however, it is also possible with advantage to employ the reactants of the formula VI, VII, VIII, IX or X in an excess of, for example, 0.1 to 1.0 mol equivalent. By doing this, the reactants, for example, of the formula II or III, are more economically used and the decomposition of the reactants of the formula VI, VII, VIII, IX or X, which takes place as a side reaction in aqueous solvents, is compensated. Since the compounds of the formula VI, VII, VIII, IX or X added in excess are rapidly converted, in water, into neutral compounds, which can easily be removed, the purity of the penicillins is thereby hardly impaired.

The amount of the bases used is determined, for example, by the desired maintenance of a particular pH. Where pH measurement and adjustment is not carried out, or is not possible or meaningful because of the absence of sufficient amounts of water in the diluent, 2 mol equivalents of base are preferably added with the compounds of the formula II or III are used, while either no base at all, or, preferably, 1 mol equivalent of base is added when the compounds of the formula IV or V are used.

The working up of the reaction batches for the manufacture of the penicillins according to the present invention, and of their salts, can throughout be effected in the manner generally known for penicillins.

The free penicillins of the formula I and their salts can be interconverted in any suitable manner; methods for such interconversion are known.

The compounds of the formula II used as starting materials in the process according to the present invention can, as regards the configuration of the asymmetric center in the side chain (C*) occur in the D(−) = R-form or L(+) = S-form. They are described in German Patent Specification No. 1,156,078, in U.S. Pat. Nos. 3,342,677, 3,157,640, 2,985,648 and 3,140,282, in South African Pat. No. 6S/P290 and (an anhydrous form) in U.S. Pat. No. 3,144,445. All crystal forms and configurations of the compound of the formula II are suitable as the starting material for the reaction according to the invention. The compounds of the formula III, IV or V used as the starting materials in the process according to the present invention can, as regards the configuration at the asymmetric center in the side chain (C*), also occur in the D(−) = R− form or L(+) = S-form. The configuration of the asymmetric centers of the 6-amino-penicillanic acid nucleus in the compounds of the formula II, III, IV and V should be identical with the corresponding asymmetric centers of 6-amino-penicillanic acid which has been obtained, for example, from penicillin-G by a fermentative process.

The preparation of the compounds of the formula IV and V used as the starting material is described in Netherlands Pat. No. 68/16,057.

The preparation of the compounds of the formula VI, VII, VIII, IX or X used as the starting material in the present invention is illustrated in more detail in examples.

The penicillins according to the present invention are also produced by the process of:

i. producing a reactive intermediate by reacting a carboxylic acid of the formula XI, a carboxylic acid salt of the formula XIa, or a carboxylic acid silyl or hemisilyl ester of the formula XIb or XIc:

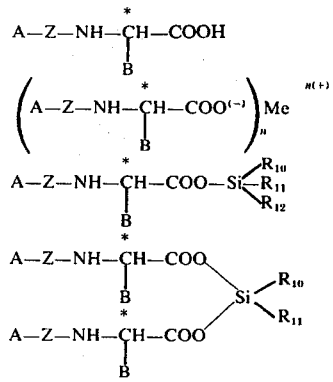

in an aqueous or anhydrous organic solvent when a compound of the formula XI or XIa is reacted, or in an anhydrous inert organic solvent free of hydroxy groups when a compound of formula XIb or XIc is reacted, at −70° C to +30° C, with either:

a. a compound of one of the formulae XII to XV

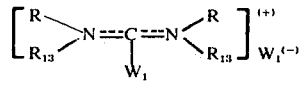

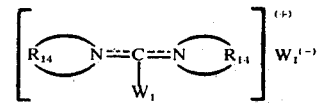

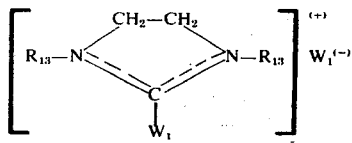

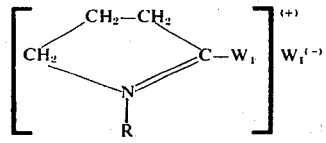

or b. with a reaction product produced by the reaction of compound of the formula:

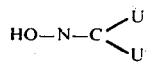

with about 1 mol equivalent of thionyl chloride in an inert anhydrous organic solvent in the presence of at least one mol equivalent of an organic base acting as an acid-acceptor at a temperature within the range −40° C to +25° C; the reaction product being reacted without prior isolation in the presence of a further mol equivalent of a base, with about 1 mol equivalent of the carboxylic acid of the formula XI or in the presence of 0–1 mol equivalent of a base, with about 1 mol equivalent of a compound of the formula XIa, XIb or XIc, at a temperature of −40° C to +30° C, whereby the reactive intermediate produced is of the formula:

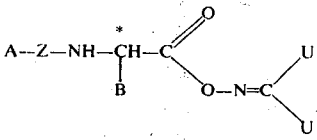

c. [only to be used with carboxylic acids of the formula XI] with about 1 mol equivalent of a carbodiimide in a diluent and in the presence of about 1 mol equivalent of a compound of the formula XVI whereby the reactive intermediate produced is of the formula:

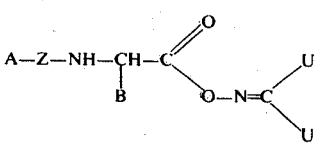

the diluent being anhydrous and free of hydroxy groups if a compound of the formula XVIII or XIX is to be used in step (ii);
and ii. reacting the reactive intermediate with 6-aminopenicillanic acid of formula XVIII or silyl- or di-silyl-6-aminopenicillanic acid of the formula XIX or XX.

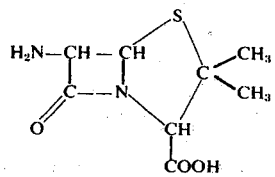

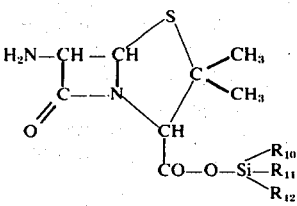

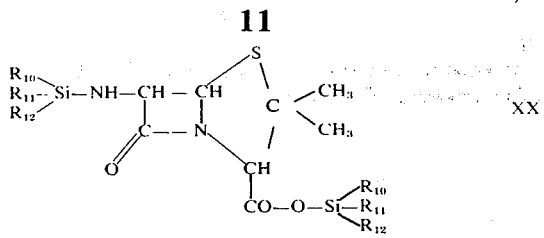

in a solvent in the presence of a base when 6-aminopenicillanic acid is used, or in an anhydrous solvent free of hydroxy groups when a compound of formula XIX or XX is used, at a temperature in the range of −70° C to +50° C, to produce the desired penicillin compound of the present invention; wherein A, B, C*, R and Z are as above defined;

$Me^{n(+)}$ is a cation of an n-valent alkali metal or alkaline earth metal or an aluminum cation;

$R_{10}$, $R_{11}$ and $R_{12}$ are as above defined;

$R_{13}$ is straight- or branched-chain alkyl of 1 to 5 carbon atoms or phenyl;

$R_{14}$ is $-(CH_2)_4-$, $-(CH_2)_5-$, or $-(CH_2-)_2-O-(CH_2)_2-$;

U which can be the same or different and is $-O \equiv N-$ or $-CO-O-$(lower alkyl); and $W_1$ is a halogen atom.

In step (i)(a), the reaction by which the reactive intermediate is produced is preferably carried out at −50° C to 0° C. Here, and for the subsequent reaction with the compounds of formula XVIII, XIX or XX, it can be of advantage if this reaction is allowed to take place in the presence of about one mol equivalent of an N-hydroxy compound of the formula:

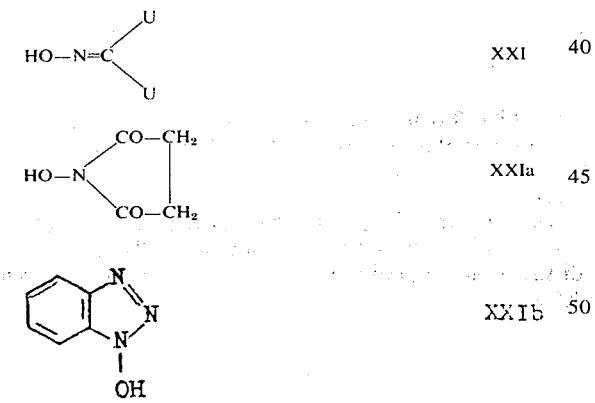

wherein U is as above defined.

The reaction may be carried out in the presence or absence of a base.

When optical activity is present at the chirality center C*, a possible racemization at this position can be prevented by using no organic bases, or relatively weak organic bases, for example, N-methylmorpholine, N-ethylmorpholine, N,N-dimethylaniline, pyridine or a weak inorganic base or a buffer, in step (i)(a), (b) and step (ii).

The reactive intermediate produced in step (i) is in all cases, a carboxylic acid of formula XI modified at the carboxyl group.

The reaction in step (ii) is preferably carried out at −50° C to 0° C. It is also preferably carried out in an aqueous solvent at a pH within the range 2–9, more preferably within the range 2–3 or 6.5–8.5, when 6-aminopenicillanic acid is used.

In the production, according to the invention, of the reactive intermediate by step (i)(a), from the carboxylic acid of formula XI or its salt of the formula XIa and the compound of the formulae XII, XIII, XIV or XV, anhydrous inert solvents or mixtures of these solvents, such as tetrahydrofurane, dioxane, dichloromethane, chloroform, ether, benzene, acetone, acetonitrile, dimethylformamide or hexamethylphosphoric acid triamide are preferably used. However, water or alcohols such as isopropanol or tert.-butanol can be present if the amounts are not excessive. However, if in this reaction the starting compounds are the silyl compounds XIb and XIc preferably only those organic solvents are used which contain neither −NH nor −OH groups, for example, dichloromethane, chloroform, tetrahydrofurane, dioxane, diethyl ether, acetonitrile, benzene, acetone and dimethylformamide.

If, in the reaction in step (i)(a) according to the invention between the carboxylic acid of the formula XI, the salt of the formula XIa or a silyl compound of the formula XIb or XIc with the compound of the formula XII, XIII, XIV or XV bases are added, practically all bases are suitable for this purpose provided they are sufficiently inert towards acylating agents and provided that when the silyl compounds Vb or Vc are used, they contain no O−H groups, preferably no O−H or N−H groups.

The reactants in the reaction step (i)(a) are preferably reacted with one another in equimolecular amounts. However, it can have a considerable influence on the purity of the products or on the yield if one of the two reactants is used in a more or less large excess.

When converting the carboxylic acids of the formula V into the reactive intermediate by any of steps (i)(a), (b) and (c), it is advisable to work at as low a temperature as possible if optical activity present at the chirality center C* is to be protected against racemization. Temperatures of −40° to −70° C are preferred. For the same reasons it is advantageous if the reaction time for converting the carboxylic acids of the formula XI into the forms modified at the carboxyl group is kept as short as possible. It can be advisable to maintain conversion times of only one minute or a few minutes.

The reaction of step (i)(a) when carried out in the presence of an N-hydroxy compound of the formula XVI, XVIa or XVIb can be carried out in exactly the same way as explained above for step (i)(a) except that about one mol equivalent of the N-hydroxy compound is added per mol of the compound of the formula XI, XIa, XIb or XIc.

When the reactive intermediate is produced by the method of step (i)(b), the starting material is an N-hydroxy compound of the formula XVI which is converted, in a solvent such as acetone, tetrahydrofurane, dioxane, dichloromethane, chloroform, benzene, ethyl acetate, diethyl ether or dimethyl formamide, in the presence of at least one mol equivalent of an organic base, such as triethylamine, pyridine, quinoline, N-methylmorpholine or N,N-dimethylaniline, into a reaction product of (at present) unknown constitution, by reaction with about one mol equivalent of thionyl chloride, at a temperature of −40° C. to +25° C. This reaction product is reacted without isolation in the presence of a further mol equivalent of a base, which may be one of those just mentioned, and preferably in the same amount, with one equivalent of the carboxylic acid XI, or, without further addition of any base or with up to one mol equivalent of the bases, with one mol equivalent of the salt XI$a$ or the silyl compound XI$b$ or XI$c$, at a temperature of −40° C to +30° C. The reactive intermediate of the formula XVII can then, optionally after removal of the hydrochloride of the base which has been produced during the reaction and has separated out, be isolated by evaporation of the solvent. It may also, if desired, be purified by crystallization from an inert solvent, or, if not crystalline, by brief washing with a solution, for example in ether or benzene, with an aqueous sodium bicarbonate solution at as low a temperature as possible.

Finally, the reactive intermediate may be produced, according to step (i)(c) of the process of the invention, by reacting the carboxylic acid of the formula XI, in the presence of an N-hydroxy compound of the formula XVI, with a carbodiimide. Suitable carbodiimides include, for example, dicyclohexylcarbodiimide, diisopropylcarbodiimide and N-ethyl-N'-3-dimethylaminopropylcarbodiimide. They are generally used in an aqueous solvent or solvent mixture, which can contain, for example, acetone, tetrahydrofurane, dioxane, acetonitrole, dimethylformamide, hexamethylphosphoric acid triamide, tertiary-butanol, isopropanol or formic acid methyl ester, or in an ahydrou solvent or solvent mixture which in addition to anhydrous solvent mentioned can also contain dichloromethane, chloroform, ethyl-acetate, ether, benzene, toluene or tetrachloromethane.

In the reaction in step (ii), according to the invention, of 6-aminopenicillanic acid (formula XVII) with the reactive intermediate, the 6-aminopenicillanic acid is preferably employed as a solution of its salt with an acid or a base. Suitable solvents for this purpose are, for example, water or a mixture of water and one or more water-miscible organic solvents, such as tetrahydrofurane, dioxane, acetonitrile, isopropanol, acetone, dimethylformamide, dimethylsulphoxide and hexamethylphosphoric acid triamide. Suitable salt-forming acids are, for example, hydrochloric acid, sulphuric acid and phosphoric acid. In order to convert the 6-aminopenicillanic acid into the salt of a base, dissolved in one of the above-mentioned solvents, it is possible to use, as bases suitable for the purpose, for example, inorganic bases such as sodium carbonate, sodium hydroxide and sodium bicarbonate, the corresponding potassium and calcium compounds, calcium oxide, magnesium oxide, magnesium carbonate or buffer mixtures, and organic bases such as N-methylmorpholine, N-ethylpiperidine, N,N-dimethylaniline, pyridine and triethylamine. Chloroform or dichloromethane are particularly suitable as solvents for a solution of 6-aminopenicillanic acid in an anhydrous medium while, for example, triethylamine, diethylamine, N-ethylpiperidine, N-ethylmorpholine and pyridine are suitable as the base for salt formation. The salts of 6-aminopenicillanic acid need not be dissolved completely in the reaction, according to the invention, with the reactive intermediate, but can also be present partly dissolved and partly in suspension.

Preferred solvents for the reaction between the silyl compounds of 6-aminopenicillanic acid, of the formula XVIII or XIX, and the reactive intermediate, are those which are inert towards silanyl radicals located on nitrogen and oxygen. Of these solvents, those preferred are organic solvents which are free of —NH groups as well as hydroxy groups, for example, tetrahydrofurane, dioxane, diethyl ether, acetonitrile, benzene, tetrachloromethane, chloroform, dichloromethane, dimethylformamide and acetone. If, in this reaction according to the invention between the silyl derivative XVIII or XIX of 6-aminopenicillanic acid and the reactive intermediate, bases are added, these bases are preferably bases containing neither —NH nor —OH groups.

In general, the reaction of step (ii) according to the invention between the reactive intermediate and 6-aminopenicillanic acid or its silyl derivative XVIII or XIX is carried out using equimolecular amounts of the reactants. It can, however, be desirable to use one of the two reactants in excess in order to facilitate the purification or pure preparation of the desired penicillin compound and to increase the yield. Thus, for example, 6-aminopenicillanic acid or the compound of the formula XVIII or XIX can be employed in an excess of 0.1 to 0.4 mol equivalent and better utilization of the carboxylic acids of the general formula V, modified at the carboxyl group, can thereby be achieved. During working up of the reaction mixture and isolation of the penicillin compound, any 6-aminopenicillanic acid present can easily be removed because of its good solubility in aqueous mineral acids. On the other hand, any carboxylic acid of the formula XI present is more difficult to separate from the penicillin formed.

The amount of the base added during the reaction of step (ii), according to the invention, of the reactive intermediate, with the 6-aminopenicillanic acid or the compound of the formula XVIII or XIX is determined, for example, by the desired maintenance of a particular pH value. Where a pH measurement and adjustment is not carried out or is not possible or meaningful because of the absence of sufficient amounts of water in the diluent, up to 2.0 mol equivalents of base are generally added when a compound of the formula XVIII or XIX is used, if a base is added at all, while 1.5 to 2.5 mol equivalents of base are generally added when 6-aminopenicillanic acid and an anhydrous reaction medium are used. The amount of the acid added during the reaction in step (ii) according to the invention is also determined, for example, by the desired maintenance of a particular pH or pH range. In general it is advantageous to carry out the said reaction between the reactive intermediate and 6-aminopenicillanic acid or its silyl derivative of the formula XVIII or XIX at temperatures which are as low as possible. As a result, purer products can be obtained, the yields can be improved and optical activity present at the chirality center C* can be protected against racemization. However, limits are here imposed by the possibilities not only of the solubility of the reactants being too low at lower temperatures, but of crystallization of the solvent beginning. As a result of excessively lowered reaction temperatures, the reaction speed may be so greatly reduced that the yields may even be lowered. As with most chemical reactions, the temperatures used may be lower or higher than those indicated in the examples. However, if the values indicated in the examples are considerably exceeded, side-reactions are to be expected, which reduce the yield and adversely influence the purity of the products.

The crude products resulting from the process of the invention can be worked up to yield the penicillins of the present invention in the manner conventional in penicillin chemistry.

The free penicillins of the formula I and their salts can be interconverted in any suitable manner, methods for such interconversion are known in penicillin chemistry.

The 6-aminopenicillanic acid used as the starting material in the process of the present invention can be obtained according to known processes by splitting penicillin-G, either by fermentation or by chemical splitting (see Netherlands Pat. No. 67/13,809 and German Offenlegungsschrift No. 2,062,925).

The carboxylic acids of the formula XI can be obtained from the amino acids of the formula:

by reaction with compounds of the formula XXI, XXII, XXIII, XXIV or XXV:

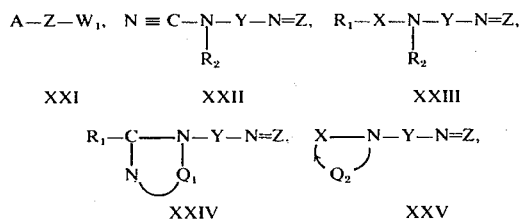

wherein A, B, $Q_1$, $Q_2$, $R_1$, $R_2$, X, Y, Z, C* and W are as above defined.

The production of the compounds of the formula XXI, XXII, XXIII, XXIV and XXV is in each case described in the individual examples which follow.

The production of the compounds of the formula XXII, XIII and XV is described in the literature (see J. Med. Chem. 9 (1966) page 980; Ber. 96 (1963) page 2681, Tetrahedron 17 (1962) page 114).

A compound of the formula XIV was obtained from N,N-dimethylethylenediamine by conversion into the N,N'-bis-trimethylsilyl compound, reaction of the latter with phosgene to give the corresponding cyclic urea, and reacting the cyclic urea with phosgene.

The penicillins according to the present invention can also be obtained from the carboxylic acids of the formula XI, their salts of the formula XIa or their silyl compounds XIb and XIc and 6-aminopenicillanic acid or the silylated 6-aminopenicillanic acids (see formulae XIX and XX) by the customary methods of peptide chemistry (see E. Schröder, and K. Lübke, The Peptids, Methods of Peptide Synthesis, Vol. I, pages 76–128). However, the process of the invention has certain advantages over these customary methods.

The antibacterial activity of the new penicillin compounds was determined in vitro and in vivo. Tables 1 to 3 below give the in vitro minimum inhibitory concentration (MIC) in U/ml* of nutrient medium. The determination was carried out in a liquid medium in the test tube serial dilution test, the reading being taken after 24 hours incubation at 37° C. The MIC is indicated by the non-trubid test tube in the dilution series. The growth medium used was a full medium of the following composition:

*1 mol of penicillin contains 5.9514 × 10⁸ Units (U).

| | |
|---|---|
| Lab Lemco (OXOID) | 10 g |
| Peptone (DIFCO) | 10 g |
| NaCl | 3 g |
| D(+) Dextrose (MERCK) | 10 g |
| Buffer pH 7.4 | 1.000 ml |

The numbers here allocated to the penicillin compounds correspond to the numbers of the Examples in which the particular penicillin is described.

The spectrum of action of the penicillins of the present invention encompasses both Gram-negative and Gram-positive bacteria. The particular advantage of the penicillins according to the present invention is that both in vitro and in vivo in animal experiments they are active against ampicillin- and carbenicilin-resistant bacteria of the group Klebsiella-Aerobacter, against ampicillin- and carbenicillin-resistant indole-positive Proteus and Providencia bacteria, ampicillin- and carbenicillin-resistant *Escherichia coli* strains, and against ampicillin- and carbenicillin-resistant *Pseudomonas aeruginosa* and *Serratia marcescens* bacteria.

The bacteriocidal concentrations required are reached in the serum after parenteral administration. The results of animal experiments for some of the penicillin compounds according to the invention are summarized in Table 3.

The generally excellent action is achieved both on single and on repeated administration. The penicillins according to the present invention are stable to stomach acid. Some of the new penicillins show excellent toleration, which is made particularly clear by the extremely high dosage which is tolerated, without complications, in the case of mice when the penicillins are administered intravenously into the vein of the tail. (Table 5)

Table 1 gives a series of minimum inhibitory concentrations of penicillin No. 4 (see Example 4a) in comparison with carbenicillin.

Table 1

| Type of Bacteria | | Minimum inhibitory concentrations in U/ml | |
|---|---|---|---|
| | | Penicillin No. 4 | Carbenicillin |
| Pseudomonas | Bonn | 16–32 | 200 |
| aeruginosa | Walter | | 100 |
| | F 41 | 25 | 100 |
| | E 27 500 | 12.5 | 100 |
| | V 10 818 | 25 | 100 |
| | V 10 797 | 12.5 | 50 |
| | V 10 887 | 12.5 | 100 |
| | V 10 900 | 12.5 | 50 |
| | A | 12.5 | 25 |
| Klebsiella- | 60 | <0.8 | 100 |
| Aerobacter | 62 | 1.6 | 100 |
| | 63 | 4–16 | 400 |
| | 69 | 1.6 | >400 |
| | 70 | 3 | 400 |
| Klebsiella- | 1852 | >400 | >400 |
| Aerobacter | K 10 | 4–16 | >400 |
| | 1871 | 6 | 400 |
| | 75 | 6 | >400 |
| aerogenes | 418 | 3 | 400 |
| Escherichia | 14 | <1 | 1.6 |
| coli | A 261 | –64 | 400 |
| | C 165 | 1–4 | 12.5 |
| | 183/58 | 1–4 | 12.5 |
| | B | <0.8 | — |
| | B 94 | <0.8 | 1.6 |
| | 55 B 5 | <0.8 | — |
| | T 7 | >400 | >400 |
| | T 20/2 | >400 | >400 |
| | 1465 | >400 | >400 |
| | 26/6 | <0.8 | 3 |
| | N | 1.6 | 6 |
| | S | 32 | 400 |
| Serratia | | | |

Table 1-continued

| Type of Bacteria | | Minimum inhibitory concentrations in U/ml | |
|---|---|---|---|
| | | Penicillin No. 4 | Carbenicillin |
| marcescens | 2 | 1.6 | 12.5 |
| | 3 | 12.5 | 400 |
| | 4 | 1.6 | 12.5 |
| | 6 | 1.6 | 12.5 |
| | 7 | 1.6 | 100 |
| | 9 | <0.8 | 6 |
| | 13 | <0.8 | 6 |
| | K | <0.8 | 6 |
| Providencia | 930 | <0.8 | 6 |
| | 933 | 12.5 | 3 |
| | 945 | <0.8 | 3 |
| Bacillus Proteus rettgeri | Sp. | 0.8 | 1.6 |
| | 1 050 | >400 | >400 |
| | 824 | >400 | >400 |
| mirabilis | Sp. | 1.6 | 1.6 |
| | G. | <0.4 | 1.6 |
| | 605 | 3 | 400 |
| | 1 235 | 1.6 | 3 |
| morganii | Sp. | 3 | 3 |
| | 932 | 6 | 6 |
| | 1 102 | 200 | >800 |

Table 1-continued

| Type of Bacteria | | Minimum inhibitory concentrations in U/ml | |
|---|---|---|---|
| | | Penicillin No. 4 | Carbenicillin |
| vulgaris | 1 017 | 1.6 | 3 |
| | 3 400 | 6 | 50 |
| Haemophilus influenzae | 2 689 | 0.25 | 1.6 |
| | 2 718 | 0.1 | 0.8 |
| | 2 786 | 0.06 | 1.6 |
| | 2 788 | 0.5 | <0.4 |
| | 2 684 | 0.1 | — |
| Streptococcus faecalis | 8 709 | 12.5 | 200 |
| | 8 711 | 3 | 50 |
| | 8 698 | 1.6 | 100 |
| Staphylococcus aureus | BRL 1 756 | 200 | 200 |
| | 133 | 1 | 1 |
| | P 209 | <0.8 | <0.8 |
| | SG 511 | <0.8 | <0.8 |

Table 2 gives the minimum inhibitory concentrations (MIC values) in U/ml of some penicillins of the present invention, the penicillin number corresponding to the example number for a series of types of bacteria:

Table 2

| Penicillin No. | Escherichia coli | | | Prot. vulg. | Prot. morg. | Psdm. aerug | | Klebsiella | | Staph. aur. | | Strept. faec. |
|---|---|---|---|---|---|---|---|---|---|---|---|---|
| | 14 | A 261 | C 165 | 183/58 | 1017 | 932 | Bonn | Walter | K 10 | 63 | 1756 E | 133 | ATCC 9790 |
| 1 | <0.8 | 400 | 3 | 3 | 6 | 6 | 25 | 50 | 100 | 25 | 400 | <0.8 | 25 |
| 2 | <0.8 | 100 | 1.6 | 1.6 | 6 | 1.6 | 50 | 25 | 50 | 12.5 | 200 | <0.8 | 50 |
| 3 | <1 | 256 | 4 | 4 | 8 | 8 | 16 | 16 | 16 | 16 | >256 | 4 | 64 |
| 4 | <1 | 32–64 | 1–4 | 1–4 | 1.6 | 6 | 16–32 | 8 | 4–16 | 4–16 | 64–256 | 1 | 16–32 |
| 5 | <1 | 256 | 4 | 4 | 4 | 32 | 32 | 32 | 32 | 16 | >256 | <1 | 32 |
| 6 | 4 | >256 | 4 | 4 | 16 | 64 | 32 | 32 | 16 | 32 | 64 | <1 | 32 |
| 7 | <1 | >256 | 4 | <1 | 16 | 4 | 16 | 8 | 4 | 4 | 128 | <1 | 16 |
| 8 | 4 >256 | 4 | 4 | 32 | 64 | 32 | 32 | 8 | 32 | 128 | 4 | 128 | |
| 9 | <1 | >256 | 4 | 4 | 32 | 32 | 64 | 32 | 4 | 8 | >256 | 4 | 128 |
| 10 | <1 | >256 | 4 | 4 | 8 | 4 | 64 | 256 | 8 | 8 | >256 | 4 | 128 |
| 11 | <1 | >256 | 4 | <1 | 16 | 8 | 32 | 16 | 4 | 4 | 64 | <1 | 16 |
| 12 | <1 | 64 | 4 | <1 | 4 | 8 | 32* | 32 | 4 | 8 | 256 | <1 | 32 |
| 13 | <1 | 128 | 4 | <1 | 4 | <1 | 16* | 16 | 4 | 8 | 128 | <1 | 16 |
| 14 | <1 | 128 | 4 | <1 | 4 | <1 | 32* | 32 | 4 | 4 | 128 | <1 | 32 |
| 19 | 4 | >256 | 8 | 16 | 16 | 32 | — | — | — | — | — | — | — |
| 20 | 4 | >256 | 8 | 64 | 16 | 8 | 8* | 16 | 32 | 64 | 128 | <1 | 32 |
| 21 | <1 | 256 | 4 | <1 | 4 | 4 | 32* | 32 | 8 | 8 | 256 | <1 | 64 |
| Ampicillin | 0.8 | >400 | 6 | 200 | 400 | | 200 | 200 | 100–200 | 100–200 | | <1 | 12.5 |
| Carbenicillin | 1.6 | 400 | 12.5 | 12.5 | 3 | 6 | 200 | 100 | >400 | 400 | 200 | 1 | |
| 22 | 4 | >256 | 8 | 8 | 16 | 128 | 16 | 32 | 32 | 64 | 128 | 4 | 32 |
| 23 | <1 | 128 | 4 | <1 | 4 | <1 | 16 | 32 | 8 | 8 | 64 | <1 | 32 |
| 24 | <1 | 512 | 2 | <1 | 2 | 2 | 32 | 32 | 4 | 8 | 32 | <1 | 16 |
| 25 | 8 | >256 | 16 | 32 | 16 | 4 | 64 | 32 | 64 | 64 | 64 | <1 | 16 |
| 26 | 4 | >256 | 4 | 4 | 4 | 4 | 32 | 64 | 32 | 16 | 64 | <1 | 8 |
| 27 | 0.5 | >256 | 1 | 0.5 | 1 | <1 | 32 | 32 | 4 | 4 | 64 | <0.25 | 4 |
| 29 | 4 | <256 | 16 | 32 | 64 | 128 | 16 | 16 | 64 | 64 | 256 | <1 | 16 |
| 30 | <1 | >256 | 8 | 64 | 4 | 8 | 32 | 32 | 128 | 64 | 256 | 4 | 128 |
| 31 | 8 | >256 | 32 | 128 | >256 | 64 | 256 | 256 | >256 | >256 | 64 | <1 | 32 |
| 32 | 4 | >256 | 8 | 8 | 8 | 8 | 256 | 128 | 32 | 16 | 64 | <1 | 16 |

*= Pseudomonas aeruginosa F 41.

TABLE 3

| Penicillin No. | BACTERIA TYPE | | | | | | | | | | | | |
|---|---|---|---|---|---|---|---|---|---|---|---|---|---|
| | Escherichia coli | | | | Proteus | | Pseudomonas aeruginosa | | Klebsiella | | Staphylococcus aureus | | Strept. faec. |
| | 14 | A 261 | C 165 | 183/58 | vulg. 1017 | morg. 932 | F41 | Walter | K 10 | 63 | 1756 E | 133 | ATCC 9790 |
| 1 | <0.8 | 200 | 3.1 | 1.6 | 3.1 | — | 50 | 50 | 6.2 | 12.5 | 400 | <0.8 | 25 |
| 2 | <1 | 256 | 4 | 4 | 8 | 8 | 128 | 64 | 32 | 128 | 64 | <1 | 64 |
| 3 | <1 | 256 | 4 | 4 | 4 | 16 | 64 | 64 | 16 | 256 | 128 | <1 | 32 |
| 4 | 1.6 | 200 | 12.5 | 6.2 | 12.5 | — | 200 | 200 | 50 | 100 | 200 | <0.8 | 100 |
| 5 | 256 | ≧256 | ≧256 | 256 | 256 | 32 | ≧256 | ≧256 | ≧256 | ≧256 | ≧256 | 4 | 256 |
| 6 | 8 | >512 | 16 | 16 | 32 | 64 | 256 | 128 | 128 | 256 | 128 | 2 | 128 |
| 7 | 4 | 512 | 16 | 8 | 32 | 16 | 128 | 64 | 32 | 128 | 64 | <1 | 64 |
| 8 | 2 | 512 | 8 | 8 | 16 | 32 | 128 | 64 | 32 | 128 | ~64 | <1 | 64 |
| 9 | 2 | 512 | 8 | 8 | 8 | 8 | 64 | 64 | 32 | 128 | 64 | 2 | 64 |
| 10 | 128 | >512 | 512 | 256 | 256 | 256 | >512 | >512 | >512 | >512 | 512 | 16 | >512 |

TABLE 3-continued

| Peni-cill-in No. | BACTERIA TYPE | | | | | | | | | | | |
|---|---|---|---|---|---|---|---|---|---|---|---|---|
| | Escherichia coli | | | Proteus | | Pseudomonas aeruginosa | | Klebsiella | | Staphylococcus aureus | | Strept. faec. |
| | 14 | A 261 | C 165 | 183/58 | vulg. 1017 | morg. 932 | F41 | Walter | K 10 | 63 | 1756 E | 133 | ATCC 9790 |
| 11 | <1 | 512 | 4 | 2 | 4 | 16 | 64 | 64 | 16 | 16 | 128 | 2 | 64 |
| 13 | 4 >256 | 8 | 4 | 16 | 128 | 128 | 128 | 32 | 64 | 256 | 4 | 128 | |
| 18 | 1 | >256 | 8 | 16 | 4 | <1 | 256 | 256 | 32 | 32 | 64 | <1 | 32 |
| 19 | 4 | >256 | 8 | 16 | 32 | 4 | 64 | 64 | 32 | 4 | 128 | <1 | 32 |
| 20 | 4 | >256 | 8 | 8 | 8 | 32 | 64 | 32 | 32 | 32 | 64 | <1 | 16 |
| Ampi-cill-in | 0.8 | >400 | 6 | 200 | 400 | — | — | 200 | 100–200 | 100–200 | — | <1 | 12.5 |

Tables 1 to 3 indicate the superiority of the in vitro activity of penicillins of the present invention as compared to the commercially available products ampicillin and carbenicillin.

Table 4 shows the effective dose ($ED_{50}$ - values) in the case of mice infected intraperitoneally with the bacterium indicated. This demonstrates the superiority of penicillins according to the present invention in animal experiments with Gram-negative bacteria as compared to carbenicillin. Further, Table 4 also shows the good action against Gram-positive bacteria.

Table 4

Results of animal experiments with white mice for representative penicillins according to the invention ($ED_{50}$ on subcutaneous treatment, in U/kg)

| Type of bacteria | Carbeni-cillin | Penicillin No. | | |
|---|---|---|---|---|
| | | 1 | 2 | 4 |
| Klebsiella 63 | >2 × 300,000 | 2 × 60,000 | 2 × 40,000 | 2 × 40,000 |
| Klebsiella 1871 | >1 × 500,000 | | | 1 × 350,000 |
| Prot. vulg. 1017 | 2 × 50,000 | | 2 × 25,000 | 2 × 25,000 |
| Prot. morg. 932 | 2 × 75,000 | | | 2 × 75,000 |
| Psdm. aerug. Walter | 4 × 150,000 | | | 4 × 150,000 |
| Psdm. aerug. F 41 | 4 × 100,000 | | | 4 × 25,000 |
| | Propicillin | | | |
| Staph. aur. 133 | 2 × 2,000 | 2 × 3,000 | 2 × 4,000 | 2 × 2,500 |

Table 5 shows the extremely high level to which some of the penicillins according to the present invention are tolerated, i.e., the relatively low toxicity of these penicillins.

Table 5

| Penicillin No. | $LD_{50}$ on intravenous injection into the vein of the tail of mice, in mg/kg |
|---|---|
| 2 | 3,000 |
| 4 | 3,000 |

The generally excellent antibacterial activity of the present penicillins is achieved both on single and on repeated administration. The penicillins according to the present invention are stable to stomach acid. Some of the new penicillins show excellent toleration, which is particularly made clear by the extremely high dosage which is tolerated, without complications, in the case of mice when administered intravenously into the vein of the tail.

The present invention also provides a pharmaceutical composition containing as active ingredient a compound of the invention in combination with a pharmaceutically acceptable, non-toxic, inert diluent or carrier.

The invention further provides a pharmaceutical composition containing as active ingredient a compound of the invention in the form of a sterile or isotonic aqueous solution.

The invention also provides a medicament in dosage unit form comprising a compound of the invention either alone or in combination with a diluent or carrier.

The invention also provides a medicament in the form of tablets (including lozenges and granules), dragees, capsules, pills, ampoules or suppositories comprising a compound of the invention either alone or in combination with a suitable diluent or carrier.

"Medicament" as used in this Specification means physically discrete coherent portions suitable for medical administration. "Medicament in dosage unit form" as used in this Specification means physically discrete coherent portions suitable for medical administration each containing a daily dose or a multiple (up to four times) or sub-multiple (down to a fortieth) of a daily dose of the compound of the invention. Whether the medicament contains a daily dose or, for example, a half, a third, or a quarter of a daily dose will depend on whether the medicament is to be administered once or, for example, twice, three times or four times a day respectively.

The pharmaceutical compositions according to the present invention may, for example, take the form of ointments, gels, pastes, creams, sprays (including aerosols), lotions, suspensions, solutions and emulsions of the active ingredient in aqueous or non-aqueous diluents, syrups, granules or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredients can also be made up in microencapsulated form together with one or several of the above-mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents, such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example, ground nut oil], glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminum metahydroxide, bentonite, agar-agar and tragacanth or mixture thereof.

All the pharmaceutical compositions according to the present invention can also contain coloring agents and preservatives as well as perfumes and flavoring additives (e.g. peppermint oil and eucalyptus oil) and sweetening agents (e.g. saccharin).

The pharmaceutical compositions according to the present invention preferably contain about 0.1 to 99.5%, more preferably from about 0.5 to 95%, of the active ingredient by weight of the total composition.

In addition to a penicillin of the present invention, the pharmaceutical compositions and medicaments according to the invention can also contain other pharmaceutically active compounds. They may also contain a plurality of pencillins of the present invention.

The discrete coherent portions constituting the medicament according to the invention (whether in dosage unit form or not) may be, for example, any of the following: tablets, (including lozenges and granules), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration to human subjects of the penicillins of the present invention is 500,000 to 90,000,000 units of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including the prevention, relief and cure of) the above-mentioned diseases in human and non-human animals, which comprises administering to the animals a penicillin of the present invention alone or in combination with a suitable diluent or carrier or in the form of a medicament according to the present invention.

These aforedisclosed penicillins are suitable for administration perorally, parenterally (for example intramuscularly, intraperitoneally or, in particular, intravenously, and intravenously by continuous drip), rectally or topically.

In general it has proved advantageous to administer amounts of from 25,000 to 1,000,000 $\mu$/kg of body weight per day to achieve effective results. Nevertheless, it can at times be necesary to deviate from those dosage rates, and in particular to do so as a function of the nature and body weight of the human or non-human animal subject to be treated, the individual reaction of this subject to the treatment, the type of formulation in which the active ingredient is administered and the mode in which the administration is carried out, and the point in the progress of the disease or interval at which it is to be administered. Thus it may in some cases suffice to use less than the above-mentioned minimum dosage rate, while other cases the upper limit mentioned must be exceeded to achieve the desired results. Where larger amounts are administered it can be advisable to divide these into several individual administrations over the course of the day.

The present invention also comprises an animal feedstuff comprising a penicillin according to the present invention in combination with a nutritious material.

The α-aminobenzylpenicillin used in the Examples contained about 14% of water but anhydrous α-aminobenzylpencillins (U.S. Pat. No. 3,144,445) can be employed equally well.

Unless expressly stated otherwise, "ampicillin" is intended to mean α-aminobenzylpenicillin with the $D(-)-=$ R-configuration in the side-chain.

The β-lactam content was determined iodometrically. All penicillins described herein showed an IR-spectrum corresponding to their structure.

The NMR-spectra were recorded in CD₃OD solution and the signals indicated in the examples agree with the particular structure; the position of the signals is given in τ-values.

In calculating the analytical data, the water content is taken into account.

Under the heading: "Activity in animal experiments", A means that the particular penicillin, when used subcutaneously in mice against *Pseudomonas aeruginosa* F 41, is more active than carbenicillin, B denotes that it is more active against Klebsiella 63 than carbenicillin, C denotes that is is more active against Klebsiella 63 than cephalothin and D denotes that it is more active against Klebsiella 63 than cephalexin.

The figures (U/ml) quoted in the activities against certain bacteria are minimum inhibitory concentrations in the test tube series dilution test after 24 hours incubation.

The following non-limitative Examples more particulary illustrate the present invention.

EXAMPLE 1

A. Sodium D(-)-α-[(3-acetyl-imidazolidin-2-on-1-yl)-carbonylamino]-benzylpenicillin:

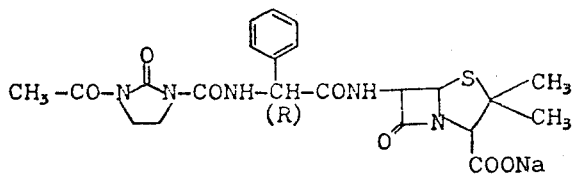

17.5 parts by weight of ampicillin were suspended in 80% strength aqueous tetrahydrofurane (140 parts by volume) and sufficient triethylamine (approx. 6.3 parts by volume) was added dropwise while stirring, at 20°C, just to produce a clear solution and to give a pH value of between 7.5 and 8.2 (glass electrode). The mixture was cooled to 0°C and 7.6 parts by weight of 3-acetyl-imidazolidin-2-on-1-carbonyl chloride were added gradually in portions over the course of 30 minutes, while the mixture was stirred and kept at a pH value of between 7 and 8 by simultaneous addition of triethylamine. The mixture was stirred for 10 minutes at 0°C and subsequently further stirred at room temperature until no further addition of triethylamine was necessary to maintain a pH value of 7-8. 150 parts by volume of water were now added and the tetrahydrofurane was largely removed in a rotary evaporator at room temperature. The residual aqueous solution was extracted once by shaking with ethyl acetate, covered with 250 parts by volume of fresh ethyl acetate and acidified to pH 1.5–2.0 with dilute hydrochloric acid while being cooled with ice. The organic phase was separated off, washed twice with 50 parts by volume of water at a time and dried for 1 hour over anhydrous MgSO₄ in a refrigerator. After filtration, about 45 parts by volume of a 1 molar solution of sodium 2-ethyl-hexanoate in ether containing methanol were added to the solution of the penicillin. The mixture was now concentrated on a rotary evaporator until it had an oily consistency and was dissolved in a sufficient amount of methanol by vigorous shaking, and the solution was rapidly added dropwise, with vigorous stirring, to 500 parts by volume of ether which contained 10% of methanol. The precipitate was allowed to settle for 30 minutes, the solution was decanted from the precipitate, and the latter was again suspended in ether, filtered off and washed with anhydrous ether. After drying over P₂O₅ in a vacuum dessicator, the sodium salt of the penicillin was obtained in the form of a white solid substance.

Yield: 95%
β-Lactam content: 84%
Calculated: C, 48.3; H, 4.9; N, 12.8; S, 5.8.
Found: C, 48.6; H, (6.2); N, 11.7; S, 5.6.
NMR-signals at τ = 2.3–2.7 (5H), 4.3 (1H), 4.5 (2H), 5.8 (1H), 6.15 (4H), 7.5 (3H), 8.4 (3H) and 8.45 ppm (3H).

The product showed only one antibiotically active spot in the electropherogram.

Activity in animal experiments: B and C
Activity against E. coli 183/58: 3
Activity against Prot. morg. 932: 6
Activity against Psdm. aerug. Bonn: 25
Activity against Klebs. 63 : 25

B. 3-Acetyl-imidazolidin-2-on-1-carbonyl chloride:

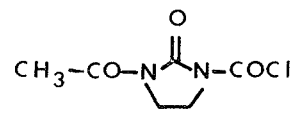

20 parts by weight of N-acetyl-imidazolid-2-one mixed with 25 parts by weight of triethylamine and 150 parts by volume of dry benzene were first taken and 27 parts by weight of trimethylchlorosilane in 40 parts by volume of benzzene were added dropwise at room temperature over the course of 30 minutes, with stirring. The mixture was subsequently boiled for 18 hours under reflux, moisture being excluded, and the triethylamine hydrochloride which precipitated (22 parts by weight = 100%) was filtered off after cooling and carefully rinsed with dry benzene. The benzene solution thus obtained was treated with a solution of 17 parts by weight of phosgene in 50 parts by volume of benzene at 5° C and left to stand overnight at 5° C. Thereafter the solvent was stripped off in vacuo and the residue was dried under an oil pump. It was recrystallized from acetone/pentane mixture.

Yield: 81% Melting point = 104° C
Calculated: C, 37.7; H, 3.7; Cl, 18.6; N, 14.7.
Found: C, 39.3; H, 4.3; Cl, 17.7; N, 14.7.
IR-bands at 1798, 1740, 1690 and 1660 cm⁻¹.
NMR-signals at τ = 5.65 – 6.3 (4H) and 7.45 ppm (3H)

According to the NMR-spectrum, the product still contained 5–10% of N-acetyl-imidazolidone, which however does not interfere in the reaction with ampicillin (Example 1A).

C. N-acetyl-imidazolid-2-one

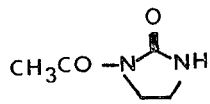

23.6 parts by weight of acetyl chloride in 100 parts by volume of tetrahydrofurane were added dropwise over the course of 60 minutes to a suspension of 25.8 parts by weight of imidazol-2-one in 350 parts by volume of dry tetrahydrofurane. at 0° C. The mixture was stirred for 3 hours at room temperature, dry air was subsequently blown through the solution for some time, the solvent was then removed in vacuo and the residue was recrystallized from boiling nitromethane.

Yield: 52% Melting point = 188° C
Calculated: C, 46.9; H, 6.9; N, 21.9.
Found: C, 47.0; H, 6.2; N, 22.5.
IR-bands at 3230, 1730 and 1640 cm$^{-1}$.
NMR-signals at $\tau = 6.2$ (2H), 6.5 (2H) and 7.6 ppm (3H).

EXAMPLE 2

A. Sodium D(-)-α-[(3-methylaminocarbonyl-imidazolidin-2-on-1-yl)-carbonylamino]-benzylpenicillin:

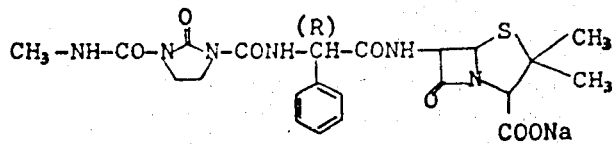

This penicillin was produced as described in Example 1A from 6.5 parts by weight of 1-(N-methyl-N-trimethylsilyl-amino-carbonyl)-imidazolid-2-one and 14 parts by weight of ampicillin.

Yield: 27%
β-Lactam content: 83%
Calculated: C, 46.5; H, 4.9; N, 14.8; S, 5.6.
Found: C, 46.0; H, 5.6; N, 14.0; S, 5.2.
IR-bands at 3330, 1765, 1722, 1672 and 1266 cm$^{-1}$.
NMR-signals at $\tau$ = 2.3–2.8 (5H), 4.4 (1H), 4.55 (2H), 5.85 (1H) 6.25 (4H), 7.15(3H), 8.45 (3H) and 8.5 ppm (3H).

Activity in animal experiments: B, C and D.
Activity against E. coli 183/58: 1.6
Activity against Prot. morg. 932: 1.6
Activity against Psdm. aerug. Walter: 25
Activity against Klebsiella 63: 12

B. 3-(N-methyl-N-trimethylsilyl-aminocarbonyl)-imidazolidin-2-on-1-carbonyl chloride:

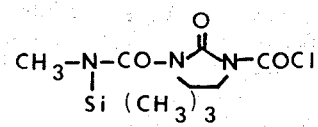

A suspension of 7.1 parts by weight of N-methylaminocarbonyl-imidazolid-2-one in 150 parts by volume of benzene and 12 parts by weight of triethylamine was treated dropwise over the course of 30 minutes with 13 parts by weight of trimethylchlorosilane, at room temperature, with stirring and the exclusion of moisture, and the mixture was subsequently kept under reflux for 24 hours. It was then cooled, the triethylamine hydrochloride was filtered off and rinsed with benzene, and the filtrate was treated with 5 parts by weight of phosgene in 20 parts by volume of benzene. The mixture was left to stand in a refrigerator overnight, the solvent was stripped off in vacuo and the residue was dried under an oil pump. The residue was suspended in a 1:1 mixture of benzene and pentane and filtered off, the filtrate was evaporated to dryness and the residue was suspended in dry ether and again filtered off. The filtrate thus obtained was cooled in ice for approximately 1 hour, the precipitate which formed was again filtered off and the resulting solution was evaporated to dryness. The semi-solid mass was dried under an oil pump.

According to the NMR-spectrum the substance thus obtained consisted of a 3:1 mixture of 1-methylaminocarbonylimidazolid-2-one (NMR-signals at 6.1, 6.5 and 7.15 $\tau$) and 3-(N-methyl-N-trimethyl-silylamino-carbonyl)-imidazolidin-2-on-1-carbonyl chloride (NMR-signals at 6.0, 7.0 and 9.7 ppm) which could be reacted with ampicillin to give the corresponding penicillin (Example 2A).

C. N-(methylaminocarbonyl)-imidazolidin-2-one:

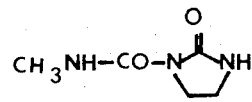

14.9 parts by weight of N-chlorocarbonylimidazolidone-2 were added in portions, under cooling with ice, to a solution of 20 parts by weight of a 50% strength aqueous methylamine solution in 50 parts by weight of tetrahydrofurane which had been adjusted to a pH value of 8.5 with concentrated hydrochloric acid, and at the same time a pH value of 8.5 was maintained by simultaneous addition of triethylamine. Thereafter the mixture was further stirred until the pH value had not changed further in 15 minutes, even without addition of triethylamine. A pH value of 6.5 was established by adding HCl and the tetrahydrofurane was stripped off in vacuo. The product was filtered off, rinsed with a little ice-water and recrystallized from methanol.

Yield: 72% Melting point = 198° C.
Calculated: C, 41.9; H, 6.3; N, 29.4.
Found: C, 41.7; H, 6.5; N, 30.2.
IR-bands at 3220, 1728 and 1645 cm$^{-1}$.
NMR-signals at $\tau$ = 2.0 (1H), 2.5 (1H), 6.2 )2H), 6.6 (2H) and 7.2 ppm (3H).

EXAMPLE 3

Sodium D(-)-α-[(3-methoxycarbonyl-imidazolidin-2-on-1-yl)-carbonylamino]-benzylpenicillin:

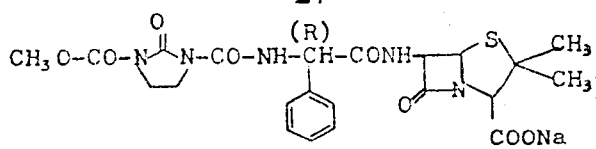

This penicillin was produced as described in Example 1 from 7.8 parts by weight of 3-methoxy-carbonylimidazolidin-2-on-1-carbonyl chloride and 17.5 parts by weight of ampicillin.

Yield: 97%
β-Lactam content: 87%
Calculated: C, 48.8; H, 4.4; N, 12.9; S, 5.9.
Found: C, 48.6; H(6.7); N, 11.0; S, 5.5.
IR-bands at 3300, 1775, 1740, 1667, 1605 and 1262 cm$^{-1}$.
NMR-signals at $\tau$ = 2.3–2.8 (5H), 4.4 (1H), 4.5 (2H), 5.8 (1H). 6.15 (3H), 6.0–6.3 (4H), 8.4 (3H) and 8.5 ppm (3H).

The product only shows one antibiotically active spot in the electropherogram.
Activity in animal experiments: B and C.
Activity against *E. coli* 183/58: 4
Activity against *Prot. morg.* 932: 8
Activity against *Psdm. aerug.* Walter: 16
Activity against *Klebsiella* K 10: 16

B. 3-Methoxycarbonyl-imidazolidin-2-on-1-carbonyl chloride

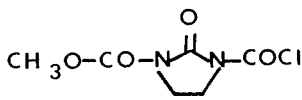

This carbamic acid chloride was produced as described in Example 1B from 8 parts by weight of N-methoxycarbonyl-imidazolid-2-one, 9.7 parts by weight of trimethylchlorosilane, 9 parts by weight of triethylamine and 6.2 parts by weight of phosgene.
Yield: 72%; Melting point = 129° C.
Calculated: C, 34.8; H, 3.4; Cl, 17.2; N, 13.6.
Found: C, 34.8; H, 3.4; Cl, 17.1; N, 13.6.
IR-bands at 1820, 1737, 1690 and 1260 cm$^{-1}$.
NMR-signals at $\tau$ = 5.7–6.3 (4H) and 6.1 ppm (3H).

C. N-methoxycarbonyl-imidazolid-2-one

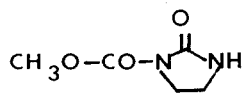

14.9 parts by weight of N-chlorocarbonyl-imidazolid-2-one were introduced into 70 parts by volume of ice-cold methanol and the mixture was stirred for 1 hour at room temperature and subsequently for 1 hour at 40°–50° C. After the excess methanol had been stripped off, the residue was recrystallized from acetone.
Yield: 55% Melting point = 185° C.
Calculated: C, 41.6; H, 5.5; N, 19.4.
Found: C, 41.8; H, 4.8; N, 19.2.
IR-bands at 3320, 1745 and 1670 cm$^{-1}$.

EXAMPLE 4

A. Sodium D(−)-α-[(3-methylsulphonyl-imidazolidin-2-on-1-yl)-carbonylamino]-benzylpenicillin

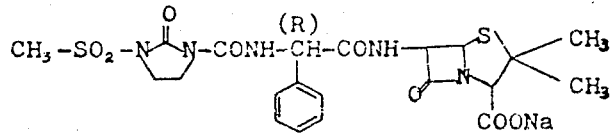

This penicillin was produced as described in Example 1A from 5.1 parts by weight of 3-methyl-sulphonyl-imidazolidin-2-on-1-carbonyl chloride and 9.3 parts by weight of ampicillin.
Yield: >90%
β-Lactam content: 81 %
Calculated: C, 42.7; H, 4.6; N, 11.8; S, 10.8.
Found: C, 42.7; H, 5.4; N, 11.6; S, 11.4.
IR-bands at 3305, 1760, 1728, 1670, 1605, 1360 and 1174 cm$^{-1}$.
NMR-signals at $\tau$ = 2.3–2.7 (5H), 4.35(1H), 4.5(2H), 5.8(1H), 5.8–6.2 (4H), 6.65 (3H), 8.4 (3H) and 8.5 ppm (3H).
Activity in animal experiments: A, B, C and D
Activity against *E. coli* A 261: 32–64
Activity against *E. coli* 183/58: 1–4
Activity against Proteus 1017: 1.6
Activity against Psdm. aerug. Walter: 4–16
Activity against Klebsiella K 10: 4–16

B. 1-Chlorocarbonyl-3-methylsulphonyl-imidazolid-2-one:

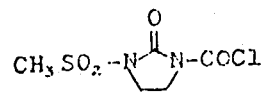

16.4 parts by weight of 1-methylsulphonyl-imidazolid- 2-one in dioxane were boiled for 3 days with 27 parts by weight of trimethylchlorosilane and 20 parts by weight of triethylamine. The triethylamine hydrochloride which precipitated was filtered off, 11 parts by weight of phosgene were added to the filtrate and the mixture was left to stand overnight at room temperature. It was then evaporated to dryness and the residue recrystallized from boiling acetone.
Yield: 70% Melting point = 178°
Calculated: C, 26.5; H, 3.1; Cl, 15.7; N, 12.4; S, 14.1.
Found: C, 27.2; H, 3.4; Cl, 15.3; N, 12.0; S, 14.1.
NMR-signals at $\tau$ = 5.6–6.2 (4H) and 6.6 ppm (3H).
IR-bands at 3010, 1807, 1721, 1360, 1165, 984 and 742 cm$^{-1}$.

The same product can also be manufactured successfully from 1-methylsulphonyl-imidazolid-2-one and excess phosgene in methylene chloride.

C. N-methylsulphonyl-imidazolid-2-one:

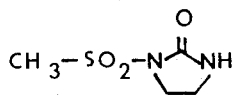

Instructions 1

63 parts by weight of methane sulphochloride were added dropwise at room temperature to a suspension of 43 parts by weight of imidazolidone-2 in 400 parts by volume of dry tetrahydrofurane and the mixture was stirred for 1 hour at 30°–40° C and then heated under reflux for 1 hour. Thereafter the solvent was distilled off in vacuo and the residue was kept under an oil pump for 1 hour at 60° C. The residue was recrystallized from warm acetone.

Yield: 25% Melting point: 193° C
Calculated: C, 29.3; H, 4.9; N, 17.1; S, 19.5.
Found: C, 29.0; H, 5.0; N, 17.2; S, 19.6.
IR-bands at 3250, 3115, 1715, 1350 and 1160 cm$^{-1}$.
NMR-signals at $\tau$= 2.4 (1H), 6.2 (2H), 6.5(2H) and 6.8 ppm (3H).

Instructions 2

80 parts be weight of methanesulphochloride followed by 56 parts by weight of triethylamine were added dropwise over the course of 30 minutes, while stirring, to a suspension of 43 parts by weight of imidazolidone-2 in 300 parts by volume of dry tetrahydrofurane, in such a way that the internal temperature was about 35°–40° C. The mixture was stirred for a further 2 hours at 45° C, the solvent was then stripped off in vacuo, the residue which remained was extracted twice with 150 parts by volume of chloroform at a time, and the crystals which remained were recrystallized from methanol.

Yield: 49%. The product agrees, according to melting point and I R-spectrum, with the N-methylsulphonylimidazolid-2-one described above.

EXAMPLE 5

A. Sodium D(−)-α-[(3-aminocarbonyl-imidazolidin-2-on-1-yl)-carbonylamino]-benzylpenicillin:

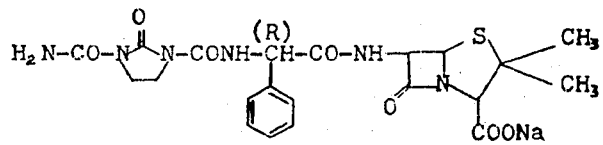

16.2 parts by weight of ampicillin in 170 parts by volume of methylene chloride were stirred by 10 parts by weight of triethylamine and 20 parts by weight of anhydrous sodium sulphate for 90 minutes at room temperature. Thereafter the mixture was filtered and the solution thus obtained was treated, at 0° C, with a suspension of 11 parts by weight of 3-aminocarbonyl-imidazolidin -2-on-1-carbonyl chloride in 30 parts by volume of methylene chloride. The mixture was stirred for 1 hour at 0° C and 1 hour at room temperature and poured into 200 parts by volume of water, the pH was adjusted to 7 and the methylene chloride was stripped off in vacuo. The aqueous solution thus obtained was extracted once with 100 parts by volume of ethyl acetate, covered with 300 parts by volume of fresh ethyl acetate and adjusted to pH = 1.5–2.0 with dilute hydrochloric acid, while cooling with ice. The precipitate formed which was relatively sparingly soluble in ethyl acetate and consisted of the slightly contaminated free acid of the penicillin, was filtered off and washed with water. The organic phase was now separated from the water, washed once with water and dried over MgSO$_4$, and after addition of sodium 2-ethylhexanoate the penicillin was obtained in the form of its sodium salt, as described in Example 1A.

Yield: 25%
β-Lactam content: 76%
Calculated: C, 45.5; H, 4.7; N, 15.2; S, 5.8.
Found: C, 45.6; H, 6.0; N, 13.7; S, 5.6.
IR-bands at 3300, 1760, 1725, 1670 and 1275 cm$^{-1}$.
NMR-signals at $\tau$= 2.3–2.8 (5H), 4.4 (1H), 4.5 (2H), 5.8 (1H), 6.2 (4H), 8.4 (3H) and 8.5 ppm (3H).

The free penicillin-acid obtained in 37% yield showed a β-lactam content of 65% and according to analysis and spectra had the correct structure.

Activity in animal experiments: B, C and D.
Activity against *E. coli* 183/58: 4
Activity against Proteus 1017: 4
Activity against *Psdm. aerug.* Walter: 32
Activity against Klebsiella 63: 16

B. 3-Aminocarbonyl-imidazolidin-2-one-1-carbonyl chloride:

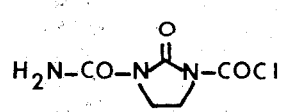

The mixture of 7.7 parts by weight of N-aminocarbonyl-imidazolid-2-one, 16.3 parts by weight of trimethylchlorosilane, 15 parts by weight of triethylamine and 100 parts by volume of benzene was converted, in the manner described in Example 2B, firstly into the silyl compound and subsequently, with 6 parts by weight of phosgene, into the carbamic acid chloride.

Yield: 11.6 parts by weight.

IR-bands at 3400, 3300, 2950, 2895, 1795 and 1600 cm$^{-1}$.

C. N-aminocarbonyl-imidazolid-2-one

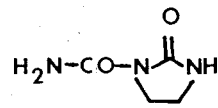

29.7 parts by weight of N-chlorocarbonyl-imidazolid-2-one, were reacted at pH = 8.5 and room temperature with 20 parts by volume of 25% strength aqueous solution of NH$_3$ in 80% strength aqueous tetrahydrofurane. After stripping off the tetrahydrofurane in vacuo, the product which precipitated was filtered off and washed with a little ice water. Yield after drying over $P_2O_5$ in a desiccator: 62%. Melting point 200° C.
Calculated: C, 37.2; H, 5.4; N, 32.6.
Found: C, 37.7; H, 5.3; N, 33.2.
IR-bands at 3345, 3260, 3200, 1740, 1677 and 1590 $cm^{-1}$.

A further 12% of the product were obtainable from the filtrate of the main precipitation, evaporated to dryness, by extracting it by boiling with several portions of acetone (melting point = 199° C, IR-bands as for the main amount).

EXAMPLE 6

A. Sodium D(-)-α-[(3-dimethylaminocarbonyl-imidazolidin-2-on-1-yl)-carbonylamino]-benzylpenicillin:

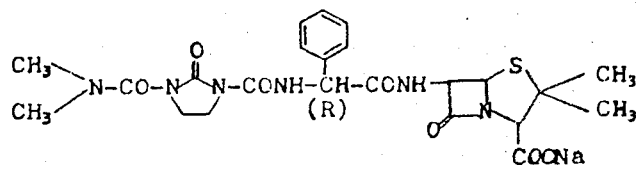

This penicillin was produced as described in Example 1A from 7.1 parts by weight of 3-dimethylaminocarbonyl-imidazolidin-2-on-1-carbonyl chloride and 13 parts by weight of ampicillin.
Yield: 76%
β-Lactam content: 93%
Calculated: C, 47.9; H, 5.1; N, 14.6; S, 5.5.
Found: C, 48.1; H, 5.7; N, 14.0; S, 6.1.
IR-bands at 3290, 1760, 1662, 1600 and 1260 $cm^{-1}$.
NMR-signals at $\tau=$ 2.4–2.75 (5H), 4.4 (1H), 4.53 (2H), 5.8 (1H), 6.2 (4H), 7.0 (6H), 8.43 (3H), and 8.5 ppm (3H).
Activity in animal experiments: B, C and D.
Activity against *E. coli* 183/58: 4
Activity against Proteus 1017: 16
Activity against *Psdm. aerug.* Walter: 32
Activity against Klebsiella K 10: 16

B. 3-Dimethylaminocarbonyl-imidazolidin-2-on-1-carbonyl chloride:

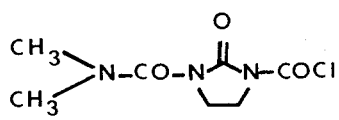

This carbamic acid chloride was produced as described in Example 1B from 6 parts by weight of N-dimethylamino-carbonyl-imidazolidone-2. Crystalline substance.
Yield: 93%
Calculated: C, 38.3; H, 4.6; Cl, 16.2; N, 19.1.
Found: C, 38.8; H, 5.0; Cl, 16.4; N, (17.3).
IR-bands at 2930, 1800, 1758, 1720 and 1675 $cm^{-1}$.

C. N-dimethylaminocarbonyl-imidazolid-2-one:

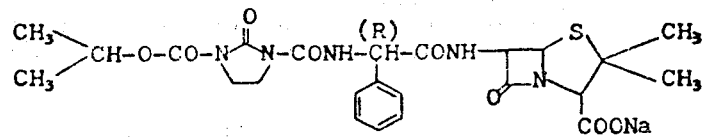

A mixture of 50 parts by volume of a 50% strength aqueous dimethylamine solution and 70 parts by volume of tetrahydrofurane was adjusted to pH = 8 with 5 N hydrochoric acid. 14.9 parts by weight of N-chlorocarbonyl-imidazolid-2-one were added gradually thereto while stirring and cooling with ice and the pH value was maintained by simultaneous addition of further dimethylamine solution. The mixture was further stirred until the pH was constant, the tetrahydrofurane was then stripped off and the residue was saturated with sodium chloride and repeatedly extracted with ethyl acetate. The organic solution was washed and saturated sodium chloride solution, dried over $MgSO_4$ and filtered, and the solvent was evaporated off. The residue was recrystallized from acetone and dried in a vacuum desiccator over $P_2O_5$.
Yield: 36% Melting point = 135° C.
Calculated: C, 45.9; H, 6.4; N, 26.8.
Found: C, 45.9; H, 6.8; N, 27.1.
IR-bands at 3280, 1740, 1715 and 1660 $cm^{-1}$.

EXAMPLE 7

A. Sodium D(-)-α-[(3-i-propyloxycarbonyl-imidazolidin-2-on-1-yl)-carbonylamino]-benzylpenicillin:

This penicillin was produced as described in Example 1A from 6.3 parts by weight of 3-(i-propyloxycarbonyl)-imidazolidin-2-on-1-carbonyl chloride and 10.9 parts by weight of ampicillin.
Yield: 62%
β-Lactam content: 85%
Calculated: C, 49.1; H, 5.1; N, 11.9; S, 5.5.
Found: C, 49.2; H, 6.2; N, 11.6; S, 5.6.
IR-bands at 3300, 1765, 1665, 1600 and 1260 $cm^{-1}$.
NMR-signals at $\tau+$ 2.3–2.8 (5H), 4.3 (1H), 4.5 (2H), 4.5–5.1 (1H), 5.8 (1H), 6.1 (4H), 8.4 (6H) and 8.6 ppm (6H).
Activity in animal experiments: B, C, and D.
Activity against *E. coli* 183/58: <1
Activity against *Proteus morg.* 932: 4
Activity against *Psdm. aerug.* Walter: 8
Activity against Klebsiella K 10: 4

B. 3-(i-Propyloxycarbonyl)-imidazolidin-2-on-1-carbonyl chloride:

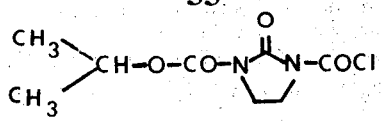

This carbamic acid chloride was produced as described in Example 1B from 11 parts by weight of N-i-propyloxycarbonyl-imidazolidone-2, 13.5 parts by weight of trimethylchlorosilane and 7 parts by weight of phosgene. Recrystallization from acetone/pentane.

Yield: 6.8 parts by weight. Melting point = 98°–102° C.

According to the NMR-spectrum and the analysis, the substance consisted of 65% of end product and 35% of starting material, which however did not interfere with the reaction to give the penicillin.

Calculated for 65% of end product and 35% of starting material:
C, 43.7; H, 5.5; Cl, 9.9; N, 13.5.
Found: C, 44.3; H, 5.5; Cl, 10.1; N, 14.5.
IR-bands at 3220, 1820, 1760, 1940, 1695 and 1685 cm$^{-1}$.
NMR-signals at $\tau$ = 4.85, 6.1 and 8.6 ppm (end product) and at $\tau$ = 4.9, 6.4 and 8.7 ppm (starting material)

C. N-(i-propyloxycarbonyl)-imidazolid-2-one

14.9 parts by weight of N-chlorocarbonylimidazolid-2-one in 100 parts by volume of i-propanol and 100 parts by volume of dioxane were warmed to 50° C for 3 hours. After stripping off the solvent, the residue was recrystallized from acetone.

Yield: 67% Melting point = 86° C
IR-bands at 3320, 1764 and 1670 cm$^{-1}$.
NMR-signals at $\tau$ = 5.05 (1H), 5.7–6.75 (5H) and 8.75 ppm (6H).

EXAMPLE 8

A. Sodium D(-)-α-[(3-pyrrolidyl-N-carbonyl-imidazolidin-2-on-1-yl)-carbonylamino]-benzylpenicillin

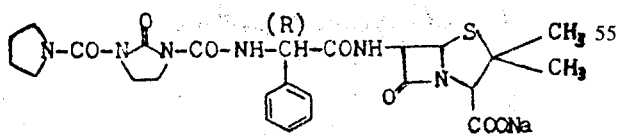

This penicillin was produced as described in Example 1A from 8 parts by weight of 3-pyrrolidyl-N-carbonyl-imidazolidin-2-on-1-carbonyl chloride and 13.2 parts by weight of ampicillin.

Yield: 82%
β-Lactam content: 95%
Calculated: C, 49.2; H, 5.3; N, 13.8.
Found: C, 49.3; H (7.1); N, 13.4.

IR-bands at 3290, 1760, 1720, 1655, 1600 and 1250 cm$^{-1}$.
NMR-signals at $\tau$-2.4–2.8 (5H), 4.4 (1H), 4.55 (2h), 5.8 (1H), 6.2 (4H), 6.3–6.6 (4H), 7.9–8.3 (4H), 8.45 (3H) and 8.5 ppm (3H)
Activity in animal experiments: A, B and C
Activity against E. coli 183/58: 4
Activity against Proteus 1017: 32
Activity against Psdm. aerug. Walter: 32
Activity against Klebsiella K 10: 8

B. 3-(Pyrrolidyl-N-carbonyl)-imidazolidin-2-on-1-carbonylchloride

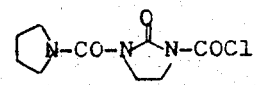

This carbamic acid chloride was produced as described in Example 1B from 9.2 parts by weight of N-(pyrrolidyl-N-carbonyl)-imidazolidone-2, 13.6 parts by weight of trimethylchlorosilane and 5.6 parts by weight of phosgene. Recrystallization from acetone/ether.

Yield: 1st fraction of melting point = 125° C: 71%
2nd fraction of melting point = 120°–122° C: 25%
1st fraction: Calculated - C, 44.0; H, 4.9; Cl, 14.5; N, 17.1.
Found - C, 44.1; H, 5.3; Cl, 15.0; N, 16.8.
IR-bands at 1795, 1755, 1725 and 1660 cm$^{-1}$.

C. N-(pyrrolidyl-N-carbonyl-imidazolid-2-one

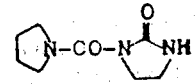

This substance was produced as described in Example 6C from N-chlorocarbonyl-imidazolidone-2 and pyrrolidine.

Yield: 56% Melting point = 155° C.
Calculated: C, 52.3; H, 7.1, N, 22.9.
Found: C, 51.5; H, 7.0; N, 22.6.
IR-bands at 3240, 1720, 1698, 1647 and 1620 cm$^{-1}$.
NMR-signals at $\tau$ = 6.0–6.8 (8H) and 8.0–8.3 (4H).

EXAMPLE 9

A. Sodium D(-)-α-[(3-piperdyl-N-carbonyl-imidazolidin-2-on-1-yl)-carbonylamino]-benzylpenicillin

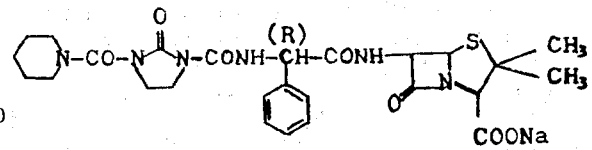

This penicillin was manufactured in the manner described in Example 1 A from 5.0 parts by weight of 3-(piperidyl-N-carbonyl)-imidazolidin-2-on-1-carbonyl chloride and 7.6 parts by weight of ampicillin.

Yield: 92%
β-Lactam content: 94%

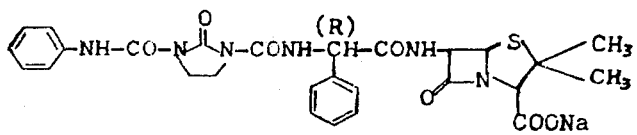

Calculated: C, 51.0; H, 5.4; N, 13.7; S, 5.2.
Found: C, 50.7; H(6.8); N, 13.5; S, 5.7.
IR-bands at 3295, 3050, 1765, 1725, 1667, 1608 and 1265 cm⁻¹.
NMR-signals at τ = 2.3–2.7 (5H), 4.3 (1H), 4.65 (2H), 5.8 (1H), 6.2 (4H), 6.3–6.6 (4H) and 8.1–8.5 ppm (12H).
Activity in animal experiments: B and C
Activity against *E. coli* 183/58: 4
Activity against Proteus 1017: 32
Activity against *Psdm. aerug.* Walter: 32
Activity against Klebsiella K 10: 4

B.
3-(Piperidyl-N-carbonyl)-imidazolidin-2-on-1-carbonyl chloride

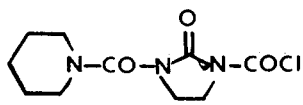

This carbamic acid chloride was produced as described in Example 1 B from 15.7 parts by weight of N-(piperidyl-N-carbonyl)-imidazolidone-2, 21.7 parts by weight of trimethylchlorosilane and 8.4 parts by weight of phosgene. Recrystallization from acetone/ether.
Yield: 1st fraction of melting point = 117°C : 27.5%
2nd fraction of melting point = 112°C : 49%
1st fraction:
Calculated: C, 46.3; H, 5.4; Cl 13.7; N, 16.2.
Found: C, 46.3; H, 5.8; Cl 14.6; N, 15.8.
IR-bands at 3060, 1793, 1710, 1659 and 1234 cm⁻¹.

C. N-(piperidyl-N-carbonyl)-imidazolid-2-one

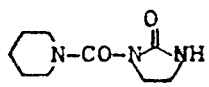

This substance was produced as described in Example 6 C from N-chlorocarbonyl-imidazolid-2-one and piperidine. Recrystallization from nitromethane.
Yield: 85% Melting point = 187°C
Calculated: C, 54.8; H, 7.6; N, 21.3.
Found: C, 55.2; H, 7.8; N, 20.3.
IR-bands at 3240, 1710, 1675 and 1640 cm⁻¹.
NMR-signals at τ = 6.0–7.0 (8H) and 8.0–8.6 ppm (6H).

EXAMPLE 10

A. Sodium D(-)-α-[3-phenylaminocarbonyl-imidazolidin-2-on-1-yl)-carbonylamino]-benzylpenicillin This penicillin was produced as described in Example 1 A from 2.4 parts by weight of 3-(phenylaminocarbonyl)-imidazolidin-2-on-1-carbonyl chloride and 4.4 parts by weight of ampicillin.
Yield: 54%
β-Lactam content: 86%
Calculated: C, 50.9; H, 4.9; N, 13.2; S, 5.0.
Found C, 51.3; H, 5.5 N, 12.2; S, 5.2.
IR-bands at 3390, 3290, 1782, 1720, 1678 and 1598 cm⁻¹.
NMR-signals a τ = 2.3–3.0 (10H), 4.4 (LH), 4.5 (2H), 5.8 (1H), 6.1 (4H), 8.4 (3H) and 8.5 ppm (3H).
Activity in animal experiments: B and C
Activity against *E. coli* 183/58: 4
Activity against *Proteus morg.* 932;: 4
Activity against Klebsiella K 10: 8

B.
3-(Phenylaminocarbonyl)-imidazolidin-2-on-1-carbonyl chloride

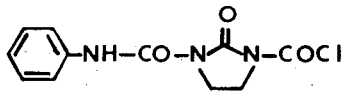

This carbamic acid chloride was produced as described in Example 1 B from 15.0 parts by weight of N-phenylaminocarbonyl-imidazolid-2-one, 15.8 parts by weight of trimethylchlorosilane and 7.2 parts by weight of phosgene.
Recrystallization from acetone/pentane.
Yield: 12% Melting point = 198°–200°C.
A further precipitate of 8.3 parts by weight was considerably less pure.
IR-bands at 3240, 1785, 1715, 1690 and 1598 cm⁻¹.

C. N-phenylaminocarbonyl-imidazolid-2-one

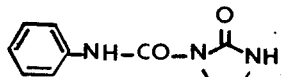

10.2 parts by weight of aniline were first introduced into 120 parts by volume of 80% strength aqueous tetrahydrofurane at pH = 8 and 14.9 parts by weight of N-chlorocarbonyl-imidazolid-2-one were added in portions at room temperature while stirring and keeping the pH value at 7–8 by simultaneous addition of triethylamine. The mixture was further stirred until the pH was constant, 80 parts by volume of water were added, the tetrahydrofurane was stripped off in vacuo, the pH was adjusted to 2.5 and after standing for one hour in an ice bath the product which had precipitated was filtered off. It was washed with ice water and dried over P₂O₅ in a vacuum desiccator.

Yield: 91% Melting point = 164°C

Recrystallization from acetone gave a product also melting at 164°C, in a yield of 78%.

Calculated: C, 58.5; H, 5.4; N, 20.5.
Found: C, 59.0; H, 5.4; N, 20.7.

IR-bands at 3275, 3090, 1735-1715, 1658, 1616 and 1600 cm⁻¹.

EXAMPLE 11

A. Sodium D(-)-α-[(3-phenoxycarbonyl-imidazolidin-2-on-1-yl)-carbonylamino]-benzylpenicillin

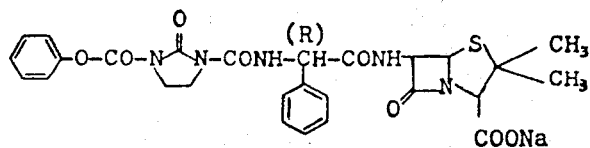

This penicillin was produced as described in Example 1 A from 5 parts by weight of 3-phenoxycarbonyl-imidazolidin-2-on-1-carbonyl chloride and 8.1 parts by weight of ampicillin.

Yield: 42%

β-Lactam content: 88% (determined from the analytical Craig distribution chromatogram)

Calculated: C, 53.7; H, 4.3; N, 11.6; S, 5.3.
Found: C, 53.5; H(5.8); N, 11.1; S, 5.4.

IR-bands at 3300, 3050, 1775, 1740 (shoulder), 1670, 1600 and 1198 cm⁻¹.

NMR-signals at τ = 2.3-2.9 (10H), 4.3 (1H), 4.5 (2H), 5.8 (1H), 6.05 Z(4H), 8.4 (3H) and 8.5 ppm (3H).

Activity in animal experiments: B and C
Activity against *E. coli* 183/58: <1
Activity against *Prot. morg.* 932: 8
Activity against *Psdm. aerug.* Walter: 16
Activity against Klebsiella K 10: 4

B. 3-Phenoxycarbonyl-imidazolidin-2-on-1-carbonyl chloride

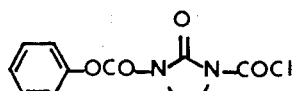

This carbamic acid chloride was produced as described in Example 1 B from 11 parts by weight of N-phenoxycarbonyl-imidazolidone-2, 11.7 parts by weight of trimethylchlorosilane and 5.3 parts by weight of phosgene. Recrystallization from acetone/pentane.

Yield: 21% Melting point approx. 130°C

IR-bands at 1780, 1758, 1682 and 1594 cm⁻¹.

C. N-phenoxycarbonyl-imidazolid-2-on:

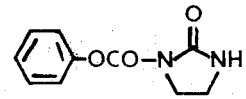

12.7 parts by weight of sodium phenolate were dissolved in 120 parts by volume of 80% strength tetrahydrofurane and the solution was adjusted to pH=8. 14.9 parts by weight of N-chlorocarbonyl-imidazolid-2-one were now introduced while stirring and keeping the pH value constant at 8 by simultaneous addition of triethylamine. The mixture was further stirred until the pH remained constant even without addition of triethylamine. 100 parts by volume of water were now added, the tetrahydrofurane was stripped off in vacuo, the residue was adjusted to pH = 10 with sodium hydroxide solution, and the solution was extracted with ethyl acetate. The organic solution was washed with water, dried over MgSO₄ and evaporated and the residue was dried under an oil pump at 60°C for 1 hour and recrystallized from acetone.

Yield: 56% Melting point = 182°C

Calculated: C, 58.3; H, 4.9; N, 13.6.
Found: C, 58.5; H, 5.1; N, 13.6.

IR-bands at 3260, 3110, 3050, 1780-1760, 1695, 1684, 1597 and 1182 cm⁻¹.

EXAMPLE 12

A. Sodium D(-)-α-[(3-benzoyl-imidazolidin-2-on-1-yl)-carbonylamino]-benzylpenicillin:

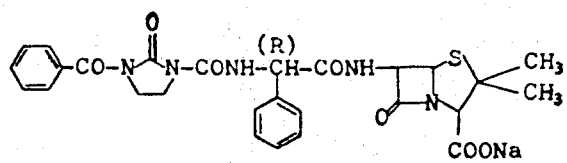

This penicillin was produced as described in Example 1 A from 5.5 parts by weight of 3-benzoyl-imidazolidin-2-on-1-carbonyl chloride and 10.1 parts by weight of ampicillin.

Yield: 92%

β-Lactam content: 89%

Calculated: C, 49.2; H, 5.2; N, 10.8; S, 4.9.
Found: C, 49.2; H, 5.3; N, 10.8; S, 5.2.

IR-bands at 3220, 3050, 1755, 1725 and 1667 cm⁻¹.

NMR-signals at τ = 2.2-2.8 (10H), 4.4 (1H), 4.55 (2H), 5.85 (1H), 6.05 (4H), 8.4 (3H) and 8.5 ppm (3H).

B. 3-Benzoyl-imidazolidin-2-on-1-carbonyl chloride:

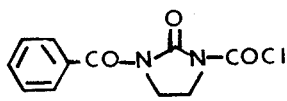

This carbamic acid chloride was produced as described in Example 1 B from 4.8 parts by weight of N-benzoylimidazolid-2-one, 4.4 parts by weight of trimethylchlorosilane and 2.8 parts by weight of phosgene.

Yield: 100% Melting point = 153°–4°C
Calculated: C, 52.2; H, 3.6; Cl, 14.0; N, 11.1.
Found: C, 51.2; H, 4.4; Cl, 13.2; N, 11.1.
IR-bands at 3060, 1768, 1725 and 1672 and cm⁻¹.
NMR-signals at $\tau = 2.5$ (5H) and 6.0 ppm (4H).

C. N-benzoyl-imidazolid-2-one

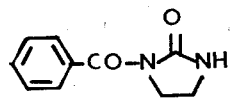

8.6 parts by weight of imidazolid-2-one in 100 parts by volume of dry tetrahydrofurane were treated with 15.5 parts by weight of benzoyl chloride in 30 parts by volume of tetrahydrofurane over the course of 15 minutes, at 5°–10°C, and the mixture was subsequently stirred for 3 hours at 10°C. The solvent was stripped off, the residue was shaken with a mixture of chloroform and aqueous NaHCO₃ solution for 15 minutes, the chloroform was separated off, the water was again extracted with chloroform and the combined organic phases were washed with water, dried over MgSO₄ and evaporated. The residue was recrystallized from ethyl acetate/ether.

Yield: 30% Melting point = 169°–70°C
Calculated: C, 63.2; H, 5.3; N, 14.8.
Found: C, 63.0; H, 5.3; N, 14.8.
IR-bands at 3190, 3110, 1742, 1718 and 1655 cm⁻¹.
NMR-signals at $\tau = 2.2–2.9$ (5H), 3.9 (1H), 6.0 (2H) and 6.6 ppm (2H).

EXAMPLE 13

A. Sodium D(-)-α-[(3-furoyl(2)-imidazolidin-2-on-1-yl)-carbonylamino]-benzylpenicillin

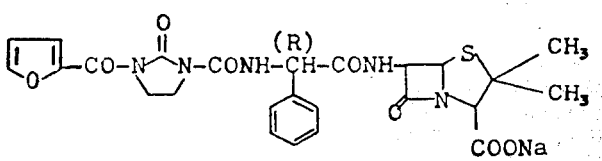

This penicillin was produced as described in Example 1 A from 6.0 parts by weight of 3-furoyl(2)-imidazolidin-2-on-1-carbonyl chloride and 12.1 parts by weight of ampicillin.

Yield: 90% β-Lactam content: 97%
Calculated: C, 50.0; H, 4.4; N, 11.6; S, 5.3.
Found: C, 49.9; H, 4.9; N, 11.1; S, 6.1.
IR-bands at 3300, 1770 (shoulder), 1740, 1670, 1605 and 1260 cm⁻¹.
NMR-signals at $\tau = 2.2$ (1H), 2.3–2.8 (6H), 3.4 (1H), 4.35 (1H), 4.55 (2H), 5.8 (1H), 6.1 (4H), 8.45 (3H) and 8.5 ppm (3H).

B. 3-Furoyl(2)-imidazolidin-2-on-1-carbonyl chloride

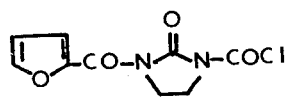

This carbamic acid chloride was produced as described in Example 1 B from 9 parts by weight of N-furoyl(2)-imidazolid-2-one, 8.7 parts by weight of trimethyl-chlorosilane and 6.0 parts by weight of phosgene.

Recrystallization from benzene.
Yield: 55% Melting point = 119°C
Calculated: C, 44.5; H, 2.9; Cl, 14.6; N, 11.5.
Found: C, 45.0; H, 3.6; Cl, 13.4; N, 11.5.
IR-bands at 3150, 3100, 1800, 1745, 1715, 1650, 1620 and 1255 cm⁻¹.
NMR-signals at $\tau = 2.3$ (1H), 2.5 (1H), 3.4 (1H) and 5.9 ppm (4H).

C. N-furoyl(2)-imidazolid-2-one

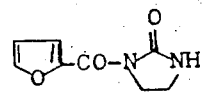

This substance was produced as described in Example 12 C from imidazolid-2-one and furane-α-carboxylic acid chloride. Instead of stirring at 10°C, the mixture was stirred for a further 3 hours at 30°–40°C. Recrystallization from nitromethane.

Yield: 53% Melting point = 144°–6°C
Calculated: C, 53.2; H, 4.5; N, 15.6.
Found: C, 51.2; H, 4.5; N, 15.3.
IR-bands at 3245, 3120, 1740, 1622, 1560, 1257 and 1240 cm⁻¹.
NMR-signals at $\tau = 2.25$ (1H), 2.6 (1H), 3.35 (1H), 6.0 (2H) and 6.4 ppm (2H).

EXAMPLE 14

A. Sodium D(-)-α-[(3-n-butyryl-imidazolidin-2-on-1-yl)-carbonylamino]-benzylpenicillin

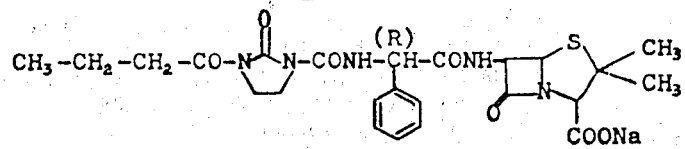

This penicillin was produced as described in Example 1 A from 6.0 parts by weight of 3n-butyryl-imidazolidin-2-on-1-carbonyl chloride and 11.3 parts by weight of ampicillin.

Yield: 100%
β-Lactam content: 93.5%.
Calculated: C, 50.5; H, 5.3; N, 12.2; S, 5.6.
Found: C, 50.1; H, 6.0; N, 11.8; S, 6.7.
IR-bands at 3310, 3055, 1760, 1730, 1680, 1603, 1265 and 1230 cm⁻¹.
NMR-signals at $\tau$ = 2.3–2.8 (5H), 4.4 (1H), 4.5 (2H), 5.8 (1H), 6.25 (4H), 7.1 (2H), 8.2 (2H), 8.4 (3H), 8.5 (3H) and 9.0 ppm (3H).

B. 3-n-Butyryl-imidazolidin-2-on-1-carbonyl chloride

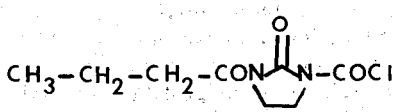

This carbamic acid chloride was produced as described in Example 1 B from 10.0 parts by weight of N-n-butyryl-imidazolid-2-one, 11.4 parts by weight of trimethylchlorosilane and 7.0 parts by weight of phosgene. It was twice recrystallized from acetone/pentane.

Yield: 65% Melting point = 103°C
Calculated: C, 40.2; H, 4.4; Cl, 14.9; N, 11.8;
Found: C, 40.2; H, 4.8; Cl, 14.7; N, 11.7;
IR-bands at 3060, 1792, 1722, 1686 and 1220 cm⁻¹.
NMR-signals at $\tau$ = 6.0 (4H), 7.1 (2H), 8.4 (2H) and 9.0 ppm (3H).

C. N-n-butyryl-imidazolid-2-one

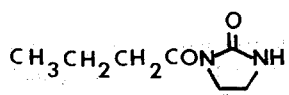

This substance was produced as described in Example 12 C from imidazolidone-2 and n-butyryl chloride. Instead of stirring at 10°C, the mixture was stirred for a further hour at room temperature and an hour at 50°C. Recrystallize twice from methanol.

Yield: 36% Melting point = 96°C
Calculated: C, 53.9; H, 7.7; N, 18.0.
Found: C, 53.5; H, 7.6; N, 18.3.
IR-bands at 3200, 3120, 1740, 1662 and 1262 cm⁻¹.
NMR-signals at $\tau$ = 6.15 (2H), 6.5 (2H), 7.2 (2H), 8.4 (2H) and 9.1 ppm (3H).

EXAMPLE 15

If, as described in Example 1 A, 0.05 mol of:
3-acetyl-imidazolidin-2-on-1-carbonyl chloride,
3-methylaminocarbonyl-imidazolidin-2-on-1-carbonyl chloride,
3-methoxycarbonyl-imidazolidin-2-on-1-carbonyl chloride,
3-methylsulphonyl-imidazolidin-2-on-1-carbonyl chloride,
3-aminocarbonyl-imidazolidin-2-on-1-carbonyl chloride,
3-phenoxycarbonyl-imidazolidin-2-on-1-carbonyl chloride,
3-furoyl(2)-imidazolidin-2-on-1-carbonyl chloride or 3-ethyl-sulphonyl-imidazolidin-2-on-1-carbonyl chloride are reacted with 0.05 mol of:
α-amino-p-methylbenzylpenicillin,
α-amino-p-methoxybenzylpenicillin,
α-amino-p-methylthiobenzylpenicillin,
α-amino-p-hydroxybenzylpenicillin,
α-amino-p-chlorobenzylpenicillin,
α-amino-p-nitrobenzylpenicillin,
α-amino-α-thienyl(2)-methylpenicillin or
α-amino-α-thienyl(3)-methylpenicillin,
the following penicillins are obtained in the form of their sodium salts:
α-[(3-acetyl-imidazolidin-2-on-1-yl)-carbonylamino]-p-methylbenzylpenicillin,
α-[(3-acetyl-imidazolidin-2-on-1-yl)-carbonylamino]-p-methoxybenzylpenicillin,
α-[(3-acetyl-imidazolidin-2-on-1-yl)-carbonylamino]-p-methylthiobenzylpenicillin,
α-[(3-acetyl-imidazolidin-2-on-1-yl)-carbonylamino]-p-hydroxybenzylpenicillin,
α-[(3-acetyl-imidazolidin-2-on-1-yl)-carbonylamino]-p-chlorobenzylpenicillin,
α-[(3-acetyl-imidazolidin-2-on-1-yl)-carbonylamino]-p-nitrobenzylpenicillin,
α-[(3-acetyl-imidazolidin-2-on-1-yl)-carbonylamino]-α-thienyl-(2)-methylpenicillin,
α-[(3-acetyl-imidazolidin-2-on-1-yl)-carbonylamino]-α-thienyl-(3)-methylpenicillin,
α-[(3-methoxycarbonyl-imidazolidin-2-on-1-yl)-carbonylamino]-p-methoxybenzylpenicillin,
α-[(3-methoxycarbonyl-imidazolidin-2-on-1-yl)-carbonylamino]-p-methylthiobenzylpenicillin,
α-[(3-methoxycarbonyl-imidazolidin-2-on-1-yl)-carbonylamino]-p-hydroxybenzylpenicillin,
α-[(3-methoxycarbonyl-imidazolidin-2-on-1-yl)-carbonylamino]-p-chlorobenzylpenicillin, α-[(3-methoxycarbonyl-imidazolidin-2-on-1-yl)-carbonylamino]-p-nitrobenzylpenicillin,
α-[(3-methoxycarbonyl-imidazolidin-2-on-1-yl)-carbonylamino]-α-thienyl(2)-methylpenicillin,
α-[(3-methoxycarbonyl-imidazolidin-2-on-1-yl)-carbonylamino]-α-thienyl(3)-methylpenicillin,
α[(-[-methylsulphonyl-imidazolidin-2-on-1-yl)-carbonylamino]-p-methylbenzylpenicillin,
α-[(3-methylsulphonyl-imidazolidin-2-on-1-yl)-carbonylamino]-p-methoxybenzylpenicillin,
α-[(3-methylsulphonyl-imidazolidin-2-on-1-yl)-carbonylamino]-p-methylthiobenzylpenicillin,
α-[(3-methylsulphonyl-imidazolidin-2-on-1-yl)-carbonylamino]-p-hydroxybenzylpenicillin,
α-[(3-methylsulphonyl-imidazolidin-2-on-1-yl)-carbonylamino]-p-chlorobenzylpenicillin,
α-[(3-methylsulphonyl-imidazolidin-2-on-1-yl)-carbonylamino]-p-nitrobenzylpenicillin,
α-[(3-methylsulphonyl-imidazolidin-2-on-1-yl)-carbonylamino]-α-thienyl(2)-methylpenicillin,
α-[(3-methylsulphonyl-imidazolidin-2-on-1-yl)-carbonylamino]-α-thienyl(3)-methylpenicillin,
α-[(3-aminocarbonyl-imidazolidin-2-on-1-yl)-carbonylamino]-p-methylbenzylpenicillin,
α-[(3-methylaminocarbonyl-imidazolidin-2-on-1-yl)-carbonylamino]-p-methylbenzylpenicillin,
α-[(3-methylaminocarbonyl-imidazolidin-2-on-1-yl)-carbonylamino]-p-methoxybenzylpenicillin,
α-[(3-methylaminocarbonyl-imidazolidin-2-on-1-yl)-carbonylamino]-p-methylthiobenzylpenicillin,
α-[(3-methylaminocarbonyl-imidazolidin-2-on-1-yl)-carbonylamino]-p-hydroxybenzylpenicillin,
α-[(3-methylaminocarbonyl-imidazolidin-2-on-1-yl)-carbonylamino]-p-chlorobenzylpenicillin,
α-[(3-methylaminocarbonyl-imidazolidin-2-on-1-yl)-carbonylamino]-p-nitrobenzylpenicillin,
α[(3-methylaminocarbonyl-imidazolidin-2-on-1-yl)-carbonylamino]-α-thienyl(2)-methylpenicillin,
α-[(3-methylaminocarbonyl-imidazolidin-2-on-1-yl)-carbonylamino]-α-thienyl(3)-methylpenicillin,
α-[(3-methoxycarbonyl-imidazolidin-2-on-1-yl)-carbonylamino]-p-methylbenzylpenicillin,
α-[(3-aminocarbonyl-imidazolidin-2-on-1-yl)-carbonylamino]-p-methoxybenzylpenicillin,
α-[(3-aminocarbonyl-imidazolidin-2-on-1-yl)-carbonylamino]-p-methylthiobenzylpenicillin,
α-[(3-aminocarbonyl-imidazolidin-2-on-1-yl)-carbonylamino]-p-hydroxybenzylpenicillin,
α-[(3-aminocarbonyl-imidazolidin-2-on-1-yl)-carbonylamino]-p-chlorobenzylpenicillin,
α-[(3-aminocarbonyl-imidazolidin-2-on-1-yl)-carbonylamino]-p-nitrobenzylpenicillin,
α-[(3-aminocarbonyl-imidazolidin-2-on-1-yl)-carbonylamino]-α-thienyl(2)-methylpenicillin,
α-[(3-aminocarbonyl-imidazolidin-2-on-1-yl)-carbonylamino]-α-thienyl(3)-methylpenicillin,
α-[(3-phenoxycarbonyl-imidazolidin-2-on-1-yl)-carbonylamino]-p-methylbenzylpenicillin,
α-[(3-phenoxycarbonyl-imidazolidin-2-on-1-yl)-carbonylamino]-p-methoxybenzylpenicillin,
α-[(3-phenoxycarbonyl-imidazolidin-2-on-1-yl)-carbonylamino]-p-methylthiobenzylpenicillin,
α-[(3-phenoxycarbonyl-imidazolidin-2-on-1-yl)-carbonylamino]-p-hydroxybenzylpenicillin,
α-[(3-phenoxycarbonyl-imidazolidin-2-on-1-yl)-carbonylamino]-p-chlorobenzylpenicillin,
α-[(3-(phenoxycarbonyl-imidazolidin-2-on-1-yl)-carbonylamino]-p-nitrobenzylpenicillin,
α-[(3-phenoxycarbonyl-imidazolidin-2-on-1-yl)-carbonylamino]-α-thienyl(2)-methylpenicillin,
α-[(3-phenoxycarbonyl-imidazolidin-2-on-1-yl)-carbonylamino]-α-thienyl(3)-methylpenicillin,
α-[(3-furoyl(2)-imidazolidin-2-on-1-yl)-carbonylamino]-p-methylbenzylpenicillin,
α-[(3-furoyl(2)-imidazolidin-2-on-1-yl)-carbonylamino]-p-methoxybenzylpenicillin,
α-[(3-furoyl(2)-imidazolidin-2-on-1-yl)-carbonylamino]-p-methylthiobenzylpenicillin,
α-[(3-furoyl(2)-imidazolidin-2-on-1-yl)-carbonylamino]-p-hydroxybenzylpenicillin,
α-[(3-furoyl(2)-imidazolidin-2-on-1-yl)-carbonylamino]-p-chlorobenzylpenicillin,
α-[(3-furoyl(2)-imidazolidin-2-on-1-yl)-carbonylamino]-p-nitrobenzylpenicillin,
α-[(3-furoyl(2)-imidazolidin-2-on-1-yl)-carbonylamino]-α-thienyl(2)-methylpenicillin,
α-[(3-furoyl(2)-imidazolidin-2-on-1-yl)-carbonylamino]-α-thienyl(3)-methylpenicillin,
α-[(3-ethylsulphonyl-imidazolidin-2-on-1-yl)-carbonylamino]-p-methylbenzylpenicillin,
α-[(3-ethylsulphonyl-imidazolidin-2-on-1-yl)-carbonylamino]-p-methoxybenzylpenicillin,
α-[(3-ethylsulphonyl-imidazolidin-2-on-1-yl)-carbonylamino]-p-methylthiobenzylpenicillin,
α-[(3-ethylsulphonyl-imidazolidin-2-on-1-yl)-carbonylamino]-p-hydroxybenzylpenicillin,
α-[(3-ethylsulphonyl-imidazolidin-2-on-1-yl)-carbonylamino]-p-chlorobenzylpenicillin,
α-[(3-ethylsulphonyl-imidazolidin-2-on-1-yl)-carbonylamino]-p-nitrobenzylpenicillin,
α-[(3-ethylsulphonyl-imidazolidin-2-on-1-yl)-carbonylamino]-α-thienyl(2)-methylpenicillin,
or α-[(3-ethylsulphonyl-imidazolidin-2-on-1-yl)-carbonylamino]-α-thienyl(3)-methylpenicillin.

EXAMPLE 16

If, as described in Example 1 A, 0.05 mol of:
1-chlorocarbonyl-1,3-dimethyl-3-acetyl-urea,
1-chlorocarbonyl-1,3-dimethyl-3-methylsulphonyl-urea,
1-chlorocarbonyl-1,3-dimethyl-3-methoxycarbonyl-urea,
N-(isothiazolidine-1,1-dioxide-2-yl-carbonyl)-N-methyl-carbamic acid chloride,
1-chlorocarbonyl-3-p-methoxybenzoyl-imidazolidone-(2),
1-chlorocarbonyl-3-methylsulphonyl-4-methyl-imidazolidone-(2),
1-chlorocarbonyl-3-methylsulphonyl-5-methyl-imidazolidone-(2),
1-chlorocarbonyl-1-methyl-3-methylsulphonyl-urea,
1-chlorocarbonyl-1,3-diaza-4-thia-cyclohexan-2-on-4,4-dioxide
or
1-chlorocarbonyl-4-thia-imidazolidin-2-on-4,4-dioxide are reacted with 0.05 mol of ampicillin,
the following penicillins are obtained in the form of their sodium salts:
D(−)-α-(5-acetyl-3,5-dimethyl-biureido)-benzylpenicillin,
D(−)-α-(5-methylsulphonyl-3,5-dimethyl-biureido)-benzylpenicillin,
D(−)-α-(5-methoxycarbonyl-3,5-dimethyl-biureido)-benzylpenicillin,
D(−)-α-[(3-(isothiazolidine-1,1-dioxide-2-yl-carbonyl)-3-methylureido]-benzylpenicillin, D(—)-α-[(3-(p-methoxybenzoyl-imidazolidin-2-on-1-yl)-carbonylamino]-benzylpenicillin,
D(—)-α-[(3-methylsulphonyl-4-methyl-imidazolidin-2-on-1-yl)-carbonylamino]-benzylpenicillin,
D(—)-α-[(3-methylsulphonyl-5-methyl-imidazolidin-2-on-1-yl)-carbonylamino]-benzylpenicillin,
D(—)-α-[(3-methyl-5-methylsulphonyl-biureido)-benzylpenicillin,
D(—)-α-(1,3-diaza-4-thia-cyclohexan-2-on-4,4-dioxide-1-yl-carbonylamino)-benzylpenicillin or
D(—)-α-(4-thia-imidazolidin-2-one-4,4-dioxide-1-yl-carbonylamino)-benzylpenicillin.

EXAMPLE 17

If, as described in Example 1A, 0.05 mol of:
N-benzoyl-N-methyl-carbamoylisocyanate,
N-benzoyl-N-methyl-carbamoylisothiocyanate,
N-acetyl-N-methyl-carbamoylisocyanate,
N-acetyl-N-methyl-carbamoylisothiocyanate,
imidazolid-2-on-1-yl-carbonylisocyanate,
imidazolid-2-on-1-yl-carbonylisothiocyanate,
pyrrolid-2-on-1-yl-carbonylisocyanate,
pyrrolid-2-on-1-yl-carbonylisothiocyanate,
1,3,3-trimethyl-ureido-1-carbonylisocyanate,
1,3,3-trimethyl-ureido-1-carbonylisothiocyanate,
N-methylsulphonyl-N-methyl-carbamoylisocyanate,
N-methylsulphonyl-N-methyl-carbamoylisothiocyanate,
1,3-dimethylureido-1-carbonylisocyanate,
1,3-dimethylureido-1-carbonylisothiocyanate,
N-furoyl(2)-N-methylcarbamoylisocyanate,
N-furoyl(2)-N-methylcarbamoylisothiocyanate,
isothiazolidine-1,1-dioxide-2-yl-carbonylisocyanate or isothiazolidine-1,1-dioxide-2-yl-carbonylisothiocyanate are reacted with 0.05 mol of ampicillin, the following penicillins are obtained in the form of their sodium salts:
D(—)-α-(5-benzoyl-5-methyl-biureido)-benzylpenicillin,
D(—)-α-(5-benzoyl-5-methyl-2-thio-biureido)-benzylpenicillin,
D(—)-α-(5-acetyl-5-methyl-biureido)-benzylpenicillin,
D(—)-α-(5-acetyl-5-methyl-2-thio-biureido)-benzylpenicillin,
D(—)-α-[3-imidazolidin-2-on-1-yl-carbonyl)-ureido]-benzylpenicillin,
D(—)-α-[3-(imidazolidin-2-on-1-yl-carbonyl)-thioureido]-benzylpenicillin,
D(—)-α-[3-(pyrrolidin-2-on-1-yl-carbonyl)-ureido]-benzylpenicillin,
D(—)-α-[3-(pyrrolidin-2-on-1-yl-carbonyl)-thioureido]-benzylpenicillin,
D(—)-α-[5-dimethylaminocarbonyl-5-methyl-biureido]-benzylpenicillin,
D(—)-α-[5-dimethylaminocarbonyl-5-methyl-2-thio-biureido]-benzylpenicillin,
D(—)-α-(5-methylsulphonyl-5-methyl-biureido)-benzylpenicillin,
D(—)-α-(5-methylsulphonyl-5-methyl-2-thio-biureido)-benzylpenicillin,
D(—)-α-(5-methylaminocarbonyl-5-methyl-biureido)-benzylpenicillin,
D(—)-α-(5-methylaminocarbonyl-5-methyl-2-thio-biureido)-benzylpenicillin,
D(—)-α-(5-furoyl(2)-5-methyl-biureido)-benzylpenicillin,
D(—)-α-(5-furoyl(2)-5-methyl-2-thio-biureido)-benzylpenicillin,
D(—)-α-[3-(isothiazolidine-1,1-dioxide-2-yl-carbonyl)-ureido]-benzylpencillin or
D(—)-α-[3-(isothiazolidine-1,1-dioxide-2-yl-carbonyl)-thioureido]-benzylpencillin.

EXAMPLE 18

If, as described in Example 1 A, 0.05 mol of:
1-chlorocarbonyl-3-propionyl-imidazolid-2-one,
1-chlorocarbonyl-3-acetyl-4-methyl-imidazolid-2-one,
1-chlorocarbonyl-3-acetyl-5-methyl-imidazolid-2-one,
1-chlorocarbonyl-3-acetyl-1,3-diaza-cyclohexan-2-one,
1-chlorocarbonyl-3-n-propylsulphonyl-imidazolid-2-one,
1-chlorocarbonyl-3-ethylsulphonyl-4-methyl-imidazolid-2-one,
1-chlorocarbonyl-3-ethylsulphonyl-5-methyl-imidazolid-2-one,
1-chlorocarbonyl-3-ethylsulphonyl-1,3-diaza-cyclohexan-2-one,
1-chlorocarbonyl-3-methylsulphonyl-1,3-diaza-cyclohexan-2-one,
1-chlorocarbonyl-3-n-propylsulphonyl-1,3-diaza-cyclohexan-2-one,
1-chlorocarbonyl-3-i-propylsulphonyl-1,3-diaza-cyclohexan-2-one,
1-chlorocarbonyl-3-i-propylsulphonyl-imidazolid-2-one,
1-chlorocarbonyl-3-i-propylsulphonyl-4-methyl-imidazolid-2-one,
1-chlorocarbonyl-3-i-propylsulphonyl-5-methyl-imidazolid-2-one,
1-chlorocarbonyl-3-n-propylsulphonyl-4-methyl-imidazolid-2-one,
1-chlorocarbonyl-3-n-propylsulphonyl-5-methyl-imidazolid-2-one,
1-chlorocarbonyl-3-phenylsulphonyl-imidazolid-2-one,
1-chlorocarbonyl-3-p-methylphenylsulphonyl-imidazolid-2-one,
1-chlorocarbonyl-3-cyclohexylsulphonyl-imidazolid-2-one,
1-chlorocarbonyl-3-thienyl(2)-sulphonyl-imidazolid-2-one,
1-chlorocarbonyl-3-formyl-4-methyl-imidazolid-2-one,
1-chlorocarbonyl-3-formyl-5-methyl-imidazolid-2-one,
1-chlorocarbonyl-3-formyl-1,3-diaza-cyclohexan-2-one,
1-chlorocarbonyl-3-methylaminocarbonyl-4-methyl-imidazolid-2-one,
1-chlorocarbonyl-3-methylaminocarbonyl-5-methyl-imidazolid-2-one,
1-chlorocarbonyl-3-methylaminocarbonyl-1,3-diaza-cyclohexan-2-one,
1-chlorocarbonyl-3-methoxycarbonyl-4-methyl-imidazolid-2-one,
1-chlorocarbonyl-3-methoxycarbonyl-5-methyl-imidazolid-2-one,
1-chlorocarbonyl-3-methoxycarbonyl-1,3-diaza-cyclohexan-2-one,
1-chlorocarbonyl-3-i-propyloxycarbonyl-4-methyl-imidazolid-2-one, 1-chlorocarbonyl-3-i-propyloxycarbonyl-5-methyl-imidazolid-2-one,
1-chlorocarbonyl-3-i-propyloxycarbonyl-1,3-diaza-cyclohexan-2-one,
1-chlorocarbonyl-3-methylsulphonyl-4,5-dimethyl-imidazolid-2-one,
1-chlorocarbonyl-3-methylsulphonyl-4,4-dimethyl-imidazolid-2-one, or
1-chlorocarbonyl-3-methylsulphonyl-5,5-dimethyl-imidazolid-2-one are reacted with 0.05 mol of ampicillin, the following penicillins are obtained in the form of their sodium salts:

D(—)-α-[(3-propionyl-imidazolidin-2-on-1-yl)-carbonylamino]-benzylpenicillin,
D(—)-α-[(3-acetyl-4-methyl-imidazolidin-2-on-1-yl)-carbonylamino]-benzylpenicillin,
D(—)-α-[(3-acetyl-5-methyl-imidazolidin-2-on-1-yl)-carbonylamino]-benzylpenicillin,
D(—)-α-[(3-acetyl-1,3-diaza-cyclohexan-2-on-1-yl)-carbonylamino]-benzylpenicillin,
D(—)-α-[(3-n-propylsulphonyl-imidazolidin-2-on-1-yl)-carbonylamino]-benzylpenicillin,
D(—)-α-[(3-ethylsulphonyl-4-methyl-imidazolidin-2-on-1-yl)-carbonylamino]-benzylpenicillin,
D(—)-α-[(3-ethylsulphonyl-5-methyl-imidazolidin-2-on-1-yl)-carbonylamino]-benzylpenicillin,
D(—)-α-[(3-ethylsulphonyl-1,3-diaza-cyclohexan-2-on-1-yl)-carbonylamino]-benzylpenicillin,
D(—)-α-[(3-methylsulphonyl-1,3-diaza-cyclohexan-2-on-1-yl)-carbonylamino]-benzylpenicillin,
D(—)-α-[(3-n-propylsulphonyl-1,3-diaza-cyclohexan-2-on-1-yl)-carbonylamino]-benzylpenicillin,
D(—)-α-[(3-i-propylsulphonyl-1,3-diaza-cyclohexan-2-on-1-yl)-carbonylamino]-benzylpenicillin,
D(—)-α-[(3-i-propylsulphonyl-imidazolidin-2-on-1-yl)-carbonylamino]-benzylpenicillin,
D(—)-α-[(3-i-propylsulphonyl-4-methyl-imidazolidin-2-on-1-yl)-carbonylamino]-benzylpenicillin,
D(—)-α-[(3-i-propylsulphonyl-5-methyl-imidazolidin-2-on-1-yl)-carbonylamino]-benzylpenicillin,
D(—)-α-[(3-n-propylsulphonyl-4-methyl-imidazolidin-2-on-1-yl)-carbonylamino]-benzylpenicillin,
D(—)-α-[(3-n-propylsulphonyl-5-methyl-imidazolidin-2-on-1-yl)-carbonylamino]-benzylpenicillin,
D(—)-α-[(3-phenylsulphonyl-imidazolidin-2-on-1-yl)-carbonylamino]-benzylpenicillin,
D(—)-α-[(3-p-methylphenylsulphonyl-imidazolidin-2-on-1-yl)-carbonylamino]-benzylpenicillin,
D(—)-α-[(3-cyclohexylsulphonyl-imidazolidin-2-on-1-yl)-carbonylamino]-benzylpenicillin,
D(—)-α-[(3-thienyl(2)-sulphonyl-imidazolidin-2-on-1-yl)-carbonylamino]-benzylpenicillin,
D(—)-α-[(3-formyl-4-methyl-imidazolidin-2-on-1-yl)-carbonylamino]-benzylpenicillin,
D(—)-α-[(3-formyl-5-methyl-imidazolidin-2-on-1-yl)-carbonylamino]-benzylpenicillin,
D(—)-α-[(3-formyl-1,3-diaza-cyclohexan-2-on-1-yl)-carbonylamino]-benzylpenicillin,
D(—)-α-[(3-methylaminocarbonyl-4-methyl-imidazolidin-2-on-1-yl)-carbonylamino]-benzylpenicillin,
D(—)-α-[(3-methylaminocarbonyl-5-methyl-imidazolidin-2-on-1-yl)-carbonylamino]-benzylpenicillin,
D(—)-α-[(3-methylaminocarbonyl-1,3-diaza-cyclohexan-2-on-1-yl)-carbonylamino]-benzylpenicillin,
D(—)-α-[(3-methoxycarbonyl-4-methyl-imidazolidin-2-on-1-yl)-carbonylamino]-benzylpenicillin,
D(—)-α-[(3-methoxycarbonyl-5-methyl-imidazolidin-2-on-1-yl)-carbonylamino]-benzylpenicillin,
D(—)-α-[(3-methoxycarbonyl-1,3-diaza-cyclohexan-2-on-1-yl)-carbonylamino]-benzylpenicillin,
D(—)-α-[(3-i-propyloxycarbonyl-4-methyl-imidazolidin-2-on-1-yl)-carbonylamino]-benzylpenicillin,
D(—)-α-[(3-i-propyloxycarbonyl-5-methyl-imidazolidin-2-on-1-yl)-carbonylamino]-benzylpenicillin,
D(—)-α-[(3-i-propyloxycarbonyl-1,3-diaza-cyclohexan-2-on-1-yl)-carbonylamino]-benzylpenicillin,
D(—)-α-[(3-methylsulphonyl-4,5-dimethyl-imidazolidin-2-on-1-yl)-carbonylamino]-benzylpenicillin,
D(—)-α-[(3-methylsulphonyl-4,4-dimethyl-imidazolidin-2-on-1-yl)-carbonylamino]-benzylpenicillin or
D(—)-α-[(3-methylsulphonyl-5,5-dimethyl-imidazolidin-2-on-1-yl)-carbonylamino]-benzylpenicillin.

EXAMPLE 19

A. Sodium D(—)-α-[(2-methylsulphonylamino-imidazolin(2)-1-yl)-carbonylamino]-benzylpenicillin:

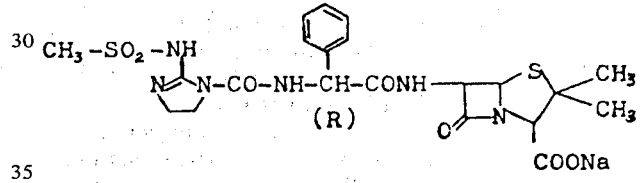

This penicillin was produced as described in Example 1 A from 4.8 parts by weight of 1-chlorocarbonyl-2-methyl-sulphonylamino-4,5-dihydroimidazole and 9 parts by weight of ampicillin.
Yield: 38%
β-Lactam content: 96%
IR-bands at 3060, 1764, 1670, 1605 and 1130 cm⁻¹.
NMR-signals at τ = 2.3–2.9 (5H), 4.45 (1H), 4.55 (2H), 5.8 (1H), 5.9–6.5 (4H), 6.95 (3H), 8.4 (3H) and 8.5 ppm (3H).
Activity against *E. coli* C 165: 8
Activity against *Prot. vulg.* 1017: 16

B.
1-Chlorocarbonyl-2-methylsulphonylamino-4,5-dihydroimidazole:

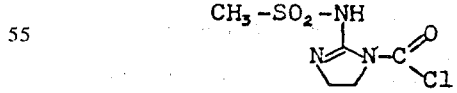

8.2 parts by weight of 2-(N-methylsulphonyl-imino)-imidazoline and 8.0 parts by weight of phosgene were reacted in anhydrous dioxane at 60°–70°C. The resulting crude product however, on reaction with ampicillin, gave the penicillin of the expected structure.

EXAMPLE 20

Sodium D(—)-α-[(3-formyl-imidazolidin-2-on-1-yl)-carbonylamino]-benzylpenicillin:

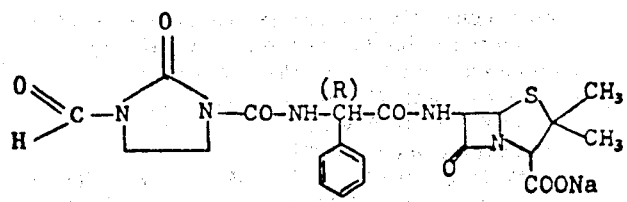

D(−)-α-aminobenzylpenicillin (5.7 parts by weight) was suspended in 80% strength aqueous tetrahydrofurane (60 parts by volume) and sufficient triethylamine was then added dropwise at 30°C, while stirring, just to produce a clear solution and to give a pH value of the mixture of between 7.5 and 8.2 (glass electrode). The mixture was then cooled to 0°C and a solution of 3-formyl-imidazolidin-2-one-1-carbonyl chloride (2.2 parts by weight) in tetrahydrofurane (20 parts by volume) was added dropwise. At the same time the pH of the mixture was kept at 7.5 to 8.0 by appropriate addition of triethylamine. The mixture was stirred for a further 30 minutes at 0°C. Thereafter, no further addition of triethylamine was necessary to maintain the pH value of 7.5 to 8.0. After addition of water (60 parts by volume) the pH was adjusted to 6.5 with dilute hydrochloric acid and the tetrahydrofurane was largely removed in a rotary evaporator. The aqueous solution which remained was once extracted by shaking with ether (the ether extract was discarded) and was subsequently covered with a 1:1 mixture (vol:vol) of ether and ethyl acetate and the pH was adjusted to 1–2 by means of dilute hydrochloric acid while stirring and cooling with ice. The organic phase was then separated off, washed with water, dried for about one hour over magnesium sulphate at 0°C and, after filtration, diluted with about half its volume of ether. The sodium salt was then precipitated by adding an approximate 1 molar solution of sodium 2-ethylhexanoate in ether containing methanol. The precipitate was initially oily but could be converted into an amorphous solid substance after decanting off the supernatant solution and triturating with ether.

Yield: 0.9 parts by weight (crude product)
β-Lactam content: 77%

According to the NMR-spectrum, the substance contained 3.5 mols of H₂O and 0.3 mol of sodium 2-ethylhexanoate per mol. This was taken into account in the calculated values of the analytical data:

Calculated: C, 45.1; H, 5.4; N, 11.2; S, 5.1.
Found: C, 45.2; H, 5.3; N, 11.0; S, 5.3.
NMR-signals at τ = 1.0 (1H), 2.4–2.8 (5H), 4.3–4.6 (3H), 5.8 (1H), 6.1–6.3 (4H) and 8.3–8.5 ppm (6H)

Activity against *E. coli* C 165: 8
Activity against *Prot. morg.* 932: 8
Activity against Psdm. F 41: 8
Activity against Klebs. K 10: 32

The 3-formyl-imidazolidin-2-on-1-carbonyl chloride used in the production of this penicillin was obtained as follows:

N-formyl-imidazolidin-2-one:

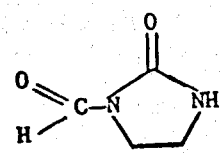

Imidazolidin-2-one (8.6 parts by weight) was suspended in tetrahydrofurane (100 parts by volume), formic acid-acetic acid anhydride (10 parts by weight) was added at room temperature while stirring and thereafter the mixture was stirred at the same temperature for 3¼ hours. The precipitate present was filtered off, washed with tetrahydrofurane and dried.

Yield: 6.4 parts by weight
Melting point: 156°–159°C
Calculated: C, 42.1; H, 5.3; N, 24.6.
Found: C, 42.2; H, 5.6; N, 25.3.
NMR-signals at τ = 1.2 (1H) and 5.9 to 6.5 ppm (4H).

3-Formyl-imidazolidin-2-on-1-carbonyl chloride

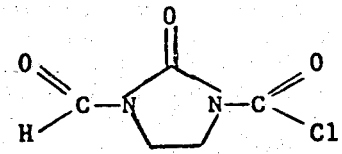

A mixture of N-formyl-imidazolidin-2-one (6.0 parts by weight), benzene (40 parts by volume) and triethylamine (11.8 parts by volume) was boiled under reflux and at the same time a solution of trimethylchlorosilane (8.5 parts by weight) in benzene (20 parts by volume) was added dropwise. Thereafter the mixture was boiled for a further 5 hours and then left to stand overnight at room temperature and the precipitate present was filtered off and washed with benzene. The combined benzene solutions, on standing overnight, formed further amounts of precipitate which were filtered off. A solution of phosgene (15.6 parts by weight) in dichloromethane (30 parts by volume) was then added dropwise to the filtrate and the mixture was subsequently left to stand overnight in a refrigerator. It was then completely evaporated to dryness in a rotary evaporator. The residue, a mass which did not crystallize throughout to give a solid, was used, as it was, for the reaction with ampicillin.

EXAMPLE 21

Sodium D(−)-α-[(3-pivaloyl-imidazolidin-2-on-1-yl)-carbonylamino]-benzylpenicillin:

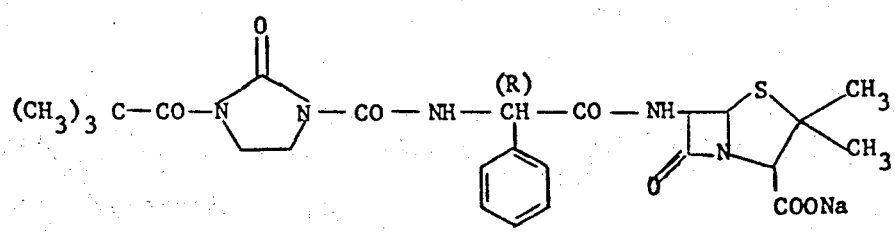

This penicillin was produced as described in Example 20 from ampicillin (9.8 parts by weight) and 3-pivaloylimidazolidin-2-on-1-carbonyl chloride (4.9 parts by weight)

Yield: 8.6 parts by weight
β-Lactam content: 97.8%
Calculated: C, 50.3; H, 5.6; N, 12.2; S, 5.6.
Found: C, 50.6; H, 5.9; N, 11.6; S, 5.6.
NMR-signals at τ = 2.4–2.8 (5H), 4.3–4.7 (3H), 5.8 (1H), 6.0–6.4 (4H) and 8.3–8.9 ppm (15 H).
Activity against *E. coli* C 165: 4
Activity against *Prot. morg.* 932: <1
Activity against Psdm. F 41: 4
Activity against Klebs. K 10: 8
N-pivaloyl-imidazolidin-2-one:

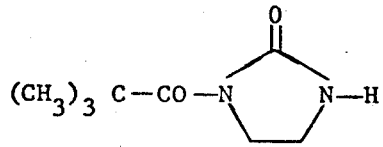

A suspension, cooled to 0°C, of imidazolidin-2-one (17.2 parts by weight) in tetrahydrofurane (200 parts by volume) was treated dropwise over the course of one hour, with pivaloyl chloride (24.2 parts by weight) at the same temperature. The mixture was then stirred for a further 3 hours at 0°C, triethylamine (27.8 parts by volume) was subsequently added dropwise while cooling with ice water, and the mixture was then left to stand overnight at room temperature. The triethylamine hydrochloride which had separated out was then filtered off, the filtrate was completely concentrated in vacuo by means of a rotary evaporator and the residue was further warmed for 1 hour, in vacuo, in a bath at 60°C. The oily product (crude yield: 32.8 parts by weight) was further processed, as it was. When an attempt was made to distill the substance in vacuo, severe decomposition occurred.

3-Pivaloyl-imidazolidin-2-on-1-carbonyl chloride

A solution of trimethylchlorosilane (16.65 parts by weight) in benzene (15 parts by volume) was added dropwise, over the course of one hour, to a boiling mixture if N-pivaloylimidazolidin-2-one (17.5 parts by weight), benzene (100 parts by volume) and triethylamine (23 parts by volume), the mixture was subsequently boiled for a further 6 hours and the triethylamine hydrochloride which had separated out was then filtered off. The filtrate was combined with a solution of phosgene (13 parts by weight) in benzene (20 parts by volume) and the mixture was then left to stand overnight at room temperature. The reaction mixture was then completely evaporated in vacuo and the oily residue was dried in a desiccator over NaOH. Crude yield 22.2 parts by weight. The product was reacted in this form with ampicillin.

EXAMPLE 22

Sodium D(—)-α-{[3-(ethoxy-carbonyl-amino-sulphonyl)-imidazolidin-2-on-1-yl]-carbonylamino}-benzyl-penicillin:

This penicillin was produced as described in Example 20 from ampicillin (9.8 parts by weight) and 3-(ethoxy-carbonyl-trimethylsilylamino)-imidazolidin-2-on-1-carbonyl chloride (8.0 parts by weight).

Yield: 2.8 parts by weight
β-Lactam content: 76.8%
NMR-signals at τ = 2.4–2.7 (5H), 6.3–6.7 (3H), 5.8 (1H), 5.85–6.4 (6H), 8.3–8.6 (6H) and 8.6–8.95 ppm (3H).

The 3-(ethoxy-carbonyl-trimethylsilylamino)-imidazolidin-2-on-1-carbonyl chloride used in the manufacture of this penicillin was obtained as follows:

3-(Ethoxy-carbonyl-trimethylsilylamino)-imidazolidin-2-on-1-carbonyl chloride

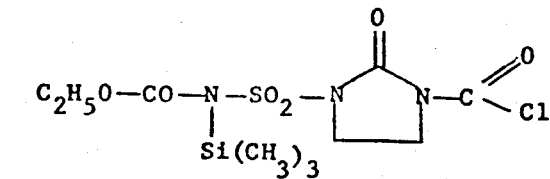

A mixture of the internal salt of ethyl (carboxysulphamoyl) triethylammonium hydroxide (G. M. Atkins, Jr., E. M. Burgers, J. amer. Chem. Soc. 90, 4744 (1968) (12.5 parts by weight) and imidazolidin-2-one (4.0 parts by weight was warmed in a bath at 100° for 2 hours, the resulting thick oil was dissolved in dichloromethane (80 parts by volume), triethylamine (10.9 parts by volume) was added, this solution was then heated to the boil and at the same time a solution of trimethylchlorosilane (15.8 parts by weight) in benzene (30 parts by volume) was added dropwise. Thereafter the mixture was boiled under reflux for a further 3 hours. A further 80 parts by volume of benzene were then added and the mixture was again boiled under reflux for 3 hours. After standing overnight at 20°C, solvent was distilled off under normal pressure up to a boiling point of 70°–75°C, the triethylamine hydrochloride was then filtered off while still hot and after cooling the filtrate was combined with a solution of phosgene (5.3 parts by weight) in benzene (20 parts by volume). This mixture was left to stand, well sealed, for 24 hours at 20°C. Undissolved material was then filtered off and the filtrate was completely evaporated in a rotary evaporator. An oil remained, which in the IR-spectrum possesses, in the carbonyl region, a double band with peaks at 1790 and 1730 cm⁻¹ (in dichloromethane). The substance was used without further purification for the reaction with ampicillin.

EXAMPLE 23

Sodium D(=)-α-[(3-cyclohexyloxycarbonyl-imidazolidin-2-on-1-yl)-carbonylamino]-benzylpenicillin:

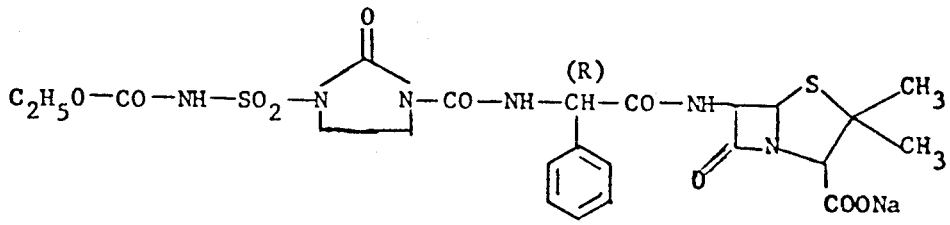

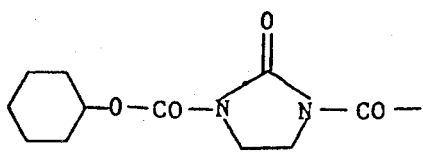

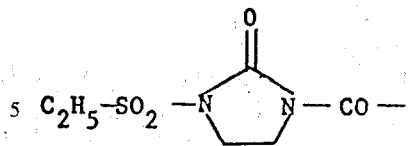

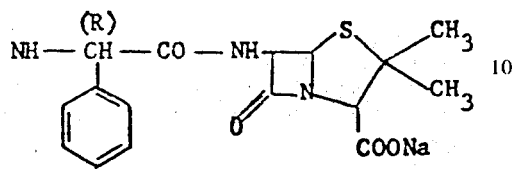

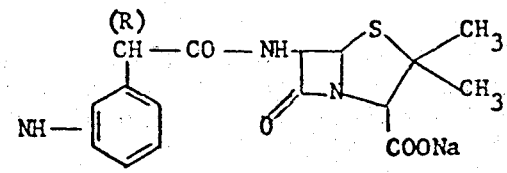

This penicillin was produced as described in Example 20 from ampicillin (6.6 parts by weight) and 3-cyclohexyloxy-carbonyl-imidazolidin-2-on-1-carbonyl chloride (4.0 parts by weight).

Yield: 1.6 parts by weight
β-Lactam content: 63.7%
Calculated: C, 48.3; H, 5.8; N, 10.5; S, 4.8.
Found: C, 47.5; H, 7.0; N, 10.5; S, 5.1.
NMR-signals at τ = 2.5–2.7 (5H), 4.3–4.7 (3H), 5.8 (1H), 6.0–6.3 (5H) and 8.2–9.2 ppm (16H).

3-Cyclohexyloxycarbonyl-imidazolidin-2-on-1-carbonyl chloride:

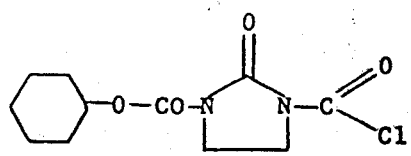

Triethylamine (5.8 parts by weight) was added dropwise to a mixture of imidazolidin-2-on-1-carbonyl chloride (7.4 parts by weight), tetrahydrofurane (50 parts by volume) and cyclohexanol (5.5 parts by weight) while stirring, and cooling with ice, the mixture was then slowly stirred overnight at room temperature and subsequently boiled for 1 hour under reflux, and the triethylamine hydrochloride was filtered off hot. The filtrate was completely evaporated in vacuo, the residue was triturated with cyclohexane and the solid product was filtered off and dried 3 days in a desiccator. Yield: 5.0 parts by weight. This substance (5.0 parts by weight was then suspended in tetrahydrofurane, triethylamine (5.2 parts by volume) was added, the mixture was boiled under reflux and a solution of trimethylchlorosilane (3.8 parts by weight) in tetrahydrofurane (10 parts by volume) was at the same time added dropwise. Thereafter the mixture was boiled overnight under reflux and insoluble matter was then filtered off hot. A solution of phosgene (2.6 parts by weight) in tetrahydrofurane (10 parts by volume) was slowly added to the filtrate at room temperature and the mixture was left to stand well sealed at room temperature for 24 hours. A precipitate which was present (largely triethylamine hydrochloride) was then filtered off and the filtrate was completely evaporated in vacuo. The crystalline residue was dried in a desiccator. The substance has a broad absorption between 1680 and 1820 cm⁻¹ in the carbonyl region of the IR-spectrum (Nujol). It was reacted, in this form, with ampicillin.

EXAMPLE 24

Sodium D(−)-α-[(3-ethanesulphonyl-imidazolidin-2-on-1-yl)-carbonylamino]-benzylpenicillin:

This penicillin was produced as described in Example 20 from ampicillin (9.4 parts by weight) and 3-ethanesulphonylimidazolidin-2-on-1-carbonyl chloride (5.0 parts by weight).

Yield: 5.7 parts by weight
β-Lactam content: 89.1%
The penicillin contains about 3.3% of sodium 2-ethyl-hexanoate and 6.7% of water. This was taken into account in the calculated values of the analytical data.
Calculated: C, 43.2; H, 5.1; N, 11.0; S, 10.0;
Found: C, 43.3; H, 5.8; N, 10.8; S, 9.9.

3-Ethanesulphonyl-imidazolidin-2-on-1-carbonyl chloride:

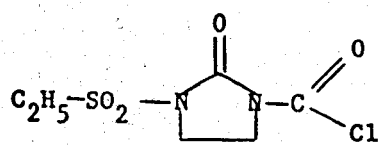

A mixture of imidazolidin-2-one (21.5 parts by weight) and ethanesulphonic acid chloride (32.5 parts by weight) was warmed for 4 hours in a bath at 150° to 180°. The evolution of HCl had by then largely ended. The reaction product was then successively extracted by boiling twice with benzene, twice with acetone and twice with ethyl acetate on a water bath and the extracts were decanted. The combined extracts were completely evaporated in vacuo and the residue was recrystallized once from ethyl acetate and once from acetone (in the latter case with the addition of charcoal powder). Yield: 8.1 parts by weight of N-ethanesulphonylimidazolidin-2-one. Melting point: 114°C.

The N-ethanesulphonyl-imidazolidin-2-one was then suspended in dichloromethane, a large excess of phosgene was introduced at 0°C, a little pyridine was added and the mixture was left to stand overnight. The excess phosgene was then largely removed by passing in dry air and the product (3-ethanesulphonyl-imidazolidin-2-on-1-carbonyl chloride) was suspended in dichloromethane and filtered off.

Melting point: 174°C.
Calculated: C, 30.0; H, 3.8; Cl, 14.8; N, 11.6; S, 13.3.
Found: C, 30.1; H, 3.8; Cl, 14.7; N, 11.8; S, 13.3.

EXAMPLE 25

A. Sodium D(−)-α-[(2-tosylamino-imidazolin(2)-1-yl)-carbonylamino]-benzylpenicillin:

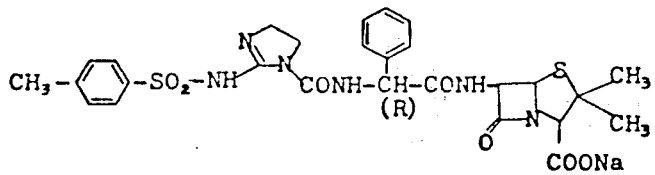

This penicillin was produced as described in Example 1 A from 7.5 parts by weight of 1-chloro-carbonyl-2-tosylamino-4,5-dihydroimidazole and 11 parts by weight of ampicillin.

Yield: 77%

β-Lactam content: 90%

Calculated (the water content of 6.1% was taken into account): C, 47.9; H, 5.0; N, 12.4; S, 9.5. C, 48.3; H, 4.8; N, 10.8; S, 9.1.

IR-bands at 3360–3200, 1775, 1725, 1675, 1608, 1538, 1290 and 1146 cm$^{-1}$ (in Nujol).

NMR-signals at τ = 2.2 (2H), 2.4–2.9 (7H), 4.5 (3H), 5.8 (1H), 6.25 (4H), 7.6 (3H), 8.4 (3H) and 8.5 ppm (3H).

B. 1-Chlorocarbonyl-2-tosylamino-4,5-dihydro-imidazole:

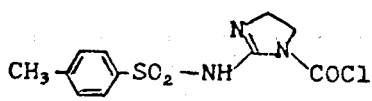

12 parts by weight of 2-tosylimino-imidazolidine (produced as described by Gompper and Hägele, Ber. 99, 2892 [1966]) were partly dissolved by 10 minutes' boiling in 150 parts by volume of absolute tetrahydrofurane, and thereafter rapidly cooled to 0°C by swirling in an ice bath. 6 parts by weight of phosgene were added to the suspension while stirring, the mixture was stirred for 30 minutes at 0°C, 5 parts by weight of triethylamine were then added dropwise and the whole was then stirred for a further 3 hours at room temperature. The excess phosgene was blown out by means of a stream of dry air and the precipitated triethylamine hydrochloride was removed from the tetrahydrofurane solution by filtration and was thoroughly eluted with absolute tetrahydrofurane. The combined solutions were evaporated to dryness in vacuo and the residual oil was caused to crystallize by trituration with methylene chloride and ether, filtered off and dried in vacuo.

Melting point = 101°C (decomposition).

Yield: 59%

Calculated: C, 43.8; H, 4.0; Cl, 11.8; N, 13.9; S, 10.6. Found: C, 43.0; H, 4.3; Cl, 13.5; N, 12.4; S, 10.0.

IR-bands at 3340, 3050, 1796, 1765, 1628, 1265, 1145, 1087 and 905 cm$^{-1}$ (in Nujol).

EXAMPLE 26

A. Sodium D(−)-α-[(2-oxo-3-propionyl-1-imidazolidinyl)-carbonylamino]-benzylpenicillin:

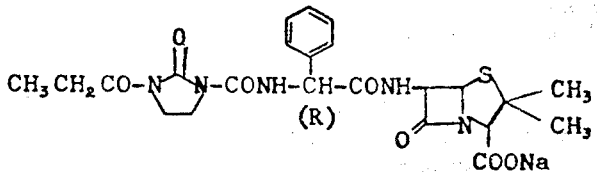

This penicillin was produced as described in Example 1 A from 9 parts by weight of 1-chloro-carbonyl-2-oxo-3-propionyl-imidazolidine and 17.5 parts by weight of ampicillin.

Yield: 38%

β-Lactam content: 89%

Calculated: (the water content of 2% was taken into account): C, 50.1; H, 5.0; N, 12.7; S, 5.8. Found: C, 49.8; H, 6.3; N, 12.7; S, 5.6.

IR-bands at 3290, 1760, 1732, 1670, 1603, 1525 and 1250 cm$^{-1}$ (in Nujol).

NMR-signals at τ = 2.3–2.8 (5H), 4.35 (1H), 4.5 (2H), 5.8 (1H), 6.0–6.3 (4H), 7.1 (2H), 8.4 (3H), 8.5 (3H) and 8.8 ppm (3H).

B. 1-Chlorocarbonyl-2-oxo-3-propionyl-imidazolidine:

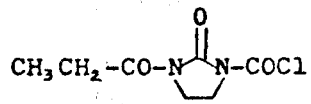

12 parts by weight of 1-propionyl-2-oxo-imidazolidine, 18.4 parts by weight of trimethylchlorosilane, 15.1 parts by weight of triethylamine and 80 parts by volume of toluene were together kept under reflux overnight, while stirring, and after cooling the precipitate was filtered off and eluted with toluene. 9 parts by weight of phosgene were added to the combined solutions, the mixture was left to stand overnight at room temperature and then evaporated in vacuo, and the residue was dried under an oil pump. The product was reacted in this form with ampicillin (Example 26 A).

IR-bands at 1822, 1770–1680, 1385 and 1280–1210 cm$^{-1}$.

C. 1-Propionyl-2-oxo-imidazolidine

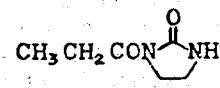

This substance was produced as described in Example 1 C from 17.2 parts by weight of 2-oxo-imidazolidine and 20.4 parts by weight of propionic acid chloridem Melting point = 147°C (from chloroform).

Yield: 45%

Calculated: C, 50.7; H, 7.0; N, 19.7. Found: C, 49.2; H, 7.1; N, 20.2.

IR-bands at 3240, 1760–1736, 1678 and 1280 cm$^{-1}$.

NMR-signals at τ = 3.8 (1H), 6.1 (2H), 6.4 (2H), 7.1 (2H) (in CDCl$_3$) and 8.8 ppm (3H).

EXAMPLE 27

Sodium D(−)-α-[(2-oxo-3-benzenesulphonyl-1-imidazolidinyl)-carbonylamino]-benzylpenicillin:

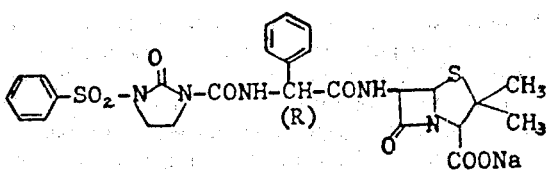

This penicillin was produced as described in Example 1 A from 5 parts by weight of 1-chloro-carbonyl-2-oxo-3-benzenesulphonyl-imidazolidine and 7.5 parts by weight of ampicillin.

Yield: 94%

β-Lactam content: 95%

Calculated (the water content of 3.5% was taken into account): C, 48.0; H, 4.4; N, 10.8; S, 9.9. Found: C, 48.1; H, 4.6; N, 10.9; S, 10.5.

IR-bands at 3300, 1770, 1740, 1680, 1610, 1530, 1260, 1184 and 1136 cm$^{-1}$.

NMR-signals at $\tau$ = 1.8–2.1 (2H), 2.2–2.8 (8H), 4.4 (1H), 4.5 (2H), 5.8 (1H), 6.15 (4H), 8.45 (3H) and 8.5 ppm (3H).

B. 1-Chlorocarbonyl-2-oxo-3-benzenesulphonyl-imidazolidine:

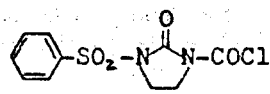

A mixture of 80 parts by weight of 1-benzenesulphonyl-2-oxo-imidazolidine, 69 parts by weight of phosgene, 31.6 parts by weight of pyridine and 350 parts by volume of dichloromethane, brought together at 0°C, was stirred overnight at room temperature and subsequently evaporated to dryness. Thereafter the material was suspended in 500 parts by volume of ice water and filtered off, the residue was taken up in 500 parts by volume of dichloromethane, the solution was dried over MgSO$_4$, filtered and again evaporated to dryness, and the residue was recrystallized from acetone/petroleum ether.

Melting point = 161°C.

Yield: 64%

Calculated: C, 41.6; H, 3.5; Cl, 12.3; N, 9.7; S, 11.1.

Found: C, 41.6; H, 3.0; Cl, 12.2; N, 9.7; S, 10.7.

IR-bands at 1802, 1732, 1318 and 1200 cm$^{-1}$. (in Nujol).

NMR-signals at $\tau$ = 1.8–2.1 (2H), 2.1–2.5 (3H) and 5.7–6.1 ppm (4H).

C. 1-Benzenesulphonyl-2-oxo-imidazolidine:

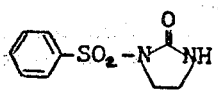

86 parts by weight of 2-oxo-imidazolidine, 194 parts by weight of benzenesulphonyl chloride, 800 parts by volume of tetrahydrofurane, 500 parts by volume of chloroform and 101 parts by weight of triethylamine were stirred overnight at 50°C and subsequently evaporated to dryness in vacuo. The residue was gradually added, while stirring, to 1,000 parts by volume of ice water, the mixture was filtered and the residue was recrystallized from ethanol.

Melting point = 155°C.

Yield: 35%

Calculated: C, 47.7; H, 4.4; N, 12.4; S, 14.2.

Found: C, 47.8; H, 4.5; N, 12.2; S, 14.3.

IR-bands at 3280, 1740, 1700, 1280, 1178, 1095 and 1060 cm$^{-1}$ (in Nujol).

NMR-signals at $\tau$ = 1.8–2.6 (6H), 6.1 (2H) and 6.7 ppm (2H) (in DMSO-d$_6$).

EXAMPLE 28

Sodium D(−)-α-(4-imino-5-ethoxycarbonyl-biureido)-benzyl-penicillin:

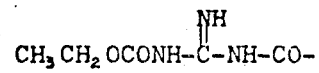
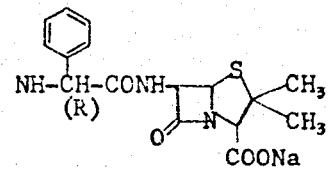

8 parts by weight of 1-(N-nitroso-N-methyl-aminocarbonyl)-3-ethoxycarbonyl-guanidine were added in portions, over the course of 15 minutes, to a stirred solution of 16.3 parts by weight of ampicillin and 5.7 parts by weight of triethylamine in 100 parts by volume of water. The initially foaming mixture was stirred for 4 hours at room temperature, insoluble matter was filtered off and the filtrate was covered with 200 parts by volume of ethyl acetate and acidified to pH = 2 with dilute hydrochloric acid, while cooling with ice. The penicillin was isolated as the sodium salt from the ethyl acetate solution of the penicillin-acid, as described in Example 1 A, by precipitation with sodium 2-ethyl-hexanoate solution.

Yield: 15%

β-Lactam content: 66%

IR-bands at 3250, 1760 and 1665 cm$^{-1}$.

NMR-signals at $\tau$ = 2.4–2.8 (5H), 4.4 (1H), 4.5 (2H), 5.8 (3H), 8.4 (3H), 8.5 (3H) and 8.8 ppm (3H).

B. 1-(N-Nitroso-N-methyl-aminocarbonyl)-3-ethoxycarbonylguanidine:

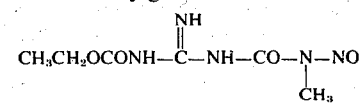

A solution of 7.3 parts by weight of sodium nitrite in 13 parts by volume of water was added dropwise over the course of 20 minutes to an ice-cooled solution of 11 parts by weight of 1-(methylaminocarbonyl)-3-ethoxycarbonyl-guanidine in 58 parts by volume of 5 N hydrochloric acid. The mixture was stirred for a further hour at 0°C and the yellow precipitate formed was filtered off and eluted with a little ice water.

Yield: 8.4 parts by weight. The product, in the moist form, was reacted analogously to Example 28 A to give the penicillin. A small sample was dried over P$_2$O$_5$ in vacuo.

Melting point = 116°C (decomposition).

Calculated (a contents of 15% NaCl was taken into account in the calculation): C, 28.1; H, 4.3; N, 27.4.

Found: C, 27.0; H, 4.3; N, 28.2.

IR-bands at 3400-2400, 1790, 1762 and 1725 cm$^{-1}$.

C. 1-(Methylaminocarbonyl)-3-ethoxycarbonyl-guanidine:

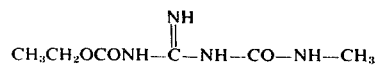

5.1 parts by weight of methylisocyanate were added to a suspension of 10 parts by weight of ethoxycarbonylguanidine (manufactured according to Isr. J. Chem. 8, 651 [1970] ) in 60 parts by volume of anhydrous dioxane, in the course of which the temperature rose to 45°C and the precipitate dissolved. After a short time, a crystalline precipitate separated out again, which was filtered off after cooling and washed with ether. It was dried in vacuo over $P_2O_5$ and paraffin chips.

Melting point = 150°C.
Yield: 80%
Calculated: C, 38.2; H, 6.4; N, 29.8.
Found: C, 38.8; H, 6.4; N, 29.1.
IR-bands at 3380, 3300, 1730, 1700–1600, 1580–1520, 1300, 1260 and 1155 cm$^{-1}$ (in Nujol).
NMR-signals at $\tau$ = 1.0 (3H), 2.8 (1H), 5.95 (2H), 7.3 (3H) (in DMSO-d$_6$) and 8.8 ppm (3H).

EXAMPLE 29

A. Sodium D(−)-α-{3-[N-(1,1-dioxo-isothiazolidin-2-yl)-carbonyl]-3-methyl}-ureido-benzylpenicillin:

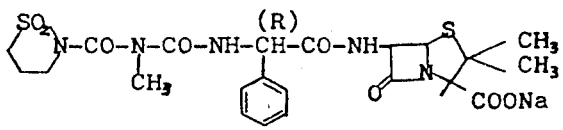

This pencillin was produced as described in Example 20 from 12.0 parts by weight of ampicillin and 6.3 parts by weight of N-[(1,1-di-oxo-isothiazolidin-2-yl)-carbonyl]-N-methylcarbamic acid chloride. However, when acidifying the penicillin salt solution, it was acidified to pH 2.0, the solution was at the same time kept at 0°C, and the solution of the free penicillin-acid in an ether-ethyl acetate mixture was only dried for 15 minutes at 0°C over MgSO$_4$.

Yield: 11.2 parts by weight.
β-Lactam content: about 100%.
Electrophoresis of the penicillin showed that only one antibiotically active substance was present.
Specific rotation: [α]$_{589}$ + 141° (methanol/water).
NMR-signals at $\tau$ = 2.4–2.8 (5H), 4.3–4.6 (3H), 5.8 (1H), 5.9–6.3 (2H), 6.4–6.8 (2H), 6.6 (3H), 7.3–7.7 (2H) and 8.3–8.5 ppm (6H).

B.
N-[(1,1-Dioxo-isothiazolidin-2-yl)-carbonyl]-N-methyl-carbamic acid chloride:

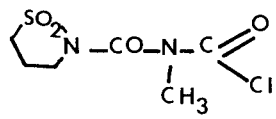

A solution of 7.7 parts by weight of 1,1-dioxo-isothiazolidine and 8.8 parts by volume of triethylamine in 30 parts volume of tetrahydrofurane was added dropwise at room temperature to a solution of 10.0 parts by weight of bis-chlorocarbonyl-methylamine (Farbenfabriken Bayer : German Offenlegungsschrift No. 1,932,830) in tetrahydrofurane (100 parts by volume). The mixture was stirred for a further hour at room temperature and the triethylamine hydrochloride formed was filtered off and washed with tetrahydrofurane. The combined filtrates were completely evaporated in vacuo and the residue was recrystallized from hot tetrahydrofurane with addition of a little pentane.

Yield: 13.1 parts by weight.
Melting point = 102°–103°C.
Calculated: C, 30.0; H, 3.8; Cl, 14.7; N, 11.6; S, 13.3.
Found: C, 30.1; H, 3.9; Cl, 14.3; N, 11.6; S, 13.3.
NMR-signals at $\tau$ = 6.15 (triplet) (2H), 6.65 (triplet) (2H), 6.8 (3H) and 7.3–7.9 ppm (multiplet) (2H).
IR-spectrum: 1700 and 1740 cm$^{-1}$ (C = 0).

EXAMPLE 30

A. Sodium D(−)-α-[3-(methylsulphonyl-amino-carbonyl)-imidazolidinon-2-yl-1]-carbonylamino-benzylpenicillin:

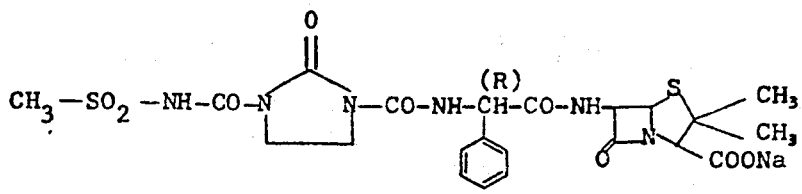

This penicillin was produced from 10.0 parts by weight of ampicillin and 5.9 parts by weight of 3-(methyl-sulphonylamino-carbonyl)-1-chlorocarbonyl-imidazolidinone-(2) as described in Example 20.

Yield: 9.8 parts by weight.
β-Lactam content: 82%
NMR-signals at $\tau$ = 2.4–2.8 (5H), 4.3–4.65 (3H), 5.8 (1H), 6.05–6.45 (4H), 6.95 (3H) and 8.35–8.75 ppm (6H).
Calculated: *) C, 40.1; H, 5.2; N, 11.7; S, 8.9.
C, 40.4; H, 5.2; N, 11.7; S, 8.8.

*) (a content of 5.8% of sodium 2-ethylhexanoate and 10% of water was taken into account).

On electrophoresis (micro-biological evaluation with Subtilis) the penicillin shows only one spot.

B.
1-(Methylsulphonyl-amino-carbonyl)-3-chlorocarbonyl-imidazolid-2-one:

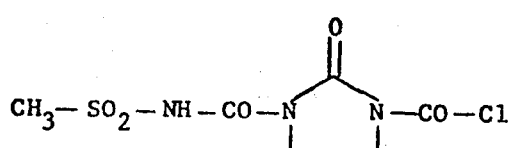

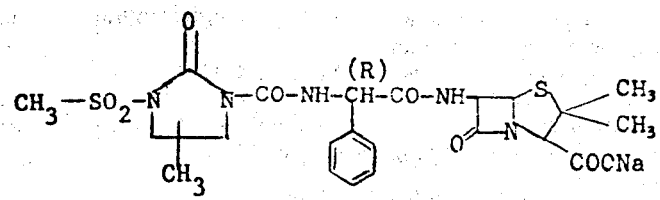

7.0 parts by weight of 1-chlorocarbonylimidazolidinone-(2) were dissolved or suspended in 50 parts by volume of tetrahydrofurane, 5.7 parts by weight of methanesulphonyl isocyanate were added and the mixture was first stirred for 26 hours at room temperature. Since practically no reaction had yet occurred at that time, 5 drops of pyridine were added and the mixture was stirred for a further 65 hours at room temperature. A crystalline precipitate was then filtered off.

Yield: 10.5 parts by weight.
Melting point = 218°–220°C.
Calculated: C, 26.7; H, 3.0; Cl, 13.1; N, 15.6; S, 11.9.
Found: C, 27.2; H, 3.2; Cl, 12.8; N, 15.5; S, 11.9.
NMR-signals at $\tau = 5.8$–6.2 (multiplet) (4H) and 6.7 ppm (3H).
IR-spectrum: 1800 and 1730 cm$^{-1}$ (C = 0).

EXAMPLE 31

A. Sodium D(−)-α-(5-mesyl-biureido)-benzylpenicillin

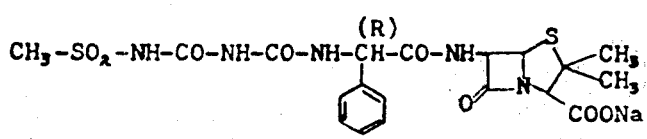

This penicillin was produced as described in Example 20 from 11.2 parts by weight of ampicillin and 6.4 parts by weight of N-mesyl-N'-chlorocarbonyl-urea.

Yield: 3.4 parts by weight.
β-Lactam content: 66.5%.
Calculated: *) C, 39.3; H, 5.1; N, 10.9; S, 10.0.
Found: C, 39.6; H, 6.1; N, 10.2; S, 10.0.
*) (a content of 6.6% of sodium 2-ethyl-hexanoate and 9% of water was taken into account).

A microbiologically (*Bact. Subtilis*) developed electropherogram showed, in addition to one large inhibition halo, a second though very small inhibition halo.

B. N-Mesyl-N'-chlorocarbonyl-urea:

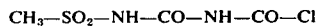

CH₃—SO₂—NH—CO—NH—CO—Cl 6.1 parts by volume of pyridine were added dropwise, while cooling, to a mixture of 10.5 parts by weight of N-mesylurea, 60 parts by volume of dichloromethane and 15.0 parts by weight of phosgene, while cooling, and after some hours at 0°C the excess of the phosgene was removed, the precipitate present was filtered off and the filtrate was completely concentrated in vacuo. A viscous oil remained, which had an absorption at 1800 cm$^{-1}$ in the carbonyl region of the IR-spectrum. The substance was used without further purification for the production of the penicillin.

EXAMPLE 32

A. Sodium D(−)-α-[(3-methylsulphonyl-4- or 5-methyl-imidazolidin-2-on-1-yl)-carbonylamino]-benzylpenicillin This penicillin was produced from 12.0 parts by weight of ampicillin and 7.7 parts by weight of 1-methylsulphonyl-3-chlorocarbonyl-4- or -5-methyl-imidazolidin-2-one as described in Example 20.

Yield: 9.3 parts by weight.
β-Lactam content: 94%
Calculated (with 1.33 mol H₂O): C, 44.0; H, 4.8; N, 11.7; S, 10.7.
Found: C, 44.0; H, 5.0; N, 11.4; S, 10.6.
Specific rotation: [α]₅₈₉ + 135.9° (methanol-water).
NMR-signals at $\tau = 2.3$–2.65 (5H), 4.25–4.6 (3H), 5.75 (1H), 5.8–6.4 (3H), 6.6 (3H), 8.3–8.5 (6H) and 8.6–8.8 ppm (3H).

B. 1-Methanesulphonyl-3-chlorocarbonyl-4- or -5-methyl-imidazolidin-2-one

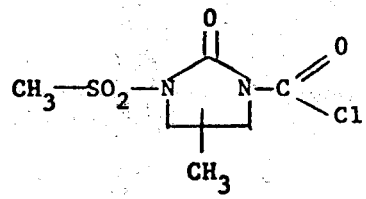

13.4 parts by weight of 1-methanesulphonyl-4- or -5-imidazolidin-2-one were added to a solution of 15.0 parts by weight of phosgene in 60 parts by volume of dichloromethane and 6.1 parts by volume of pyridine were added dropwise at 0°C. The mixture was then left to stand overnight at room temperature, phosgene which was still present was removed by means of a dry stream of air and the solution was then completely concentrated in vacuo. The residue, an oil, was dried in a desiccator over P₂O₅.

Yield: 27 parts by weight.
IR-bands in the carbonyl region: 1800, 1760 and 1720 cm$^{-1}$.

C. 1-Methanesulphonyl-4- or -5-methyl-imidazolidin-2-one

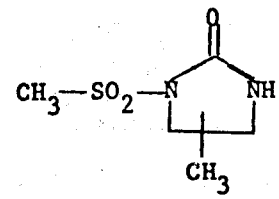

A mixture of 53.8 parts by weight of 4-methylimidazolidin-2-one and 64.6 parts by weight of methanesulphonic acid chloride was heated in a bath at 90° until the evolution of HCl had ceased (approximately 7 hours). The resulting crude product (yield 34.2 parts by weight) melted at 131°–133°. A product of melting point 135°C is obtained by recrystallization from water on a waterbath.

Calculated: C, 33.7; H, 5.7; N, 15.7; S, 18.0.
Found: C, 33.5; H, 5.5; N, 15.3; S, 18.2.
NMR-signals at τ = 5.9–6.7 (multiplet) (3H), 6.75 (3H) and 8.65 u. 8.75 ppm (3H) (doublet).

D. 4-Methylimidazolidin-2-one

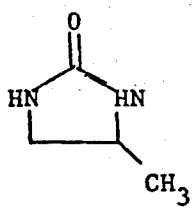

This substance was obtained by heating a mixture of 383 parts by weight of 1,2-diaminopropane and 611 parts by weight of carbonic acid diethyl ester to 180° in an autoclave for 10 hours and recrystallizing from isopropanol and methanol.

Yield: 109 parts by weight.
Melting point = 130°C.

EXAMPLE 33

A. Sodium D(−)-α-[3-(thienyl(2)-sulfonyl)-imidazolidin-2-on-1-yl-carbonylamino]-benzylpenicillin

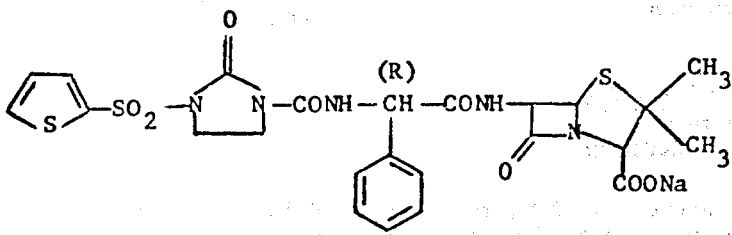

This penicillin was produced as described in Example 1 A from 3.3 parts by weight of 1-chloro-carbonyl-2-oxo-3-(thienyl(2)-sulfonyl)-imidazolidine and 5.0 parts by weight of ampicillin.

Yield: 89%.
β-Lactam content: 83%.
Calculated (the water content of 6.4% and the sodium-2-ethylhexanoate content of 2.1% were taken into account): C, 43.4; N, 10.2; H, 4.4; S, 14.1.
Found: C, 43.7; N, 10.0; H, 4.2; S, 14.1.
IR-bands at 3320, 1770, 1742, 1680, 1610, 1530, 1258 and 1188 cm⁻¹.
NMR-signals at τ = 2.0 –2.2 (2H), 2.4–2.9 (6H), 4.4 (1H), 4.5 (2H), 5.8 (1H), 6.2 (4H), 8.45 (3H), and 8.5 ppm (3H).

B. 1-Chlorocarbonyl-2-oxo-3-(thienyl(2)-sulfonyl)-imidazolidine

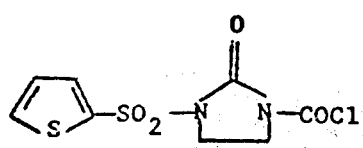

This carbamic acid chloride was produced as described in Example 27 B from 2.9 parts by weight of 1-thienyl(2)-carbonyl)-2-oxo-imidazolidine and 2.7 parts by weight of phosgene.

Yield: 80%.
Melting point: 166°C.
IR-bands at 3080, 1800, 1728, 1300 and 1178 cm⁻¹ (in nujol).

C. 1-(Thienyl(2)-sulfonyl-2-oxo-imidazolidine

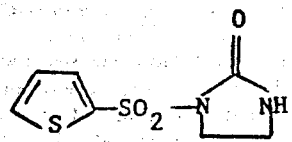

The mixture of 14 parts by weight of 2-chlorosulfonylthiophene and 6.6 parts by weight of imidazolidone-2 were heated with stirring to 150°C until the evolution of HCl had finished (ca. 4 hours). After cooling the reaction product was extracted with 150 parts by volume of chloroform/H₂O (2:1), the chloroform-layer was separated, dried over MgSO₄ and evaporated to dryness. The residue was recrystallized from acetone.

Yield: 20.2%.
Melting point = 174°C.
Calculated: C, 36.1; H, 3.5; N, 12.0; S, 27.5.
Found: C, 35.8; H, 3.5; N, 11.9; S, 27.5.
IR-bands at 3230, 3080, 1738, 1705, 1175 and 1062 cm⁻¹ (in nujol).
NMR-signals at τ = 2.1–2.4 (2H), 2.8–3.0 (1H), 4.0 (1H), 5.9–6.2 (2H), and 6.3–6.7 ppm (2H) (in CDCl₃).

D. 2-Chlorosulfonyl-thiophene

This compound was produced as described for chlorosulfonyl-methylthiophene in J. org. Chem. 33, 1357 (1968) from thiophene, chlorosulfonic acid and PCl₅. The yield was 70%. The substance was a low melting solid.

Boiling point = 117°C (8 mm Hg).
Calculated: C, 26.3; H, 1.6; Cl, 19.4; S, 35.0.
Found: C, 25.9; H, 2.6; Cl, 19.4; S, 34.2.
IR-bands at 3110, 1196, 1032 and 740 cm⁻¹.
NMR-signal at τ = 2.08 (2H) and 2.75 ppm (1H).

EXAMPLE 34

A. Sodium D(−)-α-[(2-oxo-3-acetyl-1,3-diaza-cyclohex-1-yl)-carbonylamino]-benzylpenicillin

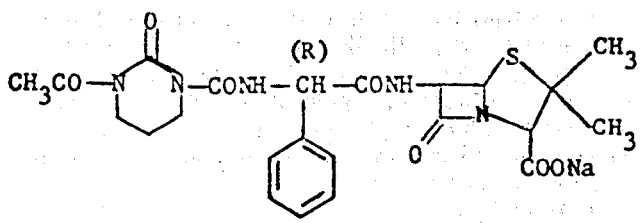

This penicillin was produced as described in Example 1 A from 7.6 parts by weight of 1-chlorocarbonyl-2-oxo-3-acetyl-1,3-diaza-cyclohexane and 16.5 parts by weight of ampicillin.

Yield: 93%.

β-Lactam content: 94%.

Calculated (the water content of 6% was taken into account):
C, 48.1; H, 5.2; N, 12.2; S, 5.5.
Found: C, 48.0; H, 5.5; N, 12.2; S, 6.2.

IR-bands at 3250, 1772, 1700, 1615, 1520, 1305 and 1180 cm$^{-1}$.

NMR-signals at $\tau$ = 2.3–2.8 (5H), 4.4 (1H), 4.5 (2H), 5.8 (1H), 6.0–6.4 (4H), 7.5 (3H), 7.8–8.3 (2H), 8.4 (3H) and 8.5 ppm (3H).

B. 1-Chlorocarbonyl-2-oxo-3-acetyl-1,3-diaza-cyclohexane

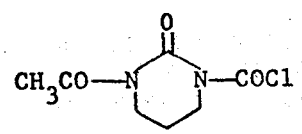

This carbamic acid chloride was produced as described in Example 27 B from 7.1 parts by weight of 1-acetyl-2-oxo-1,3-diaza-cyclohexane and 10 parts by weight of phosgene.

Oil. Yield: 89%

Calculated: C, 41.1; H, 4.4; Cl, 17.4; N, 13.7.
Found: C, 41.1; H, 4.5; Cl, 17.1; N, 13.3.

IR-bands at 2950, 1800, 1730, 1706, 1400, 1376, 1320, 1295, 1202, 1178 and 1054 cm$^{-1}$.

NMR-signals at $\tau$ = 5.9–6.3 (4H), 7.45 (3H) and 7.65–8.15 ppm (2H).

C. 1-Acetyl-2-oxo-1,3-diaza-cyclohexane

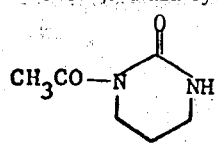

The mixture of 10 parts by weight of 1,3-diaza-cyclohexan-2-one, 11.8 parts by weight of acetylchloride, 8.7 parts by weight of pyridine, 50 parts by volume of tetrahydrofurane and 50 parts by volume of chloroform was stirred for 24 hours at room temperature, filtered and washed out with tetrahydrofurane chloroform (1:1). The combined solutions were evaporated to dryness, recrystallized from acetone/ethanol; 50 parts by volume of NaHCO$_3$-solution were added, and the mixture was extracted 3 times with 50 parts by volume of ethylacetate at a time. The combined organic solutions were dried over MgSO$_4$, evaporated to dryness, and the residue was recrystallized from acetone/petrol-ether.

Yield: 53%.

Melting point: 132°C.

Calculated: C, 50.7; H, 7.0; N, 19.7.
Found: C, 50.5; H, 7.1; N, 20.1.

IR-bands at 3345, 1708, 1664, 1320, 1281, 1250, 1175, 1130 and 1022 cm$^{-1}$ (in nujol).

NMR-signals at $\tau$ = 6.1–6.4 (2H), 6.6–6.85 (2H), 7.5 (3H) and 7.8–8.3 ppm (2H) (in CD$_3$OD).

EXAMPLE 35

A. Sodium D(−)-α-[(3-formyl-1,3-diaza-cyclohexan-2-on-1-yl)-carbonylamino]-benzylpenicillin

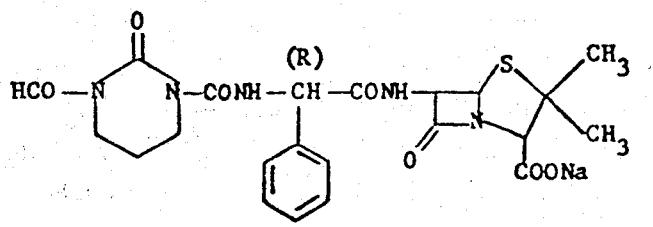

This penicillin was produced as described in Example 1 A from 8.1 parts by weight of 1-chlorocarbonyl-2-oxo-3-formyl-1,3-diaza-cyclohexane and 18.9 parts by weight of ampicillin.

Yield: 41%.

β-Lactam content: 94%.

Calculated (the water content of 3% was taken into account): C, 48.7; H, 4.8; N, 12.9; S, 5.9.
Found: C, 48.4; H, 5.4; N, 11.3; S, 6.5.

IR-bands at 3270, 1765, 1700, 1675, 1603, 1310 and 1183 cm$^{-1}$.

NMR-signals at $\tau$ = 0.6 (1H), 2.3–2.8 (5H), 4.4 (1H), 4.5 (2H), 5.8 (1H), 6.0–6.5 (4H), 7.75 (2H), 8.4 (3H) and 8.5 ppm (3H).

B. 1-Chlorocarbonyl-2-oxo-3-formyl-1,3-diaza-cyclohexane

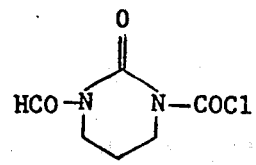

This carbamic acid chloride was produced as described in Example 27 B from 5 parts by weight of 1-formyl-2-oxo-1,3-diaza-cyclohexane and 6 parts by weight of phosgene. The substance, an oil, was used without further purification for the production of the penicillin of Example 35 A. IR-bands at 1790, 1685, 1300 and 1165 cm$^{-1}$.

C. 1-Formyl-2-oxo-1,3-diaza-cyclohexane

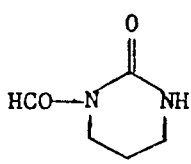

The mixture of 10 parts by weight of 1,3-diaza-cyclohexane-2-one, 49 parts by weight of trimethylchlorosilane, 25 parts by weight of triethylamine and 150 parts by volume of dioxane were boiled for 3 days with stirring and exclusion of moisture, then filtered, evaporated to 50 parts by volume in vacuo and stirred overnight with 11.5 parts by volume of formic acid-acetic acid anhydride. The mixture was evaporated to dryness in vacuo, and the residue was recrystallized from ethanol/ether.

Yield: 40%.
Melting point: 100°C.
Calculated: C, 46.9; H, 6.9; N, 21.9.
Found: C, 46.7; H, 6.3; N, 22.0.
IR-bands at 3250, 3120, 1690, 1312 and 1166 cm$^{-1}$ (in nujol).

EXAMPLE 36

A. Sodium D(—)-α-[(3-mesyl-1,3-diaza-cyclohexan-2-on-1-yl)-carbonylamino]-benzylpenicillin

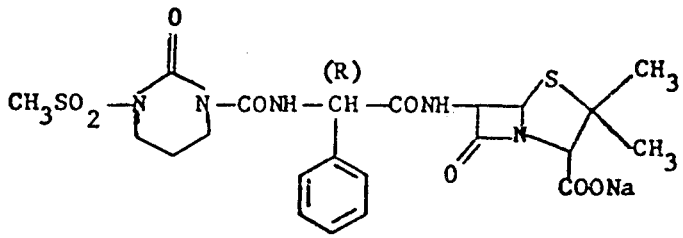

This penicillin was produced as described in Example 1 A from 5.6 parts by weight of 1-chlorocarbonyl-2-oxo-3-mesyl-1,3-diaza-cyclohexane and 10 parts by weight of ampicillin.

Yield: 52%.
β-Lactam content: 94%.
Calculated (the water content of 2.9% and the sodium-2-ethylhexanoate content of 2.9% were taken into account): C, 44.8; H, 4.8; N, 11.4; S, 10.4.
Found: C, 44.9; H, 5.1; N, 11.0; S, 10.3.
IR-bands at 3300, 1765, 1705–1665, 1605, 1515, 1345 and 1165 cm$^{-1}$.

NMR-signals at τ = 2.3–2.8 (5H), 4.4 (1H), 4.5 (2H), 5.8 (1H), 6.0–6.4 (4H), 6.6 (3H), 7.7–8.3 (2H), 8.4 (3H) and 8.5 ppm (3H).

B. 1-Chlorocarbonyl-2-oxo-3-mesyl-1,3-diaza-cyclohexane

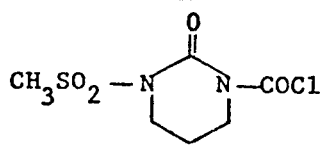

This carbamic acid chloride was produced as described in Example 4B from 4.5 parts by weight of 1-mesyl-2-oxo-1,3-diaza-cyclohexane, 6.9 parts by weight of trimethyl-chlorosilane and 5.2 parts by weight of phosgene. The oily reaction product was used without further purification for the reaction with ampicillin (Example 36 A).

Yield: 83%.
IR-bands at 2980, 2950, 1790, 1760–1680, 1742, 1355, 1215, 1162, 982 and 855 cm$^{-1}$.

C. 1-Mesyl-2-oxo-1,3-diaza-cyclohexane

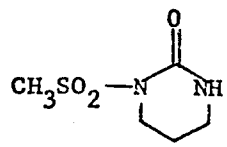

This compound was produced as described in Example 35 C from 10 parts by weight of 1,3-diaza-cyclohexan-2-one, 49 parts by weight of trimethylchlorosilane and 30 parts by weight of mesylchloride. The reaction product was recrystallized from acetone at low temperature and thereafter from acetone/ethanol.

Yield: 34%.
Melting point: 172°C.
Calculated: C, 33.7; H, 5.6; N, 15.8; S, 18.0.
Found: C, 33.4; H, 5.7; N, 15.6; S, 17.3.
IR-bands at 3210, 3070, 1692, 1340 and 1170 cm$^{-1}$ (in nujol).
NMR-signals at τ = 6.25 (2H), 6.5–6.8 (2H), 6.7 (3H) and 7.8–8.3 ppm (2H) (in CD$_3$OD).

EXAMPLE 37

A. Sodium D(—)-α-[(3phenylsulfonyl-1,3-diaza-cyclohexan-2-on-1-yl)-carbonylamino]-benzylpenicillin:

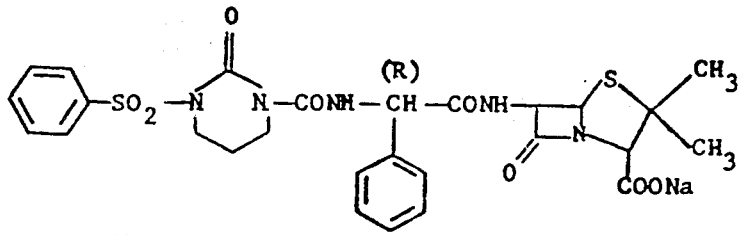

This penicillin was produced as described in Example 1 A from 2.6 parts by weight of 1-chlorocarbonyl-2-oxo-3-phenylsulfonyl-1,3-diaza-cyclohexane and 3.8 parts by weight of ampicillin.

Yield: 82%.
β-Lactam content: 85%.
IR-bands at 3300, 1770, 1695, 1610, 1520 and 1180 cm$^{-1}$.
NMR-signals at τ = 1.9–2.1 (2H), 2.3–2.6 (3H), 2.6 (5H), 4.54 (1H), 4.6 (2H), 5.85 (1H), 5.9–6.5 (4H), 7.8–8.25 (2H), 8.47 (3H) and 8.52 ppm (3H).

B.
1-Chlorocarbonyl-2-oxo-3-phenylsulfonyl-1,3-diaza-cyclohexane

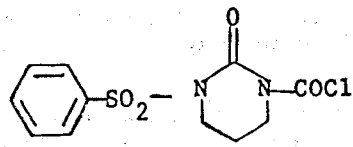

This carbamic acid chloride was produced as described in Example 27 A from 6 parts by weight of 1-phenylsulfonyl-1,3-diaza-cyclohexane-2-one and 5 parts by weight of phosgene. The product was recrystallized from acetone/petrolether.
Yield: 35%.
Melting point: 123°C.
IR-bands at 3350, 1790, 1692 and 1162 cm$^{-1}$ (in nujol).

C. 1-Phenylsulfonyl-2-oxo-1,3-diaza-cyclohexane

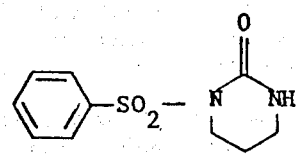

20.4 parts by weight of benzenesulfochloride in 20 parts by volume of tetrahydrofurane were added dropwise at 10°–15°C over the course of 15 minutes to a stirred mixture of 10 parts by weight of 1,3-diaza-cyclohexane-2-one, 80 parts by volume of tetrahydrofurane and 80 parts by volume of chloroform, followed by 10.1 parts by weight of triethylamine at the same temperature. The mixture was stirred at 10°–15°C for 30 minutes and then overnight at 50°C. Subsequently the mixture was evaporated to dryness; the residue was stirred with 100 parts by volume of water, filtered, stirred with water once more, filtered and washed with ethanol.
Yield: 28%.
Melting point: 207°C.
Calculated: C, 50.0; H, 5.0; N, 11.7; S, 13.3.
Found: C, 49.0; H, 5.0; N, 11.7; S, 12.5.
IR-bands at 3320, 1665, 1348, 1300 and 1175 cm$^{-1}$ (in nujol).
NMR-signals at $\tau$ = 1.8–2.2 (2H), 2.3–2.7 (3H), 6.0 (2H), 6.7 (2H) and 8.0 ppm (2H) (in CDCl$_3$).

EXAMPLE 38

Sodium D(−)-α-[(3-methylsulfonyl-imidazolidin-2-on-1-yl-carbonylamino]-1,4-cyclohexadien-yl-1-methylpenicillin

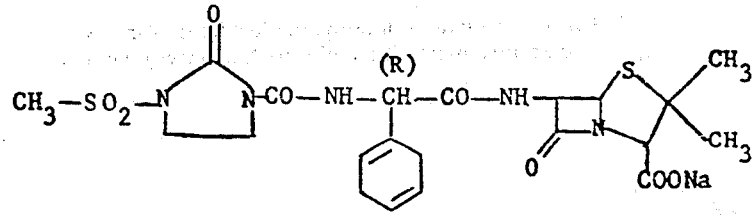

This penicillin was produced as described in Example 20 from 2.5 parts by weight of D(−)-α-Amino-1,4-cyclohexadien-yl 1-methylpenicillin and 1.6 parts by weight of 1-methylsulfonyl-3-chlorocarbonyl-imidazolidin-2-one.

Yield: 2.6 parts by weight.
β-Lactam content: 93%.
NMR-signals at $\tau$ = 4.0 (1H), 4.3 (2H), 4.4 (2H), 4.9 (1H), 5.8 (1H), 6.0 (4H), 6.6 (3H), 7.2 (4H) and 8.2–8.4 ppm (6H).

EXAMPLE 39

A. Sodium D(−)-α-[(3-methylsulphonyl-imidazolidin-2-on-1-yl)-carbonylamino]benzylpenicillin

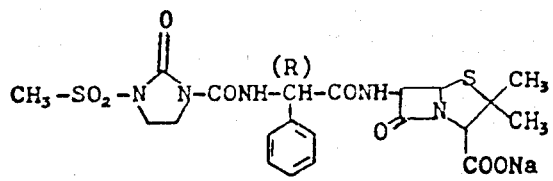

6.8 parts by weight of D(−)-α-[(3-methylsulphonylimidazolidin-2-on-1-yl)-carbonylamino]-phenylacetic acid were dissolved in 40 parts by volume of methylene chloride with the addition of a little tetrahydrofurane, the solution was cooled to −40°C and 2.0 parts by weight of N-methylmorpholine were added with vigorous stirring. Thereafter, a solution of 3.75 parts by weight of tetramethylchloroformamidinium chloride in 15 parts by volume of methylene chloride, also cooled to −40°C, was added all at once with vigorous stirring and the mixture was stirred for 5 minutes at −40°C and then combined with a solution, cooled to 0°C and kept at pH 2.5, of 4.7 parts by weight of 6-aminopenicillanic acid in 30 parts by volume of 80% strength aqueous tetrahydrofurane. The pH value of the mixture was maintained at 2.5 by addition of further N-methylmorpholine. The mixture was stirred for 30 minutes without cooling, while the pH was maintained at 2.5. Thereafter, 40 parts by volume of water were added, the pH value was then adjusted to 7, methylene chloride and tetrahydrofurane were stripped off on a rotary evaporator, the solution was extracted once with 50 parts by volume of ethyl acetate and the aqueous phase was covered with fresh ethyl acetate. The mixture was acidified with dilute hydrochloric acid to pH = 1.5 under stirring and cooling with ice, the ethyl acetate was separated off, the aqueous phase was extracted twice more with ethyl acetate and the combined organic phases were washed with water and dried over MgSO$_4$. Thereafter they were filtered, 20 parts by volume of a molar solution of sodium 2-ethylhexanoate in ether containing methanol were added, the mixture was evaporated practically to dryness in vacuo, the residue was dissolved in the minimum possible amount of methanol and the sodium salt of the penicillin was precipitated by adding a tenfold amount of absolute ether with shaking. It was filtered off, thoroughly washed with absolute ether and dried over P$_2$O$_5$ in a vacuum dessicator.
Yield: 84%.
β-Lactam content: 74%
Calculated: C, 43.4; H, 4.8; N, 11.3; S, 10.4.

Found: C, 43.4; H, 5.4; N, 11.3; S, 10.3.

IR-bands at 3325, 3055, 3025, 3002, 2965, 2924, 2865, 1771, 1738, 1679, 1610, 1529, 1398 and 1171 cm⁻¹.

NMR-signals at τ = 2.3–2.8 (5H), 4.4 (1H), 4.5 (2H), 5.8(1H), 6.15 (4H), 8.4 (3H) and 8.5 ppm (3H).

B.1.
D(−)-α-[(3-methylsulphonyl-imidazolidin-2-on-1-yl)-carbonylamino]-phenylacetic acid

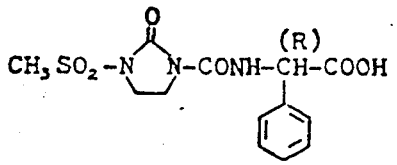

16.6 parts by weight of D(−)-C-phenylglycine were dissolved in 150 parts by volume of 50% strength aqueous dioxane with addition of a sufficient amount of 2N sodium hydroxide solution. The pH of the solution was now reduced to 7.5 by adding 2 N hydrochloric acid, whereupon the aminoacid partially separated out again in a finely divided form. 1-Chlorocarbonyl-3-methylsulphonyl-imidazolid-2-one was now added in portions under cooling with ice and the pH of 7.5 was maintained by simultaneously adding 2 N sodium hydroxide solution. The mixture was further stirred, without cooling, until the pH-value remained constant at 7.5 even without addition of sodium hydroxide solution (about 10 minutes). Thereafter, 50 parts by volume of water were added, the mixture was evaporated on a rotary evaporator to half the original volume and the residue was extracted once with 50 parts by volume of ethyl acetate, after unreacted C-phenylglycine had been filtered off. Thereafter the mixture was acidified to pH = 2 and repeatedly extracted with ethyl acetate. The combined ethyl acetate phases were washed with water, dried over MgSO₄, filtered, evaporated to dryness and recrystallized from acetone/nitromethane. Melting point = 250°C.

Yield: 56%

Calculated: C, 45.7; H, 4.4; N, 12.3; S, 9.4.
Found: C, 45.7; H, 4.5; N, 12.3; S, 9.2.

IR-bands at 3345, 3600, -2300, 1731, 1652, 1538, 1210 and 1168 cm⁻¹ (in Nujol).

NMR-signals at τ = 1.2 (1H), 2.55 (5H), 4.6 (1H), 6.2 (4H) and 6.6 ppm (3H).

2.
D,L-α-[(3-methylsulphonyl-imidazolidin-2-on-1-yl)carbonylamino]-4-chloro-phenylacetic acid

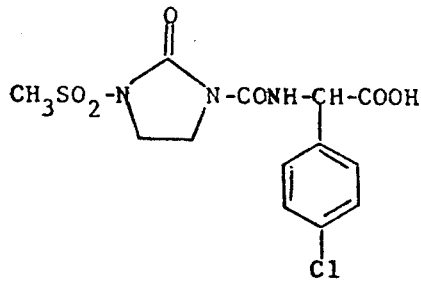

This carboxylic acid was produced as described in Example 39 B.1 from 5.8 parts by weight of 4-chloro-C-phenylglycine and 6.8 parts by weight of 1-chlorocarbonyl-3-methylsulphonyl-imidazolid-2-one.
Melting point = 190°C.
Yield: 88%.

Calculated: C, 41.6; H, 3.7; Cl, 9.4; N, 11.2; S, 8.5.
Found: C, 40.8; H, 3.7; Cl, 9.2; N, 11.1; S, 8.9.
IR-bands at 3700-2200, 3310, 1730, 1654, 1540 and 1168 cm⁻¹ (in Nujol).
NMR-signals at τ = 1.1 (1H), 2.55 (4H), 4.5 (1H), 6.1 (4H) and 6.65 ppm (3H).

3.
D,L-α-[(3-methylsulphonyl-imidazolidin-2-on-1-yl)carbonylamino]-α-thienyl-(2)-acetic acid

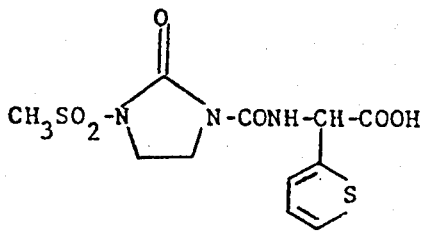

This carboxylic acid was produced as described in Example 39B.1 from 5.5 parts by weight of α-thienyl-(2)-glycine and 6.8 parts by weight of 1-chloro-carbonyl-3-methylsulphonylimidazolid-2-one.
Yield: 88%.
Melting point approx: 110°C, crude product.
Calculated: C, 38.0; H, 3.8; N, 12.1; S, 18.4.
Found: C, 38.2; H, 4.8; N, 10.8; S, 17.0.
IR-bands at 3600–2200, 3315, 1740, 1725, 1664, 1525 and 1170 cm⁻¹ (in Nujol).
NMR-signals at τ = 1.2 (1H), 2.4–3.1 (3H), 4.2 (1H), 6.07 (4H) and 6.67 ppm (3H).

4.
L(+)-α-[(3-methylsulphonyl-imidazolidin-2-on-1-yl)-carbonylamino]-phenylacetic acid

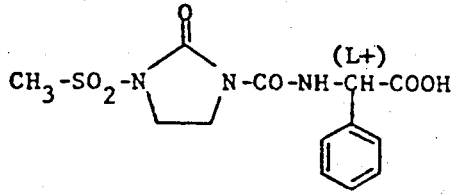

This carboxylic acid was produced as described in Example 39 B.1 from 5.3 parts by weight of L(+)-C-phenylglycine and 6.8 parts by weight of 1-chlorocarbonyl-3-methylsulphonyl-imidazolid-2-one.
Melting point: +245° C
Calculated: C, 45.7; H, 4.4; N, 12.3; S, 9.4.
Found: C, 44.9; H, 4.5; N, 11.9; S, 9.4.
The IR- and NMR-spectra are identical with those of the product from Example 39 B.1.

5.
D,L-α-[(3-methylsulphonyl-imidazolidin-2-on-1-yl)-carbonylamino]-2,6-dichlorophenylacetic acid

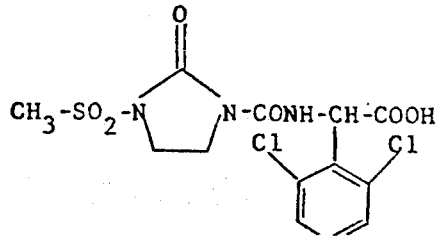

This carboxylic acid was produced as described in Example 39 B.1 from 7.7 parts by weight of 2,6-dichloro-C-phenylglycine and 6.8 parts by weight of 1-chlorocarbonyl-3-methylsulphonyl-imidazolid-2-one.
Melting point: > 260° C
Yield: 69%
IR-bands at 3400–2200, 3290, 1742, 1714, 1646, 1580, 1522 1260, 1170, 1130, 783 and 763 cm$^{-1}$ (in Nujol).
NMR-signals at $\tau = 0.9$ (h), 2.4–2.65(3H), 3.4 (1H), 5.8–6.2 (4H) and 6.65 ppm (3H).

6.
L(+)-α-[(3-acetyl-imidazolidin-2-on-1-yl)-carbonylamino]-phenylacetic acid:

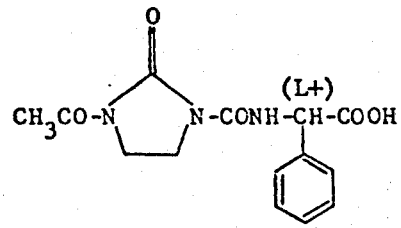

This carboxylic acid was produced as described in Example 39 B.1 from 5.0 parts by weight of L(+)-C-phenylglycine and 5.7 parts by weight of 1-chlorocarbonyl-3-acetylimidazolid-2-one.
Melting point = 214° C
Yield: 69%
Calculated: C,55.0; H, 4.9; N, 13.8.
Found C(53.5); H, 5.2; N, 13.7.
IR-bands at 3650–2250, 3300, 1735, 1665 and 1252 cm$^{-1}$ (in Nujol).
NMR-signals at $\tau$ = 1.0 (1H), 2.3–2.8 (5H), 4.5 (1H), 6.2 (4H) and 7.6 ppm (3H).

7.
D,L-α-[(3-acetyl-imidazolidin-2-on-1-yl)-carbonylamino]-4-chloro-phenylacetic acid:

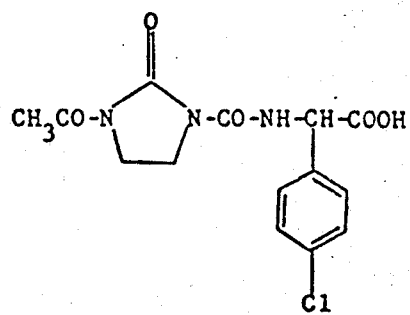

This carboxylic acid was produced as described in Example 39 B.1 from 6.2 parts by weight of D,L-4-chloro-C-phenylglycine and 5.7 parts by weight of 1-chlorocarbonyl-3-acetyl-imidazolid-2-one.
Melting point: 194° C
Yield: 53%
Calculated: C, 49.5; H, 4.1; Cl, 10.4; N, 12.4.
Found: C, 49.6; H, 4.6; Cl, 9.4; N, 12.2.
IR-bands at 3700–2300, 3290, 1725, 1685, 1648 and 1252 cm$^{-1}$ (in Nujol).
NMR signals at $\tau = 0.9$ (1H, 2.55 (4H), 4.45 (1H), 6.2 (4H) and 7.55 ppm (3H).

8.
D,L-α-[(3-acetyl-imidazolidin-2-on-1-yl)-carbonylamino]-4-methylphenylacetic acid:

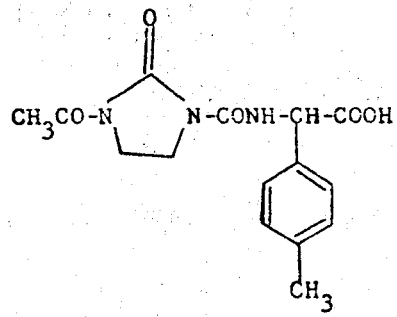

This carboxylic acid was produced as described in Example 39 B.1 from 5.4 parts by weight of 4-methyl-C-phenylglycine and 5.7 parts by weight of 1-chlorocarbonyl-3-acetylimidazolid-2-one.
Yield: 42%
IR-bands at 3600–2200, 3310, 1738, 1712, 1678, 1666 and 1256 cm$^{-1}$ (in Nujol).
NRM-signals at = 1.0 (1H), 2.6 (2H), 2.8 (2H), 4.5 (1H), 6.2 (4H), 7.6 (3H) and 7.7 ppm (3H) (in acetone-d$_6$).

9.
D,L-α-[(3-acetyl-imidazolidin-2-on-1-yl)-carbonylamino]-α-thienyl-(2)-acetic acid:

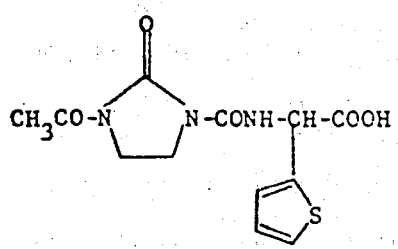

This carboxylic acid was produced as described in Example 39 B.1 from 8.6 parts by weight of thienyl-(2)-acetic and 9.5 parts by weight of 1-chlorocarbonyl-3-acetyl-imidazolid-2-one.
Melting point 197° C
Yield: 62%
Calculated: C, 46.3; H, 4.2; N, 13.5; S, 10.3.
Found: C, 47.1; H, 4.4; N, 13.8; S, 9.7.
IR-bands at 3280, 3080, 3450–2300, 1728, 1680, 1652, 1522, 1260 and 705 cm$^{-1}$ (in Nujol).
NMR-signals at $\tau$ = 1.1 (1H), 2.5–3.2 (3H), 4.2 (1H), 6.2 (4H) and 7.6 ppm (3H).

10.
D,L-α-[(3-acetyl-imidazolidin-2-on-1-yl)-carbonylamino]-2,6-dichloro-phenylacetic acid:

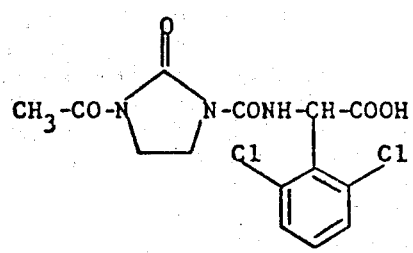

This carboxylic acid was produced as described in Example 39 B.1 from 6.7 parts by weight of 2,6-dichloro-C-phenylglycine and 5.3 parts by weight of 1-chlorocarbonyl-3-acetyl-imidazolid-2-one.
Melting point: = 250° C
Yield: 74%

Calculated: C, 44.9; H, 3.5; Cl, 19.0; N, 11.2.
Found: C, 45.2; H, 3.7; Cl, 18.5; N, 11.4.
IR-bands at 3600–2200, 3302, 1735, 1682, 1625, 1520 and 1255 cm⁻¹ (in Nujol).
NMR-signals at τ = 0.7 (1H), 2.3–2.7 (3H), 3.4 (1H), 6.2 (4H) and 7.6 ppm (3H).

C. 1-Chlorocarbonyl-3-methylsulphonyl-imidazolidone-(2)

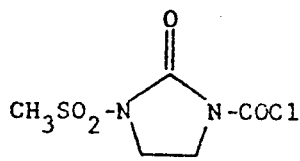

16.4 parts by weight of 1-methylsulphonyl-imidazolidone-(2) in dioxane were boiled for 3 days with 27 parts by weight of trimethylchlorosilane and 20 parts by weight of triethylamine. The triethylamine hydrochloride which had precipitated was filtered off, 11 parts by weight of phosgene were added and the mixture was left to stand overnight at room temperature. Thereafter it was evaporated to dryness and the product was recrystallized from boiling acetone.
Yield 70 %.
Melting point = 178° C
Calculated: C, 26.5; H, 3.1; Cl, 15.7; N, 12.4; S, 14.1.
Found: C, 27.2; H, 3.4; Cl, 15.3; N, 12.0; S, 14.1.
NMR-signals at τ = 5.6 – 6.2 (4H), and 6.6 ppm (3H).
IR-bands at 3010, 1807, 1721, 1360, 1165, 984 and 742 cm⁻¹.

The same product can also be advantageously produced from 1-methylsulphonyl-imidazolid-2-one and excess phosgene in methylene chloride in the presence of pyridine.

D. N-methylsulphonyl-imidazolid-2-one:

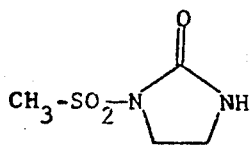

Instructions 1

63 parts by weight of methanesulphochloride were added dropwise at room temperature to a suspension of 43 parts by weight of imidazolid-2-one in 400 parts by volume of dry tetrahydrofurane and the mixture was stirred for 1 hour at 30°–40° C and then heated for 1 hour under reflux. Thereafter, the solvent was distilled off in vacuo and the residue was kept for 1 hour at 60° C, under an oil pump. The residue was recrystallized from warm acetone.
Yield: 25%
Melting poing = 193° C
Calculated: C, 29.3; H, 4.9; N, 17.1; S, 19.5.
Found: C, 29.0; H, 5.0; N, 17.2; S, 19.6.
IR-bands at 3250, 3115, 1715, 1350 and 1160 cm⁻¹.
NMR-signals at τ = 2.4 (1H), 6.2 (2H), 6.5 (2H), and 6.8 ppm (3H).

Instructions 2

80 parts by weight of methanesulphochloride, followed by 56 parts by weight of triethylamine, were added dropwise over the course of 30 minutes to a suspension of 43 parts by weight of imidazolid-2-one in 300 parts by volume of dry tetrahydrofurane, in such a way that the internal temperature was about 35°–40° C. The mixture was stirred for a further 2 hours at 45° C, the solvent was then stripped off in vacuo, the residue which remained was twice extracted with 150 parts by volume of chloroform at a time and the crystals which remained were recrystallized from methanol.
Yield: 49%. According to the melting point and IR-spectrum, the product agrees with the N-methylsulphonylimidazolid-2-one described above.

EXAMPLE 40

Sodium D,L-α-[(3-methylsulphonyl-imidazolidin-2-on-1-yl)-carbonylamino]-4-chlorobenzylpenicillin:

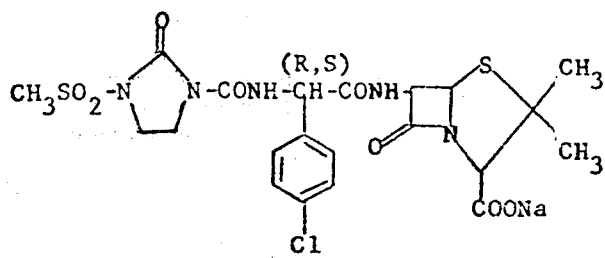

This penicillin was produced as described in Example 39A from 7.5 parts by weight of D,L-α-[(3-methylsulphonyl-imidazolidin-2-on-1-yl)-carbonylamino]-4-chlorophenyl acetic acid, 3.75 parts by weight of tetramethylchloroformamidinium chloride and 4.7 parts by weight of 6-aminopenicillanic acid. Instead of N-methylmorpholine, 2.02 parts by weight of triethylamine were used.
Yield: 65%
β-Lactam content: 62%
According to the NMR-spectrum, the product still contained 24% of methylsulphonylimidazolidonyl-carbonylaminochlorophenyl-acetic acid which was, however, removable by fractional acidification of the aqueous solution of the penicillin sodium salt.
IR-bands at 3310, 1760, 1722, 1670, 1605 and 1170 cm⁻¹ (in Nujol).
NMR-signals at τ = 2.53 (2H), 2.67 (2H), 4.4 (1H), 4.5 (2H), 5.8 (1H), 6.1 (4H), 6.65 (3H) and 8.–8.5 ppm (6H), (in methanol d₄).

EXAMPLE 41

Sodium D,L-α-[(3-methylsulphonyl-imidazolidin-2-on-1-yl)-carbonylamino]-α-thienyl-(2)-methylpenicillin

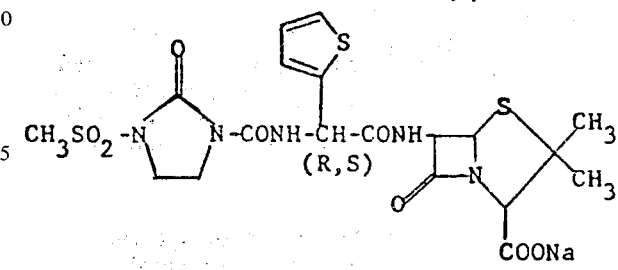

This penicillin was produced as described in Example 39A from 7.0 parts by weight of D,L-α-[(3-methylsulphonyl-imidazolidin-2-on-1-yl)-carbonylamino]-α-thienyl(2)-acetic acid, 3.75 parts by weight of tetramethylchloroformamidinium chloride and 4.8 parts by weight of 6-aminopenicillanic acid.

Yield: 38%

β-Lactam content: 68%

IR-bands at 3310, 1758, 1722, 1650, 1605 and 1170 cm$^{-1}$.

NMR-signals at τ = 2.5–3.1 (3H), 4.1–4.6 (3H), 5.8 (1H), 6.1 (4H), 6.7 (3H) and 8.25–8.5 ppm (6H).

The crude product still contained about 30% of sodium D,L-α-[(3-methylsulphonyl-imidazolidin-2-on-1-yl)-carbonylamino]-α-thienyl-(2)-acetate, which was, however, removable by fractional acidification of the aqueous solution.

EXAMPLE 42

Sodium L(+)-α-[(3-methylsulphonyl-imidazolidin-2-on-1-yl)-carbonylamino]-benzylpenicillin:

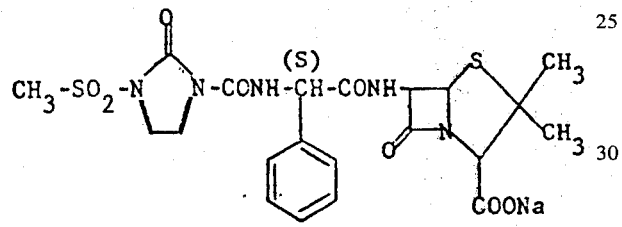

This penicillin was produced as described in Example 39 A from 6.8 parts by weight of L(+)-α-[(3-methylsulphonyl-imidazolidin-2-on-1-yl)-carbonylamino]-phenylacetic acid, 3.75 parts by weight of tetramethylchloroformamidinium chloride and 4.7 parts by weight of 6-aminopenicillanic acid.

Yield: 72%

β-Lactam content: 66%

Calculated: C, 44.1; H, 4.7; N, 11.5; S, 10.6. Found: C, 43.5; H, 5.5; N, 11.5; S, 10.1.

In calculating the analytical values, a water content of 3% and a sodium 2-ethylhexanoate content of 2% were taken into account.

IR-bands at 3310, 1760, 1722, 1665, 1602 and 1168 cm$^{-1}$.

NMR-signals at τ = 2.6 (5H), 4.35–4.8 (3H), 5.8 (1H), 6.2 (4H), 6.7 (3H) and 8.4 ppm (6H).

EXAMPLE 43

Sodium D,L-α-[(3-methylsulphonyl-imidazolidin-2-on-1-yl)-carbonylamino]-2,6-dichloro-benzylpenicillin:

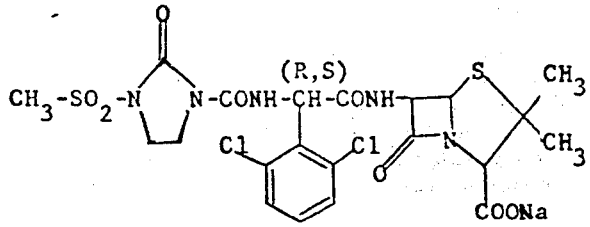

This penicillin was produced as described in Example 39 A from 7.0 parts by weight of D,L-α-[(3-methylsulphonyl-imidazolidin-2-on-1-yl)-carbonylamino]-2,6-di-chlorophenyl acetic acid, 3.2 parts by weight of tetramethylchloroformamidinium chloride and 4.3 parts by weight of 6-aminopenicillanic acid.

However, the reaction of the substituted phenylacetic acid with the tetramethylchlorofomamidinium chloride was not carried out at −40° C, as in Example 39 A, but at −20° C.

Yield: 77%

β-Lactam content: 61.5%

Calculated: C, 38.5; H, 4.0; Cl, 12.2; N 10.0; S 8.7. Found: C, 36.0; H, 4.0; Cl, 12.6; N, 10.5; S, 9.3.

IR-bands at 3310, 1764, 1720, 1678, 1607, 1512, 1255 and 1167 cm$^{-1}$ (in Nujol)

NMR-signals at τ = 2.5–2.9 (3H), 3.8 (1H), 4.45 (2H), 5.8 (1H), 6.15 (4H), 6.7 (3H) and 8.3–8.6 ppm (6H).

In calculating the analytical values, a content of 62% of penicillin, 30% of sodium α-[(3-methylsulphonylimidazolidin-2-on-1-yl)-carbonylamino]-2,6-dichloro-phenylacetate, 4.0% of sodium 2-ethylhexanoate and 3.6% of water was used as the basis. These contents follow from the NMR-spectrum of the crude product. The penicillin can be obtained in the pure form by fractional acidification of the aqueous solution of the crude product.

EXAMPLE 44

A. Sodium L(+)-α-[(3-acetyl-imidazolidin-2-on-1-yl)-carbonylamino]-benzylpenicillin

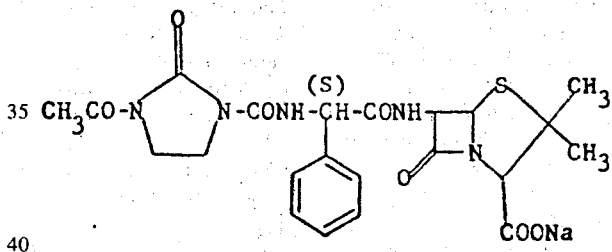

This penicillin was produced as described in Example 39A from 5.0 parts by weight of L(+)-α-[(3-acetylimidazolidin-2-on-1-yl)-carbonylamino]-phenylacetic acid, 3.1 parts by weight of tetramethylchloroformamidinium chloride and 4.3 parts by weight of 6-aminopenicillanic acid.

Yield: 74%

β-Lactam content: 75%

IR-bands at 3305, 1765, 1730, 1675, 1605, 1520 and 1258 cm$^{-1}$ (in Nujol).

NMR-signals at τ = 2.4–2.8 (5H), 4.5–4.8 (3H), 5.8 (1H), 6.22 (4H), 7.5 (3H) and 8.5 ppm (6H).

B. 3-Acetyl-imidazolidin-2-on-1-carbonyl chloride:

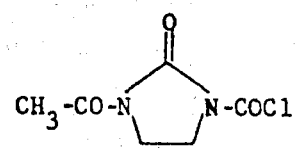

20 parts by weight of N-acetyl-imidazolidone-2 mixed with 25 parts by weight of triethylamine and 150 parts by volume of dry benzene were initially taken and 27 parts by weight of trimethylchlorosilane in 40 parts by volume of benzene were added dropwise over the course of 30 minutes at room temperature, with stiring. Thereafter, the mixture was boiled for 18 hours under reflux with exclusion of moisture, and after cooling the triethylamaine hydrochloride which had precipitated (22 parts by weight = 100%) was filtered off and carefully eluted with dry benzene. The benzene solution thus obtained was treated, at 5° C, with a solution of 17 parts by weight of phosgene in 50 parts by volume of benzene and left to stand overnight at 5° C. Thereafter, the solvent was stripped off in vacuo and the residue was dried under an oil pump. It was recrystallized from an acetone/pentane mixture.

Yield: 81%
Melting point = 104° C
Calculated: C,37.7; H, 3.7; Cl, 18.6; N, 14.7. Found: C, 39.3; H, 4.3; Cl, 17.7; N, 14.7.
IR-bands at 1798, 1740, 1690, and 1660 cm$^{-1}$.
NMR-signals at $\tau$ = 5.65–6.3 (4H) and 7.45 ppm (3H)

According to the NMR-spectrum, the product still contained 5 – 10% of N-acetyl-imidazolone, which however does not interfere in the reaction with C-phenylglycine and other amino-acids (as in Example 39, B6).

C. N-acetyl-imidazolid-2-one

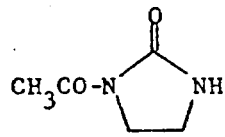

23.6 parts by weight of acetyl chloride in 100 parts by volume of tetrahydrofurane were added dropwise over the course of 60 minutes, at 0° C, to a suspension of 25.8 parts by weight of imidazolone-2 in 350 parts by volume of dry tetrahydrofurane. The mixture was stirred for 3 hours at room temperature and dry air was subsequently blown through the solution for some time; the solvent was then recovered in vacuo and the residue was recrystallized from boiling nitromethane.

Yield: 52%
Melting point 188° C.
Calculated: C, 46.9; H, 6.9; N, 21.9. Found: C, 47.0; H, 6.2; N, 22.5.
IR-bands at 3230, 1730 and 1640 cm$^{-1}$.
NMR-signals at $\tau$ = 6.2 (2H), 6.5 (2H), and 7.6 ppm (3H)

EXAMPLE 45

Sodium D,L-α-[(3-acetylimidazolidin-2-on-1-yl)-carbonylamino]-4-chlorobenzylpenicillin

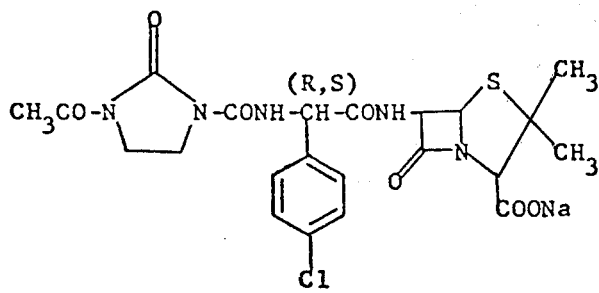

This penicillin was produced as described in Example 39A from 4.0 parts by weight of D,L-α-[(3-acetylimidazolidin-2-on-1-yl)-carbonylamino]-5-chlorophenylacetic acid, 2.2 parts by weight of tetramethylchloroformamidinium chloride and 3.25 parts by weight of 6-aminopenicillanic acid.

Yield: 76%
β-Lactam content: 89%
IR-bands at 3310, 1760, 1730, 1670, 1600, 1518 and 1259 cm$^{-1}$ (in Nujol).
NMR-signals at $\tau$ = 2.4–2.9 (4H), 4.4 (1H), 4.5 (2H), 5.8 (1H), 6.2 (4H), 7.5 (3H), and 8.3–8.5 ppm (6H).

EXAMPLE 46

Sodium D,L-α-[(3-acetyl-imidazolidin-2-on-1-yl)-carbonylamino]-4-methyl-benzylpenicillin:

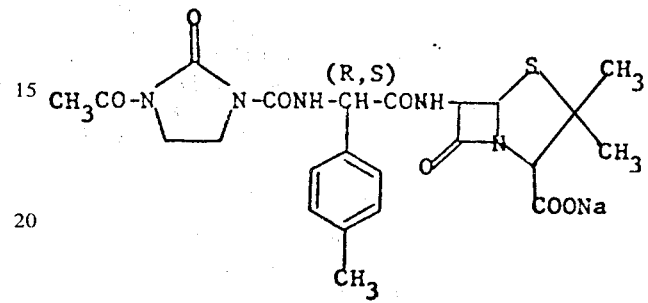

This penicillin was produced as described in Example 39A from 3.2 parts by weight of D,L-α-[(3-acetylimidazolidin-2-on-1-yl)-carbonylamino]-4-methylphenylacetic acid, 1.9 parts by weight of tetramethylchloroformamidinium chloride and 2.6 parts by weight of 6-aminopenicillanic acid.

Yield: 45%
β-Lactam content: 83%
IR-bands at 3305, 1760, 1725, 1672, 1600, 1515 and 1255 cm$^{-1}$ (in Nujol).
NMR-signals at $\tau$ = 2.6–2.8 (4H), 4.4–4.8 (2H), 5.8 (1H), 6.2 (4H), 7.5 (3H), 7.7 (3H) and 8.3–8.6 ppm (6H)

EXAMPLE 47

Sodium D,L-α-[(3-acetyl-imidazolidin-2-on-1-yl)-carbonylamino]-α-thienyl-(2)-methylpenicillin

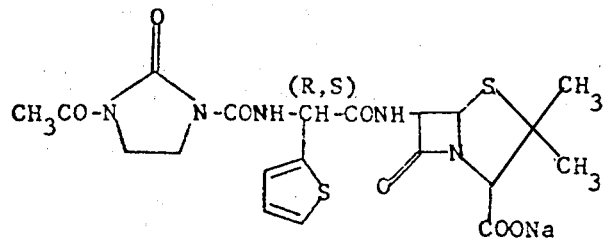

This penicillin was produced as described in Example 39A from 8 parts by weight of D,L-α-[(3-acetylimidazolidin-2-on-1-yl)-carbonylamino]-thienyl-(2)-acetic acid, 4.9 parts by weight of tetramethylchloroformamidinium chloride and 6.5 parts by weight of 6-aminopenicillanic acid.

Yield: 88%
β-Lactam content: 87%
IR-bands at 3302, 1760, 1732, 1678, 1605, 1520, 1315 and 1261 cm$^{-1}$ (in Nujol).
NMR-signals at $\tau$ = 2.5–3.2 (3H), 4.0–4.5 (3H), 5.8 (1H), 6.2 (4H), 7.5 (3H) and 8.2–8.6 ppm (6H).

EXAMPLE 48

Sodium D,L-α-[(3-acetyl-imidazolidin-2-on-1-yl)-carbonylamino]-2,6-dichloro-benzylpenicillin

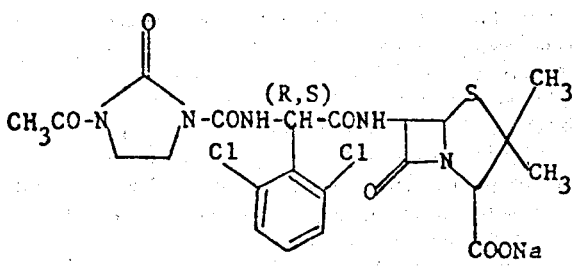

This penicillin was produced as described in Example 39A from 6.5 parts by weight of D,L-α-[(3-acetylimidazolidin-2-on-1-yl)-carbonylamino]-2,6-dichlorophenylacetic acid, 3.2 parts by weight of tetramethylchloroformamidinium chloride and 4.3 parts by weight of 6-aminopenicillanic acid. The reaction of the substituted phenylacetic acid with the tetramethylchloroformamidinium chloride was carried out at −10° C.

Yield: 29%

β-Lactam content: 66%

IR-bands at 3310, 1765, 1735, 1685, 1615, 1520, 1265, 1100, 1028 and 805 cm$^{-1}$ (in Nujol).

NMR-signals at = 2.7 (3H), 3.8 (1H), 4.3–4.6 (2H), 5.8 (1H), 6.2 (4H), 7.5 (3H) and 8.2–8.6 ppm (6H).

According to the NMR-spectrum, the crude product contained 27% of sodium D,L-α-[(3-acetyl-imidazolidin-2-on-1-yl)-carbonylamino]-2,6-dichloro-phenylacetate, which is removable from the product by fractional acidification of the aqueous solution.

EXAMPLE 49

Sodium D(−)-α-[(3-ethylsulphonyl-imidazolidin-2-on-1-yl)-carbonylamino]-benzylpenicillin

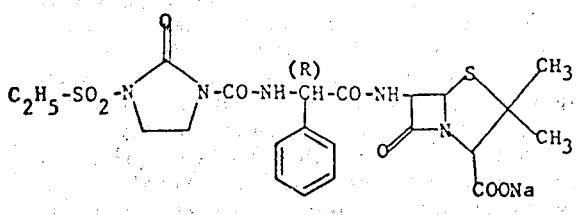

2.9 parts by weight of D(−)-α-[(3-ethylsulphonylimidazolidin-2-on-1-yl)-carbonylamino]-phenylacetic acid (the substance contained 1 mol of isopropanol and 1 mol of H$_2$O on the crystal) were dissolved in 30 parts by volume of tetrahydrofurane. The solution was then cooled to −30° C and combined with a solution, cooled to −40° C, of 1.6 parts by weight of tetramethylchloroformamidinium chloride in 30 parts by volume of dichloromethane. Thereafter the mixture was brought to −25° C, and 0.9 part by weight of N-methylmorpholine were added followed, after 3 minutes, by a mixture, cooled to −5° C, of 2.3 parts by weight of 6-aminopenicillanic acid and 25 parts by volume of 90% strength aqueous tetrahydrofurane, which was adjusted to pH 2.5 with approximately 10% strength hydrochloric acid. Thereafter the temperature was allowed to rise to 0° C and the pH of the mixture was kept at 2.5 by appropriate addition of N-methylmorpholine or dilute sodium hydroxide solution. After 1 hour, no further addition of base was necessary to maintain the pH of 2.5. The mixture was then adjusted to pH 7.0, the bulk of the tetrahydrofurane was removed in vacuo and the remaining aqueous phase was extracted once by shaking with ether (the ether phase being discarded), covered with ether-ethylacetate mixture and acidified to pH 1.5. The organic phase was separated off, washed with water and dried for 1 hour over MgSO$_4$ at 0° C. The drying agent was then removed and the sodium salt of the penicillin was precipitated with a solution of sodium 2-ethylhexanoate in ether containing methanol.

Yield: 3.2 parts by weight

β-Lactam content: 81.9%

NMR-signals at τ = 2.4–2.85 (5H), 4.4–4.8 (3H), 5.8 (1H), 6.15 (4H), 6.3–6.7 (2H) and 8.3–8.8 ppm (9H).

D(−)-α-[(3-ethylsulphonyl-imidazolidin-2-on-1-yl)-carbonylamino]-phenylacetic acid

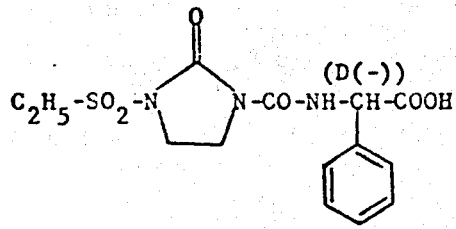

4.5 parts by weight of 3-ethylsulphonyl-imidazolidin-2-one-1-carbonyl chloride were added at about 0° C to a solution of 5.5 parts by weight of D(−)-bis-trimethylsilyl-α-aminophenyl-acetic acid in 40 parts by volume of tetrachloromethane. The mixture was then left to stand for 4 hours at 20° C; the solvent was then stripped off and the residue was thoroughly worked with 1 N HCl in a mortar. The solid product was filtered off, washed with water, dried and recrystallized from isopropanol.

Yield: 6.0 parts by weight.

Melting point = 102° (re-solidifies, and then:) melting point = 211° (heating bench).

The content of 1 mol of isopropanol and 1 mol of H$_2$O was taken into account in the calculated analytical data.

Calculated: C, 47.1, H, 6.3; N, 9.7; S, 7.4

Found: C, 47.1; H, 5.7; N, 9.7; S, 7.6

NMR-signals at τ = 2.6 (5H), 4.6 (1H), 6.1 (4H), 6.3–6.7 (2H) and 8.5–8.7 ppm (3H).

3-Ethylsulphonyl-imidazolidin-2-one-1-carbonyl chloride

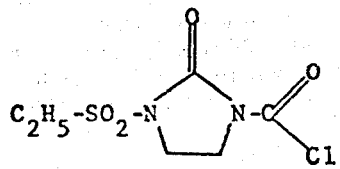

This product was produced from 3-ethylsulphonyl-imidazolidin-2-one and phosgene in dichloromethane and in the presence of pyridine, at 20° C.

Melting point = 174°

Calculated: C, 29.9; H, 3.8; Cl, 14.8; N, 11.6; S, 13.3.

Found: C, 30.1; H, 3.8; Cl, 14.7; N, 11.8; S, 13.3.

NMR-signals at τ = 5.5–6.1 (4H), 6.2–6.65 (2H) and 8.4–8.75 ppm (3H).

1-Ethylsulphonyl-imidazolidin-2-one

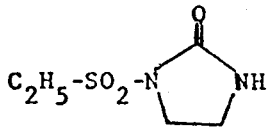

This substance was obtained by heating molar amounts of imidazolidin-2-one and ethylsulphonyl chloride at 150° to 180° (until the evolution of HCl had ceased). The pure substance was isolated by extraction with hot benzene, acetone and ethyl acetate from the crude product, and recrystallization from acetone (with addition of active charcoal).

Melting point = 114°
Calculated: C, 33.7; H, 5.7; N, 15.7; S, 18.0.
Found: C, 33.1; H, 5.7; N, 16.3; S, 17.7.
NMR-signals at $\tau$ = 5.9–6.7 (6H) and 8.5–8.8 ppm (3H).

EXAMPLE 50

Sodium
D(−)-α-[(3-ethylsulphonyl-imidazolidin-2-on-1-yl)-carbonylamino]-benzylpenicillin:

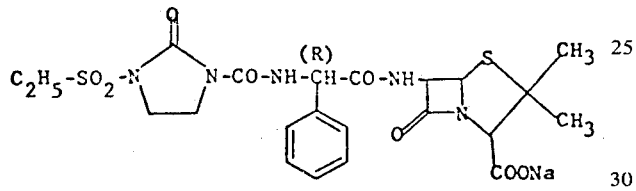

A solution of 8.6 parts by weight of D(−)-bis-trimethyl-silyl-α-aminophenylacetic acid in dichloromethane was cooled to 0° C, a solution of 7.0 parts by weight of 3-ethylsulphonyl-imidazolidin-2-one-1-carbonyl chloride in 15 parts by volume of dichloromethane was then added dropwise with further cooling, and the mixture was subsequently left to stand overnight at 0° C. A solution of 5.0 parts by weight of tetramethylchloroformamidinium chloride in 15 parts by volume of dichloromethane was then added and the mixture was left to stand for 1 hour at 0° C. This reaction mixture was then introduced dropwise into a suspension, cooled to 0° C and adjusted to pH 2.5 with dilute hydrochloric acid, of 8.2 parts by weight of 6-aminopenicillanic acid in 85 parts by volume of 80% strength aqueous tetrahydrofurane and at the same time the pH was kept at 2.5 by appropriate addition of dilute NaOH. The mixture was then stirred for a further hour at 0° C and during stirring the pH was kept at 2.5 by further addition of dilute sodium hydroxide solution where necessary. The pH was now adjusted to 7.0, the volatile organic solvents were removed in vacuo and the sodium salt of the penicillin was isolated in the manner described in the preceding example.

Yield: 8.0 parts by weight
β-Lactam content: 58%

EXAMPLE 51

Sodium
α-[(3-ethylsulphonyl-imidazolidin-2-on-1-yl)-carbonylamino]-p-chlorobenzylpenicillin:

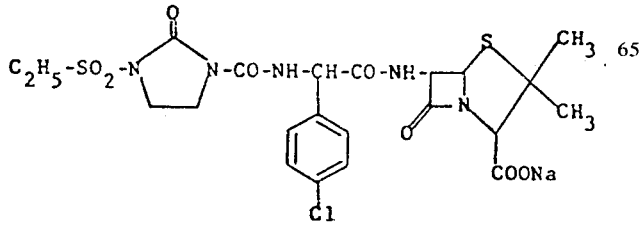

This penicillin was produced as described in Example 49 from 4.5 parts by weight of α-[(3-ethyl-sulphonylimidazolidin-2-on-1-yl)-carbonylamino]-p-chlorophenylacetic acid, 2.3 parts by weight of tetramethylchloroformamidinium chloride, 1.3 parts by weight of N-methylmorpholine and 3.2 parts by weight of 6-aminopenicillanic acid. However, the coupling with 6-aminopenicillanic acid was effected not aftr 3 minutes but after 6 minutes.

Yield: 4.4 parts by weight
IR-bands at 3300, 1765, 1725, 1670, 1600, 1500–1520, 1260, 1165, 1130 cm$^{-1}$ (Nujol).

α[(3-Ethylsulphonyl-imidazolidin-2-on-1-yl)-carbonylamino]-p-chlorophenylacetic acid:

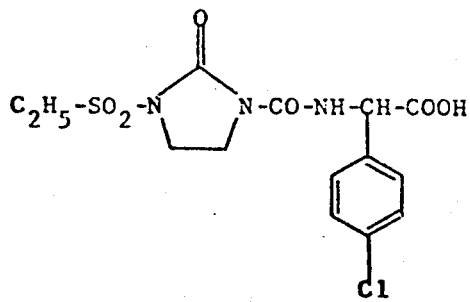

Sufficient concentrated sodium hydroxide solution just to dissolve the acid was added to a suspension of 11.0 parts by weight of p-chloro-α-aminophenylacetic acid in 110 parts by volume of 50% strength aqueous dioxane. Dilute hydrochloric acid was then added with stirring until a pH of 7.5–8.0 was reached. 13.0 parts by weight of 3-ethylsulphonyl-imidazolidin-2-one-1-carbonyl chloride were then added in portions at about 0° C and the pH of the mixture was maintained at 7.5–8.0 by means of dilute sodium hydroxide solution. Thereafter the mixture was stirred further for as long as an occasional addition of sodium hydroxide solution was still necessary to maintain the pH of 7.5–8.0. The bulk of the dioxane was then removed in vacuo at pH 6.5, about 200 parts by volume of water were added, the mixture was extracted once with ether at pH 9.0 (the ether extract being discarded) and covered with fresh ether, and the pH was brought to 0.5 with stirring. The organic phase was then separated off, washed, dried and completely evaporated in vacuo. The residue was dissolved in hot ethyl acetate; thereafter the same amount of benzene and petroleum ether was added until there is turbidity which (only just) disappears again, and the mixture was left to crystallize.

Yield: 4.9 parts by weight.
Melting point = 168° C
NMR-signals at $\tau$ = 2.6 (4H), 4.6 (1H), 6.1 (4H), 6.3–6.7 (2H) and 8.4–8.8 ppm (3H).
IR-bands at 3300, 1720, 1650, 1540, 1350 and 1160 cm$^{-1}$ (Nujol).

EXAMPLE 52

If, in the manner described in Example 39A 0.02 mol of:

D(−)-α-[(3-methylsulphonyl-imidazolidin-2-on-1-yl)-carbonylamino]-4-chlorophenylacetic acid,
D(−)-α-[(3-methylsulphonyl-imidazolidin-2-on-1-yl)-carbonylamino]-4-methylphenylacetic acid,
D(−)-α-[(3-methylsulphonyl-imidazolidin-2-on-1-yl)-carbonylamino]-4-nitrophenylacetic acid,
D(−)-α-[(3-methylsulphonyl-imidazolidin-2-on-1-yl)-carbonylamino]-4-hydroxyphenylacetic acid,
D(−)-α-[(3-methylsulphonyl-imidazolidin-2-on-1-yl)-carbonylamino]-thienyl-(2)-acetic acid D,L-α-[(3-methylsulphonyl-imidazolidin-2-on-1-yl)-carbonylamino]-4-methylsulphonyl-phenylacetic acid,
D(−)-α-[(3-ethylsulphonyl-imidazolidin-2-on-1-yl)-carbonylamino]-4-chlorophenylacetic acid,
D(−)-α-[(3-ethylsulphonyl-imidazolidin-2-on-1-yl)-carbonylamino]-4-methyl-phenylacetic acid,
D(−)-α-[(3-ethylsulphonyl-imidazolidin-2-on-yl)-carbonylamino]-4-nitrophenylacetic acid,
D(−)-α-[(3-ethylsulphonyl-imidazolidin-2-on-yl)-carbonylamino]-4-hydroxyphenylacetic acid,
D(−)-α-[(3-ethylsulphonyl-imidazolidin-2-on-yl)-carbonylamino]-thienyl-(2)-acetic acid,
D,L-α-[(3-ethylsulphonyl-imidazolidin-2-on-yl)-carbonylamino]-4-methylsulphonyl-phenylacetic acid,
D(−)-α-[(3-acetyl-imidazolidin-2-on-1-yl)-carbonylamino]-4-chlorophenylacetic acid,
D(−)-α-[(3-acetyl-imidazolidin-2-on-1-yl)-carbonylamino]-4-methylphenylacetic acid,
D(−)-α-[(3-acetyl-imidazolidin-2-on-1-yl)-carbonylamino]-4-nitrophenylacetic acid,
D(−)-α-[(3-acetyl-imidazolidin-2-on-1-yl)-carbonylamino]-4-hydroxyphenylacetic acid,
D(−)-α-[(3-acetyl-imidazolidin-2-on-1-yl)-carbonylamino]-thienyl-(2)-acetic acid,
D,L-α-[(3-acetyl-imidazolidin-2-on-1-yl)-carbonylamino]-4-methylsulphonyl-phenylacetic acid,
D(−)-α-[(3-formyl-imidazolidin-2-on-1-yl)-carbonylamino]-4-chlorophenylacetic acid,
D(−)-α-[(3-formyl-imidazolidin-2-on-1-yl)-carbonylamino]-4-methylphenylacetic acid,
D(−)-α-[(3-formyl-imidazolidin-2-on-1-yl)-carbonylamino]-4-nitrophenylacetic acid,
D(−)-α-[(3-formyl-imidazolidin-2-on-1-yl)-carbonylamino]-4-hydroxyphenylacetic acid,
D(−)-α-[(3-formyl-imidazolidin-2-on-1-yl)-carbonylamino]-4-thienyl-(2)-acetic acid,
D,L-α-[(3-formyl-imidazolidin-2-on-1-yl)-carbonylamino]-4-methylsulphonyl-phenylacetic acid,
D(−)-α-[(3-furoyl-(2)-imidazolidin-2-on-1-yl)-carbonylamino]-4-chlorophenylacetic acid,
D(−)-α-[(3-furoyl-(2)-imidazolidin-2-on-1-yl)-carbonylamino]-4-methylphenylacetic acid,
D(−)-α-[(3-furoyl-(2)-imidazolidin-2-on-1-yl)-carbonylamino]-4-nitrophenylacetic acid,
D(−)-α-[(3-furoyl-(2)-imidazolidin-2-on-1-yl)-carbonylamino]-4-hydroxyphenylacetic acid,
D(−)-α-[(3-furoyl-(2)-imidazolidin-2-on-1-yl)-carbonylamino]-thienyl-(2)-acetic acid,
D,L-α-[(3-furoyl-(2)-imidazolidin-2-on-1-yl)-carbonylamino]-4-methylsulphonyl-phenylacetic acid,
D(−)-α-[(3-benzoyl-imidazolidin-2-on-1-yl)-carbonylamino]-4-chlorophenylacetic acid,
D(−)-α-[(3-benzoyl-imidazolidin-2-on-1-yl)-carbonylamino]-4-methylphenylacetic acid,
D(−)-α-[(3-benzoyl-imidazolidin-2-on-1-yl)-carbonylamino]-4-nitrophenylacetic acid,
D(−)-α-[(3-benzoyl-imidazolidin-2-on-1-yl)-carbonylamino]-4-hydroxyphenylacetic acid,
D(−)-α-[(3-benzoyl-imidazolidin-2-on-1-yl)-carbonylamino]-thienyl-(2)-acetic acid, or
D,L-α-[(3-benzoyl-imidazolidin-2-on-1-yl)-carbonylamino]-4-methylsulphonyl-phenylacetic acid
is reacted with 0.02 mol of tetramethylchloroformamidinium chloride and 0.022 mol of 6-aminopenicillanic acid, the following penicillins are obtained in the form of their sodium salts:
D(−)-α-[(3-methylsulphonyl-imidazolidin-2-on-1-yl)-carbonylamino]-4-chloro-benzylpenicillin,
D(−)-α-[(3-methylsulphonyl-imidazolidin-2-on-1-yl)-carbonylamino]-4-methyl-benzylpenicillin,
D(−)-α-[(3-methylsulphonyl-imidazolidin-2-on-1-yl)-carbonylamino]-4-nitro-benzylpenicillin,
D(−)-α-[(3-methylsulphonyl-imidazolidin-2-on-1-yl)-carbonylamino]-4-hydroxy-benzylpenicillin,
D(−)-α-[(3-methylsulphonyl-imidazolidin-2-on-1-yl)-carbonylamino]-α-thienyl-(2)-methylpenicillin,
D,L-α-[(3-methylsulphonyl-imidazolidin-2-on-1-yl)-carbonylamino]-4-methylsulphonyl-benzylpenicillin,
D(−)-α-[(3-ethylsulphonyl-imidazolidin-2-on-1-yl)-carbonylamino]-4-chloro-benzylpenicillin,
D(−)-α-[(3-ethylsulphonyl-imidazolidin-2-on-1-yl)-carbonylamino]-4-methyl-benzylpenicillin,
D(−)-α-[(3-ethylsulphonyl-imidazolidin-2-on-1-yl)-carbonylamino]-4-nitro-benzylpenicillin,
D(−)-α-[(3-ethylsulphonyl-imidazolidin-2-on-1-yl)-carbonylamino]-4-hydroxy-benzylpenicillin,
D(−)-α-[(3-ethylsulphonyl-imidazolidin-2-on-1-yl)-carbonylamino]-α-thienyl-(2)-methylpenicillin,
D,L-α-[(3-ethylsulphonyl-imidazolidin-2-on-1-yl)-carbonylamino]-4-methylsulphonyl-benzylpenicillin,
D(−)-α-[(3-acetyl-imidazolidin-2-on-1-yl)-carbonylamino]-4-chloro-benzylpenicillin,
D(−)-α-[(3-acetyl-imidazolidin-2-on-1-yl)-carbonylamino]-4-methyl-benzylpenicillin,
D(−)-α-[(3-acetyl-imidazolidin-2-on-1-yl)-carbonylamino]-4-nitro-benzylpenicillin,
D(−)-α-[(3-acetyl-imidazolidin-2-on-1-yl)-carbonylamino]-4-hydroxy-benzylpenicillin,
D(−)-α-[(3-acetyl-imidazolidin-2-on-1-yl)-carbonylamino]-α-thienyl-(2)-methylpenicillin,
D,L-α-[(3-acetyl-imidazolidin-2-on-1-yl)-carbonylamino]-4-methylsulphonyl-benzylpenicillin,
D(−)-α-[(3-formyl-imidazolidin-2-on-1-yl)-carbonylamino]-4-chloro-benzylpenicillin,
D(−)-α-[(3-formyl-imidazolidin-2-on-1-yl)-carbonylamino]-4-methyl-benzylpenicillin,
D(−)-α-[(3-formyl-imidazolidin-2-on-1-yl)-carbonylamino]-4-nitro-benzylpenicillin,
D(−)-α-[(3-formylimidazolidin-2-on-1-yl)-carbonylamino]-4-hydroxy-benzylpenicillin,
D(−)-α-[(3-formyl-imidazolidin-2-on-1-yl)-carbonylamino]-α-thienyl-(2)-methylpenicillin,
D,L-α-[(3-formyl-imidazolidin-2-on-1-yl)-carbonylamino]-4-methylsulphonyl-benzylpenicillin,
D(−)-α-[(3-furoyl(2)-imidazolidin-2-on-1-yl)-carbonylamino]-4-chloro-benzylpenicillin,
D(−)-α-[(3-furoyl(2)-imidazolidin-2-on-1-yl)-carbonylamino]-4-methyl-benzylpenicillin,
D(−)-α-[(3-furoyl(2)-imidazolidin-2-on-1-yl)-carbonylamino]-4-nitro-benzylpenicillin,
D(−)-α-[(3-furoyl(2)-imidazolidin-2-on-1-yl)-carbonylamino]-4-hydroxy-benzylpenicillin,
D(−)-α-[(3-furoyl(2)-imidazolidin-2-on-1-yl)-carbonylamino]-α-thienyl(2)-methylpenicillin,
D,L-α-[(3-furoyl(2)-imidazolidin-2-on-1-yl)-carbonylamino]-4-methylsulphonyl-benzylpenicillin,
D(−)-α-[(3-benzoyl-imidazolidin-2-on-1-yl)-carbonylamino]-4-chloro-benzylpenicillin,
D(−)-α-[(3-benzoyl-imidazolidin-2-on-1-yl)-carbonylamino]-4-methyl-benzylpenicillin,
D(−)-α-[(3-benzoyl-imidazolidin-2-on-1-yl)-carbonylamino]-4-nitro-benzylpenicillin,
D(−)-α-[(3-benzoyl-imidazolidin-2-on-1-yl)-carbonylamino]-4-hydroxy-benzylpenicillin,
D(−)-α-[(3-benzoyl-imidazolidin-2-on-1-yl)-carbonylamino]-α-thienyl(2)-methylpenicillin, or
D,L-α-[(3-benzoyl-imidazolidin-2-on-1-yl)-carbonylamino]-4-methylsulphonyl-benzylpenicillin.

EXAMPLE 53

If, as described in Example 39A 0.02 mol of
D(−)-α-[(3methylaminocarbonyl-imidazolidin-2-on-1-yl)carbonylamino]-phenylacetic acid,
D(−)-α-[(3-aminocarbonyl-imidazolidin-2-on-1-yl)-carbonylamino]-phenylacetic acid,
D(−)-α-[(3-dimethylaminocarbonyl-imidazolidin-2-on-1-yl)-carbonylamino]-phenylacetic acid,
D(−)-α-[(3-i-propyloxycarbonyl-imidazolidin-2-on-1-yl)carbonylamino]-phenylacetic acid,
D(−)-α-[(3-pyrrolid-1-yl-carbonyl-imidazolidin-2-on-1-yl)carbonylamino]-phenylacetic acid,
D(−)-α-[(3-piperid-1-yl-carbonyl-imidazolidin-2-on-1-yl)carbonylamino]-phenylacetic acid,
D(−)-α-[(3-phenylaminocarbonyl-imidazolidin-2-on-1-yl)-carbonylamino]-phenylacetic acid,
D(−)-α-[(3-phenoxycarbonyl-imidazolidin-2-on-1-yl)-carbonylamino]-phenylacetic acid,
D(−)-α-[(3-benzoyl-imidazolidin-2-on-1-yl)-carbonylamino]-phenylacetic acid,
D(−)-α-[(3-furoyl(2)-imidazolidin-2-on-1-yl)-carbonylamino]-phenylacetic acid,
D(−)-α-[(3-n-butyryl-imidazolidin-2-on-1-yl)-carbonylamino]-phenylacetic acid,
D(−)-α-[(2-methylsulphonylamino-4,5-dihydro-imidazol-1-yl)-carbonylamino]-phenylacetic acid,
D(−)-α-[(3-ethylsulphonyl-imidazolidin-2-on-1yl)-carbonylamino]-phenylacetic acid,
D(−)-α-[(3-formyl-imidazolidin-2-on-1-yl-carbonylamino]-phenylacetic acid,
D(−)-α-[(3-pivaloyl-imidazolidin-2-on-1-yl)-carbonylamino]-phenylacetic acid,
D(−)-α-[(3-ethoxycarbonylamino-sulphonyl-imidazolidin-2-on-1-yl)-carbonylamino]-phenylacetic acid,
D(−)-α-[(3-cyclohexyloxycarbonyl-imidazolidin-2-on-1-yl)- carbonylamino]-phenylacetic acid,
D(−)-α-[(3-methylsulphonyl-4-methyl-imidazolidin-2-on-1-yl)-carbonylamino]-phenylacetic acid or
D(−)-α-[(3-methylsulphonyl-5-methyl-imidazolidin-2-on-1-yl)-carbonylamino]-phenylacetic acid
is reacted with 0.02 mol of tetramethylchloroformamidinium chloride and subsequently with 0.022 mol of 6-aminopenicillanic acid, the following penicillins are obtained in the form of their sodium salts:
D(−)-α-[(3-methylaminocarbonyl-imidazolidin-2-on-1-yl)-carbonylamino]-benzylpenicillin,
D(−)--[(3-aminocarbonyl-imidazolidin-2-on-1-yl)-carbonylamino]-benzylpenicillin,
D(−)-α-[(3-dimethylaminocarbonyl-imidazolidin-2-on-1-yl)-carbonylamino]-benzylpenicillin,
D(−)-α-[(3-i-propyloxycarbonyl-imidazolidine-2-on-1-yl)-carbonylamino]-benzylpenicillin,
D(−)-α-[(3-pyrrolid-1-yl-carbonyl-imidazolidin-2-on-1-yl)-carbonylamino]-benzylpenicillin,
D(−)-α-[(3-piperidid-1-yl-carbonyl-imidazolidin-2-on-1-yl)-carbonylamino]-benzylpenicillin,
D(−)-α-[(3-phenylaminocarbonyl-imidazolidin-2-on-1-yl)-carbonylamino]-benzylpenicillin,
D(−)-α-[(3-phenoxycarbonyl-imidazolidin-2-on-1-yl)-carbonylamino]-benzylpenicillin,
D(−)-α-[(3-benzoyl-imidazolidin-2-on-1-yl)-carbonylamino]-benzylpenicillin,
D(−)-α-[(3-furoyl(2)-imidazolidin-2-on-1-yl)-carbonylamino]-benzylpenicillin,
D(−)-α-[(3-butyryl-imidazolidin-2-on-1-yl)-carbonylamino]-benzylpenicillin,
D(−)-α-[(2-methylsulphonylamino-4,5-dihydro-imidazol-1-yl)-carbonylamino]-benzylpenicillin,
D(−)-α-[(3-ethylsulphonyl-imidazolidin-2-on-1-yl)-carbonylamino]-benzylpenicillin,
D(−)-α-[(3-formyl-imidazolidin-2-on-1-yl)-carbonylamino]-benzylpenicillin,
D(−)-α-[(3-pivaloyl-imidazolidin-2-on-1-yl)-carbonylamino]-benzylpenicillin,
D(−)-α-[(3-ethoxy-carbonylamino-sulphonyl-imidazolidin-2-on-1-yl)-carbonylamino]-benzylpenicillin,
D(−)-α-[(3-cyclohexyloxycarbonyl-imidazolidin-2-on-1-yl)carbonylamino]-benzylpenicillin,
D(−)-α-[(3-methylsulphonyl-4-methyl-imidazolidin-2-on-1-yl)-carbonylamino]-benzylpenicillin, or
D(−)-α-[(3-methylsulphonyl-5-methyl-imidazolidin-2-on-1-yl)-carbonylamino]-benzylpencillin.

EXAMPLE 54

If, as described in Example 39A 0.02 mol of
D(−)-α-(5-benzoyl-5-methyl-biureido)-phenylacetic acid,
D(−)-α-(5-benzoyl-5-methyl-2-thio-biureido)-phenylacetic acid,
D(−)-α-(5-acetyl-5-methyl-biureido)-phenylacetic acid,
D(−)-α-(5-acetyl-5-methyl-2-thio-biureido)-phenylacetic acid,
D(−)-α-[3-(imidazolidin-2-on-1-yl-carbonyl)-ureido]-phenylacetic acid,
D(−)-α-[3-imidazolidin-2-on-1-yl-carbonyl)-thioureido]-phenylacetic acid,
D(−)-α-(5-dimethylaminocarbonyl-5-methyl-biureido)-phenylacetic acid,
D(−)-α-(5-dimethylaminocarbonyl-5-methyl-2-thio-biureido)-phenylacetic acid,
D(−)-α-(5-methylsulphonyl-5-methyl-biureido)-phenylacetic acid,
D(−)-α-(5-methylsulphonyl-5-methyl-2-thio-biureido)-phenylacetic acid,
D(−)-α-(5-methylaminocarbonyl-5-methyl-biureido)-phenylacetic acid,
D(−)-α-(5-methylaminocarbonyl-5-methyl-2-thio-biureido)-phenylacetic acid,
D(−)-α-(5-furoyl(2)-5-methyl-biureido)-phenylacetic acid,
D(−)-α-(5-furoyl(2)-5-methyl-2-thio-biureido)-phenylacetic acid,
D(−)-α-[3-isothiazolidine-1,1-dioxid-2-yl-carbonyl)-ureido]-phenylacetic acid,
D(−)-α-[3-(isothiazolidine-1,1-dioxid-2-yl-carbonyl)-thioureido]-phenylacetic acid,
D(−)-α-[3-(pyrrolidin-2-on-1-yl-carbonyl)-ureido]-phenylacetic acid or
D(−)-α-(3-(pyrrolidin-2-on-1-yl-carbonyl)-thioureido]-phenylacetic acid
is reacted with 0.02 mol of tetramethylchloroformamidinium chloride and 0.022 mol of 6-aminopenicillanic acid, the following penicillins are obtained in the form of their sodium salts:

D(—)-α-(5-benzoyl-5-methyl-biureido)-benzyl-
penicillin
D(—)-α-(5-benzoyl-5-methyl-2-thio-biureido)-ben-
zylpenicillin,
D(—)-α-(5-acetyl-5-methyl-biureido)-benzylpenicil-
lin,
D(—)-α-(5-acetyl-5-methyl-2-thio-biureido)-benzyl-
penicillin,
D(—)-α-[3-(imidazolidin-2-on-1-yl-carbonyl)-
ureido]-benzylpenicillin,
D(—)-α-[3-(imidazolidin-2-on-1-yl-carbonyl)-thi-
oureido]-benzylpenicillin,
D(—)-α-(5-dimethylaminocarbonyl-5-methyl-
biureido)-benzylpenicillin,
D(—)-α-(5-dimethylaminocarbonyl-5-methyl-2-thio-
biureido)-benzylpenicillin,
D(—)-α-(5-methylsulphonyl-5-methyl-biureido)-ben-
zylpenicillin,
D(—)-α-(5-methylsulphonyl-5-methyl-thio-ureido)-
benzylpenicillin,
D(—)-α-(5-methylaminocarbonyl-5-methyl-
biureido)-benzylpenicillin,
D(—)-α-(5-methylaminocarbonyl-5-methyl-2-thio-
biureido)-benzylpenicillin,
D(—)-α-(5-furoyl(2)-5-methyl-biureido)-benzyl-
penicillin,
D(—)-α-(5-furoyl(2)-5-methyl-2-thio-biureido)-ben-
zylpenicillin,
D(—)-α-[3-(isothiazolidine-1,1-dioxide-2-yl-car-
bonylureido]-benzylpenicillin,
D(—)-α-[3-(isothiazolidine-1,1-dioxide-2-yl-car-
bonyl)thioureido]-benzylpenicillin,
D(—)-α-[3-(pyrrolidin-2-on-1-yl-carbonyl)-ureido]-
benzylpenicillin, or
D(—)-α-[3-(pyrrolidin-2-on-1-yl-carbonyl)-thi-
oureido]-benzylpenicillin.

EXAMPLE 55

If, as described in Example 39A, 0.02 mol of
D(—)-α-[(3-propionyl-imidazolidin-2-on-1-yl)-car-
bonylamino]-phenylacetic acid,
D(—)-α-[(3-acetyl-4-methyl-imidazolidin-2-on-1-yl)-
carbonylamino]-phenylacetic acid,
D(—)-α-[(3-acetyl-5-methyl-imidazolidin-2-on-1yl)-
carbonylamino]-phenylacetic acid,
D(—)-α-[(3-acetyl-1,3-diaza-cyclohexan-2-on-1-yl)-
carbonylamino]-phenylacetic acid,
D(—)-α-[(3-n-propylsulphonyl-imidazolidin-2-on-1-
yl)-carbonylamino]-phenylacetic acid,
D(—)-α-[(3-ethylsulphonyl-4-methyl-imidazolidin-
2-on-1-yl)carbonylamino]-phenylacetic acid,
D(—)-α-[(3-ethylsulphonyl-5-methyl-imidazolidin-
2-on-1yl)carbonylamino]-phenylacetic acid,
D(—)-α-[(3-ethylsulphonyl-1,3-diaza-cyclohexan-
2-on-1-yl)-carbonylamino]-phenylacetic acid,
D(—)-α-[(3-methylsulphonyl-1,3-diaza-cyclohexan-
2-on-1-yl)-carbonylamino]-phenylacetic acid,
D(—)-α-[(3-n-propylsulphonyl-1,3-diaza-cyclohex-
an-2-on-1-yl)-carbonylamino]-phenylacetic acid,
D(—)-α-[(3-i-propylsulphonyl-1,3-diaza-cyclohexan-
2-on-1-yl)-carbonylamino]-phenylacetic acid,
D(—)-α-[(3-i-propylsulphonyl-imidazolidin-2-on-1-
yl)-carbonylamino]-phenylacetic acid,
D(—)-α-[(3-i-propylsulphonyl-4-methyl-imidazoli-
din-2-on-1-yl)-carbonylamino]-phenylacetic acid,
D(—)-α-[(3-i-propylsulphonyl-5-methyl-imidazoli-
din-2-on-1-yl)-carbonylamino]-phenylacetic acid,
D(—)-α-[(3-n-propylsulphonyl-4-methyl-imidazoli-
din-2-on-1-yl)-carbonylamino]-phenylacetic acid,
D(—)-α-[(3-n-propylsulphonyl-5-methyl-imidazoli-
din-2-on-1-yl)-carbonylamino]-phenylacetic acid,
D(—)-α-[(3-phenylsulphonyl-imidazolidin-2-on-1yl)-
carbonylamino]-phenylacetic acid,
D(—)-α-[(3-p-methylphenylsulphonyl-imidazolidin-
2-on-1-yl)-carbonylamino]-phenylacetic acid,
D(—)-α-[(3-cyclohexylsulphonyl-imidazolidin-2-on-
1-yl)-carbonylamino]-phenylacetic acid,
D(—)-α-[(3-thienyl(2)-sulphonyl-imidazolidin-2-on-
1-yl)-carbonylamino]-phenylacetic acid,
D(—)-α-[(3-formyl-4-methyl-imidazolidin-2-on-1-
yl)-carbonylamino]-phenylacetic acid,
D(—)-α-[(3-formyl-5-methyl-imidazolidin-2-on-1-
yl)-carbonylamino]-phenylacetic acid,
D(—)-α-[(3-formyl-1,3-diaza-cyclohexan-2-on-1-yl)-
carbonylamino]-phenylacetic acid,
D(—)-α-[(3-methylaminocarbonyl-4-methyl-
imidazolidin-2-on-1-yl)-carbonylamino]-phenyla-
cetic acid,
D(—)-α-[(3-methylaminocarbonyl-5-methyl-
imidazolidin-2-on-1-yl)-carbonylamino]-phenyla-
cetic acid,
D(—)-α-[(3-methylaminocarbonyl-1,3-diaza-
cyclohexan-2-on-1-yl)-carbonylamino]-phenyla-
cetic acid,
D(—)-α-[(3-methoxycarbonyl-4-methyl-imidazoli-
din-2-on-1-yl)-carbonylamino]-phenylacetic acid,
D(—)-α-[(3-methoxycarbonyl-5-methyl-imidazoli-
din-2-on-1-yl)-carbonylamino]-phenylacetic acid,
D(—)-α-[(3-methoxycarbonyl-1,3-diaza-cyclohexan-
2-on-1-yl)-carbonylamino]-phenylacetic acid,
D(—)-α-[(3-i-propyloxycarbonyl-4-methyl-imidazoli-
din-2-on-1-yl)-carbonylamino]-phenylacetic acid,
D(—)-α-[(3-i-propyloxycarbonyl-5-methyl-imidazoli-
din-2-on-1-yl)-carbonylamino]-phenylacetic acid,
D(—)-α-[(3-i-propyloxycarbonyl-1,3-diaza-cyclohex-
an-2-on-1-yl)-carbonylamino]-phenylacetic acid,
D(—)-α-[(3-methylsulphonyl-4,5-dimethyl-
imidazolidin-2-on-1-yl)-carbonylamino]-phenyla-
cetic acid,
D(—)-α-[(3-methylsulphonyl-4,4-dimethyl-
imidazolidin-2-on-1-yl)-carbonylamino]-phenyla-
cetic acid,
D(—)-α-[(3-methylsulphonyl-5,5-dimethyl-
imidazolidin-2-on-1-yl)-carbonylamino]-phenyla-
cetic acid,
D(—)-α-[(3-formyl-4,5-dimethyl-imidazolidin-2-on-
1-yl)-carbonylamino]-phenylacetic acid,
D(—)-α-[(3-formyl-4,4-dimethyl-imidazolidin-2-on-
1-yl)-carbonylamino]-phenylacetic acid or
D(—)-α-[(3-formyl-5,5-dimethyl-imidazolidin-2-on-
1-yl)-carbonylamino]-phenylacetic acid
is reacted with 0.02 mol of tetramethylchlorofor-
mamidinium chloride and 0.022 mol of 6-aminopenicil-
lanic acid, the following penicillins are obtained in the
form of their sodium salts: D(—)-α-[(3-propionyl-
imidazolidin-2-on-1-yl)-carbonylamino]-benzylpenicil-
lin,
D(—)-α-[(3-acetyl-4-methyl-imidazolidin-2-on-1-yl)-
carbonylamino]-benzylpenicillin,
D(—)-α-[(3-acetyl-5-methyl-imidazolidin-2-on-1-yl)-
carbonylamino]-benzylpenicillin,
D(—)-α-[(3-acetyl-1,3-diaza-cyclohexan-2-on-1-yl)-
carbonylamino]-benzylpenicillin,
D(—)-α-[(3-n-propylsulphonyl-imidazolidin-2-on-1-
yl)-carbonylamino]-benzylpenicillin,
D(—)-α-[(3-ethylsulphonyl-4-methyl-imidazolidin-
2-on-1-yl)-carbonylamino]-benzylpenicillin,
D(—)-α-[(3-ethylsulphonyl-5-methyl-imidazolidin-
2-on-1-yl)-carbonylamino]-benzylpenicillin, D(—)-α-[(3-ethylsulphonyl-1,3-diaza-cyclohexan-2-on-1-yl)-carbonylamino]-benzylpenicillin,
D(—)-α-[(3-methylsulphonyl-1,3-diaza-cyclohexan-2-on-1-yl)-carbonylamino]-benzylpenicillin,
D(—)-α-[(3-n-propylsulphonyl-1,3-diaza-cyclohexan-2-on-1-yl)-carbonylamino]-benzylpenicillin,
D(—)-α-[(3-i-propylsulphonyl-1,3-diaza-cyclohexan-2-on-1-yl)-carbonylamino]-benzylpenicillin,
D(—)-α-[(3-i-propylsulphonyl-imidazolidin-2-on-1-yl)-carbonylamino]-benzylpenicillin,
D(—)-α-[(3-i-propylsulphonyl-4-methyl-imidazolidin-2-on-1-yl)-carbonylamino]-benzylpenicillin,
D(—)-α-[(3-i-propylsulphonyl-5-methyl-imidazolidin-2-on-1-yl)-carbonylamino]-benzylpenicillin,
D(—)-α-[(3-n-propylsulphonyl-4-methyl-imidazolidin-2-on-1-yl)-carbonylamino]-benzylpenicillin,
D(—)-α-[(3-n-propylsulphonyl-5-methyl-imidazolidin-2-on-1-yl)-carbonylamino]-benzylpenicillin,
D(—)-α-[(3-phenylsulphonyl-imidazolidin-2-on-1-yl)-carbonylamino]-benzylpenicillin,
D(—)-α-[(3-p-methylphenylsulphonyl-imidazolidin-2-on-1-yl)-carbonylamino]-benzylpenicillin,
D(—)-α-[(3-cyclohexylsulphonyl-imidazolidin-2-on-1-yl)-carbonylamino]-benzylpenicillin,
D(—)-α-[(3-thienyl(2)-sulphonyl-imidazolidin-2-on-1-yl)-carbonylamino]-benzylpenicillin,
D(—)-α-[(3-formyl-4-methyl-imidazolidin-2-on-1-yl)-carbonylamino]-benzylpenicillin,
D(—)-α-[(3-formyl-5-methyl-imidazolidin-2-on-1-yl)-carbonylamino]-benzylpenicillin,
D(—)-α-[(3-formyl-1,3-diaza-cyclohexan-2-on-1-yl)-carbonylamino]-benzylpenicillin,
D(—)-α-[(3-methylaminocarbonyl-4-methyl-imidazolidin-2-on-1-yl)-carbonylamino]-benzylpenicillin,
D(—)-α-[(3-methylaminocarbonyl-5-methyl-imidazolidin-2-on-1-yl)-carbonylamino]-benzylpenicillin,
D(—)-α-[(3-methylaminocarbonyl-1,3-diaza-cyclohexan-2-on-1-yl)-carbonylamino]-benzylpenicillin,
D(—)-α-[(3-i-propyloxycarbonyl-4-methyl-imidazolidin-2-on-1-yl)-carbonylamino]-benzylpenicillin,
D(—)-α-[(3-i-propyloxycarbonyl-5-methyl-imidazolidin-2-on-1-yl)-carbonylamino]-benzylpenicillin,
D(—)-α-[(3-i-propyloxycarbonyl-1,3-diaza-cyclohexan-2-on-1-yl)-carbonylamino]-benzylpenicillin,
D(—)-α-[(3-methylsulphonyl-4,5-dimethyl-imidazolidin-2-on-1-yl)-carbonylamino]-benzylpenicillin,
D(—)-α-[(3-methylsulphonyl-4,4-dimethyl-imidazolidin-2-on-1-yl)-carbonylamino]-benzylpenicillin,
D(—)-α-[(3-methylsulphonyl-5,5-dimethyl-imidazolidin-2-on-1-yl)-carbonylamino]-benzylpenicillin,
D(—)-α-[(3-formyl-4,5-dimethyl-imidazolidin-2-on-1-yl)-carbonylamino]-benzylpenicillin,
D(—)-α-[(3-formyl-4,4-dimethyl-imidazolidin-2-on-1-yl)-carbonylamino]-benzylpenicillin,
D(—)-α-[(3-formyl-5,5-dimethyl-imidazolidin-2-on-1-yl)-carbonylamino]-benzylpenicillin,
D(—)-α-[(3-methylcarbonyl-4-methyl-imidazolidin-2-on-1-yl)-carbonylamino]-benzylpenicillin,
D(—)-α-[(3-methylcarbonyl-5-methyl-imidazolidin-2-on-1-yl)-carbonylamino]-benzylpenicillin or
D(—)-α-[(3-methylcarbonyl-1,3-diaza-cyclohexan-2-on-1-yl)-carbonylamino]-benzylpenicillin.

EXAMPLE 56

A. Sodium D,L-α-[(3-methylsulphonyl-imidazolidin-2-on-1-yl)-carbonylamino]-4-methyl-benzylpenicillin:

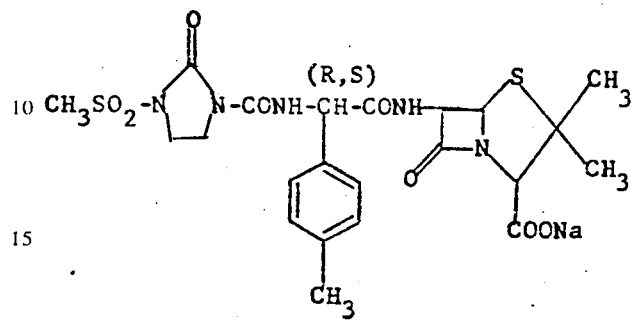

This penicillin was produced as described in Example 39A from 7.0 parts by weight of D,L-α-[(3-methylsulphonyl-imidazolidin-2-on-1-yl)-carbonylamino]-4-methylphenylacetic acid, 3.8 parts by weight of tetramethylchloroformamidinium chloride and 5.0 parts by weight of 6-aminopenicillanic acid.

Yield: 57%

β-Lactam content: 83%

IR-bands at 3320, 1765, 1727, 1674, 1605, 1515, 1255 and 1170 cm$^{-1}$ (in Nujol).

NMR-signals at $\tau$ = 2.65 (2H), 2.83 (2H), 4.3–4.6 (3H), 5.8 (1H), 6.15 (4H), 6.7 (3H), 7.7 (3H) and 8.3–8.6 ppm (6H).

B. D,L-α-[(3-methylsulphonyl-imidazolidin-2-on-1-yl)-carbonylamino]-4-methyl-phenylacetic acid:

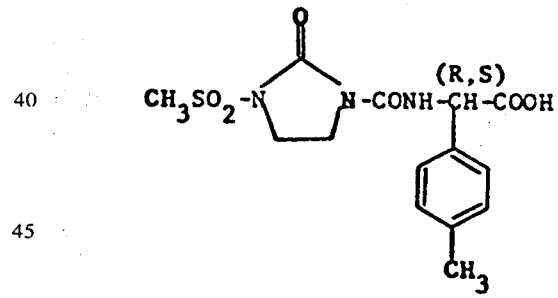

This carboxylic acid was produced as described in Example 39B.1 from 11.3 parts by weight of 1-chlorocarbonyl-3-methylsulphonyl-imidazolid-2-one and 9.1 parts by weight of D,L-α-4-(methylphenyl)-glycine.

Yield: 42%

IR-bands at 3700–2200, 3300, 1740–1660, 1540–1500, 1255 and 970 cm$^{-1}$ (in Nujol). NMR-signals at $\tau$ = 1.3 (1H), 2.7 (4H), 4.7 (1H), 6.2 (4H), 6.6 (3H) and 7.7 ppm (3H).

EXAMPLE 57

A. Sodium D,L-α-[(3-methoxycarbonyl-imidazolidin-2-on-1-yl)-carbonylamino]-4-chlorobenzylpenicillin:

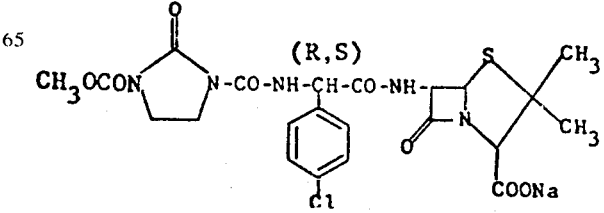

This penicillin was produced as described in Example 39A from 9 parts by weight of D,L-α-[(3-methoxycarbonyl-imidazolidin-2-on-1-yl)-carbonylamino]-4-chloro-phenylacetic acid, 4.85 parts by weight of tetramethylchloroformamidinium chloride and 6.5 parts by weight of 6-aminopenicillanic acid.

Yield: 80%
β-Lactam content: 85%
IR-bands at 3300, 3050, 1770, 1742, 1730, 1670, 1605, 1520, 1320 and 1260 cm⁻¹ (in Nujol).
NMR-signals at τ = 2.57 (2H), 2.65 (2H), 4.35–4.65 (3H), 6.14 (4H), 6.16 (3H) and 8.3–8.6 ppm (6H).

B.

D,L-α-[(3-methoxycarbonyl-imidazolidin-2-on-1-yl)-carbonylamino]-4-chloro-phenylacetic acid:

This carboxylic acid was produced as described in Example 39B.1 from 10.4 parts by weight of 1-chlorocarbonyl-3-methoxycarbonyl-imidazolid-2-one and 10.2 parts by weight of D,L-α-(4-chlorophenyl)-glycine.

Yield: 61%
Calculated: C, 47.2; H, 4.0; Cl, 10.0; N, 11.8.
Found: C, 47.4; H, 4.5; Cl, 9.2; N, 11.2.
IR-bands at 3700–2250, 3280, 3060 and 1780–1630 cm⁻¹ (in Nujol).
NMR-signals at τ = 1.0 (1H), 2.5 (4H), 4.5 (1H), 6.15 (4H) and 6.20 ppm (3H).

C.

1-Chlorocarbonyl-3-methoxycarbonyl-imidazolid-2-one

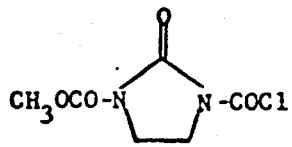

This carbamic acid chloride was produced as described in Example 45B from 8 parts by weight of N-methoxycarbonyl-imidazolid-2-one, 9.7 parts by weight of trimethylchlorosilane, 9 parts by weight of triethylamine and 6.2 parts by weight of phosgene.

Yield: 72%
Melting point = 129° C
Calculated: C, 34.8; H, 3.4; Cl, 17.2; N, 13.6.
Found: C, 34.8; H, 3.4; Cl, 17.1; N, 13.6.
IR-bands at 1820, 1737, 1690 and 1260 cm⁻¹.
NMR-signals at τ = 5.7–6.3 (4H) and 6.1 ppm (3H).

D. N-methoxycarbonyl-imidazolid-2-one

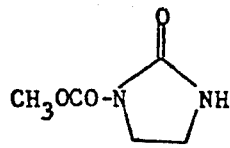

14.9 parts by weight of N-chlorocarbonyl-imidazolid-2-one were introduced into 70 parts by volume of ice-cold methanol and the mixture was stirred for 1 hour at room temperature and subsequently for 1 hour at 40°–50° C. After stripping off the excess methanol, the product was recrystallized from acetone.

Yield: 55%
Melting point = 185° C.
Calculated: C, 41.6; H, 5.5; N, 19.4.
Found: C, 41.8; H, 4.8; N, 19.2.
IR-bands at 3320, 1745, and 1670 cm⁻¹.

EXAMPLE 58

A. Sodium
D,L-α-[(3-methoxycarbonyl-imidazolidin-2-on-1-yl)-carbonylamino]-α-thienyl(2)-methylpenicillin:

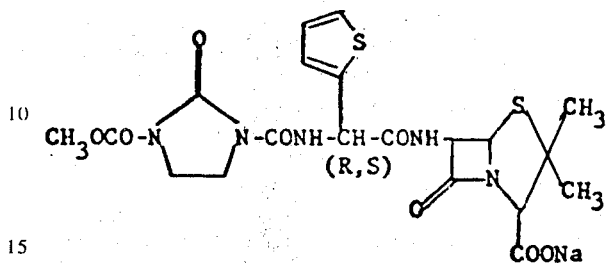

This penicillin was produced as described in Example 39A from 8.5 parts by weight of D,L-α-[(3-methoxycarbonyl-imidazolidin-2-on-1-yl)-carbonylamino]-α-thienyl(2)-acetic acid, 5.1 parts by weight of tetramethylchloroformamidinium chloride and 6.9 parts by weight of 6-aminopenicillanic acid.

Yield: 72%
β-Lactam content: 67%
IR-bands at 3310, 1773, 1750, 1730, 1670, 1610, 1520, 1320 and 1265 cm⁻¹ (in Nujol).
NMR-signals at = 2.5–3.2 (3H), 4.1 (1H), 4.4–4.6 (2H), 5.8 (1H), 6.15 (7H) and 8.3–8.55 ppm (6H).

According to the NMR-spectrum, the crude product still contained 23% of D,L-α-[(3-methoxycarbonyl-imidazolidin-2-on-1-yl)-carbonylamino]-α-thienyl(2)-acetic acid, which is however removable by fractional acidification of the aqueous solution.

B.
D,L-α-[(3-methoxycarbonyl-imidazolidin-2-on-1-yl)-carbonylamino]-α-thienyl(2)-acetic acid:

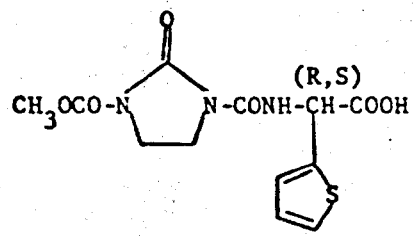

This carboxylic acid was produced as described in Example 39B.1 from 8.8 parts by weight of 1-chlorocarbonyl-3-methoxycarbonyl-imidazolid-2-one and 7.3 parts by weight of D,L-α-thienyl(2)-glycine.

Yield: 73%
Calculated: C, 44.0; H, 4.0; N, 12.8; S, 9.8.
Found: C, 44.1; H, 4.0; N, 12.0; S, 9.9.
IR-bands at 3700–2200, 3280, 1775, 1740–1640, 1515 and 1015 cm⁻¹ (in Nujol).
NMR-signals at τ = 0.9 (1H), 2.5–3.1 (3H), 4.2 (1H), 6.15 (4H) and 6.20 ppm (3H).

EXAMPLE 59

Sodium
D(−)-α-[(3-ethylsulphonyl-imidazolidin-2-on-1-yl)-carbonylamino]-benzylpenicillin:

2.9 parts by weight of D(−)-α-[(3-ethylsulphonylimidazolidin-2-on-1-yl)-carbonylamino]-phenylacetic acid were dissolved in 30 parts by volume of tetrahydrofurane, the solution was cooled to −30° C and a solution of 1.0 part by weight of tetramethylchloroformamidinium chloride in 30 parts by volume of dichloromethane, pre-cooled to −30° C, was then added at once. Hereupon, some material precipitated. After the temperature had been allowed to rise to −25° C to −20° C, a clear solution formed. This solution was left to stand for 15 minutes at −25° C. Then this solution was added all at once to a solution or suspension, maintained at 0° C to 5° C, of 2.3 parts by weight of 6-aminopenicillanic acid in 25 parts by volume of 90% strength aqueous tetrahydrofurane which had been adjusted to pH 2.5 by adding 10% strength aqueous hydrochloric acid. Thereafter, the pH was kept at 2.5 by appropriate addition of 2 N aqueous sodium hydroxide solution and the mixture was cooled with an ice-water mixture, as a result of which the temperature was brought to 0° C, and kept there. After one hour the mixture was worked up, though in order to maintain the pH of 2.5 it was still necessary to add sodium hydroxide solution, if only a little. Working up took place as described in Example 49.

Yield: 2.3 parts by weight

The IR-spectrum of this penicillin was identical to that of the penicillin of Example 49.

What is claimed is:

1. A compound selected from the group consisting of a penicillin of the formula

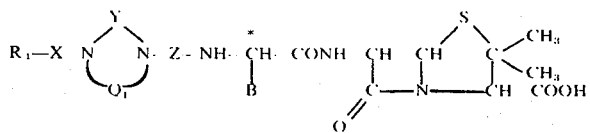

wherein the carbon atoms designated by * constitutes a center of chirality;

X is —CO—, —CS— or —SO$_2$—;

each of Y and Z, independently of the other, is —CO— or —CS—;

B is thienyl, cyclohexenyl, cyclohexa-1,4-dien-1-yl, phenyl or phenyl substituted by one or two members selected from the group consisting of halo, nitro, hydroxy, methoxy, methylthio and alkyl of 1 to 5 carbon atoms;

Q$_1$ is ethylene or trimethylene unsubstituted or substituted by one or two methyl groups; and R$_1$ is alkyl of 1 to 10 carbon atoms; and the pharmaceutically acceptable salts thereof.

2. A compound according to claim 1 which is of an alkali metal salt.

3. A compound according to claim 1 which is the sodium salt.

4. A compound according to claim 1 wherein Y is —CO—.

5. A compound according to claim 1 wherein B is thienyl, cyclohexenyl, cyclohexa-1,4-dien-1-yl, phenyl, halophenyl, hydroxyphenyl, nitrophenyl, methoxyphenyl, methylphenyl, or methylthiophenyl.

6. A compound according to claim 1 wherein each of Z and Y is —CO—;

B is thienyl, cyclohexenyl, cyclohexa-1,4-dien-1-yl, phenyl, halophenyl or hydroxyphenyl; and Q$_1$ is ethylene or trimethylene, unsubstituted or substituted by one or two methyl groups.

7. A compound according to claim 1 wherein Q$_1$ is ethylene.

8. A compound according to claim 1 wherein X is —SO$_2$— and R$_1$ is alkyl of 1 to 4 carbon atoms.

9. A compound according to claim 1 wherein each of X and Y is —CO—;

X is CO;

B is phenyl; and

Q$_1$ is ethylene, 1,2-propylene or trimethylene.

10. A compound according to claim 1 wherein the configuration about the carbon atom designated * is R.

11. A compound according to claim 1 wherein the configuration about the carbon atom designated * is S.

12. The compound according to claim 1 which is α-(3-methylsulphonylimidazolidin-2-on-1-ylcarbonylamino)benzylpenicillin.

13. The compound according to claim 1 which is D(−)-α-[(3-acetyl-imidazolidin-2-on-1-yl)-carbonylamino]-benzylpenicillin, or the sodium salt thereof.

14. The compound according to claim 1 which is D(−)-α-[(3-methylsulphonyl-imidazolidin-2-on-1-yl)-carbonylamino]-benzylpenicillin, or the sodium salt thereof.

15. The compound according to claim 1 which is D(−)-α-[(3-n-butyryl-imidazolidin-2-on-1-yl)-carbonylamino]-benzylpenicillin, or the sodium salt thereof.

16. The compound according to claim 1 which is α-[(3-acetyl-imidazolidin-2-on-1-yl)-carbonylamino]-p-methylbenzylpenicillin, or the sodium salt thereof.

17. The compound according to claim 1 which is α-[(3-acetyl-imidazolidin-2-on-1-yl)-carbonylamino]-p-methoxybenzylpenicillin, or the sodium salt thereof.

18. The compound according to claim 1 which is α-[(3-acetyl-imidazolidin-2-on-1-yl)-carbonylamino]-p-methylthiobenzylpenicillin, or the sodium salt thereof.

19. The compound according to claim 1 which is α-[(3-acetyl-imidazolidin-2-on-1-yl)-carbonylamino]-p-hydroxybenzylpenicillin, or the sodium salt thereof.

20. The compound according to claim 1 which is α-[(3-acetyl-imidazolidin-2-on-1-yl)-carbonylamino]-p-chlorobenzylpenicillin, or the sodium salt thereof.

21. The compound according to claim 1 which is α-[(3-acetyl-imidazolidin-2-on-1-yl)-carbonylamino]-p-nitrobenzylpenicillin, or the sodium salt thereof.

22. The compound according to claim 1 which is α-[(3-acetyl-imidazolidin-2-on-1-yl)-carbonylamino]-α-thienyl-(2)-methylpenicillin, or the sodium salt thereof.

23. The compound according to claim 1 which is α-[(3-acetyl-imidazolidin-2-on-1-yl)-carbonylamino]-α-thienyl-(3)-methylpenicillin, or the sodium salt thereof.

24. The compound according to claim 1 which is α-[(3-methylsulphonyl-imidazolidin-2-on-1-yl)-carbonylamino]-p-methylbenzylpenicillin, or the sodium salt thereof.

25. The compound according to claim 1 which is α-[(3-methylsulphonyl-imidazolidin-2-on-1-yl)-carbonylamino]-p-methoxybenzylpenicillin, or the sodium salt thereof.

26. The compound according to claim 1 which is α-[(3-methylsulphonyl-imidazolidin-2-on-1-yl)-carbonylamino]-p-methylthiobenzylpenicillin, or the sodium salt thereof.

27. The compound according to claim 1 which is α-[(3-methylsulphonyl-imidazolidin-2-on-1-yl)-carbonylamino]-p-hydroxybenzylpenicillin, or the sodium salt thereof.

28. The compound according to claim 1 which is α-[(3-methylsulphonyl-imidazolidin-2-on-1-yl)-carbonylamino]-p-chlorobenzylpenicillin, or the sodium salt thereof.

29. The compound according to claim 1 which is α-[(3-methylsulphonyl-imidazolidin-2-on-1-yl)-carbonylamino]-p-nitrobenzylpenicillin, or the sodium salt thereof.

30. The compound according to claim 1 which is α-[(3-methylsulphonyl-imidazolidin-2-on-1-yl)-carbonylamino]-α-thienyl(2)-methylpenicillin, or the sodium salt thereof.

31. The compound according to claim 1 which is α-[(3-methylsulphonyl-imidazolidin-2-on-1-yl)-carbonylamino]-α-thienyl(3)-methylpenicillin, or the sodium salt thereof.

32. The compound according to claim 1 which is α-[(3-ethylsulphonyl-imidazolidin-2-on-1-yl)-carbonylamino]-p-methylbenzylpenicillin, or the sodium salt thereof.

33. The compound according to claim 1 which is α-[(3-ethylsulphonyl-imidazolidin-2-on-1-yl)-carbonylamino]-p-methoxybenzylpenicillin, or the sodium salt thereof.

34. The compound according to claim 1 which is α-[(3-ethylsulphonyl-imidazolidin-2-on-1-yl)-carbonylamino]-p-methylthiobenzylpenicillin, or the sodium salt thereof.

35. The compound according to claim 1 which is α-[(3-ethylsulphonyl-imidazolidin-2-on-1-yl)-carbonylamino]-p-hydroxybenzylpenicillin, or the sodium salt thereof.

36. The compound according to claim 1 which is α-[(3-ethylsulphonyl-imidazolidin-2-on-1-yl)-carbonylamino]-p-chlorobenzylpenicillin, or the sodium salt thereof.

37. The compound according to claim 1 which is α-[(3-ethylsulphonyl-imidazolidin-2-on-1-yl)-carbonylamino]-p-nitrobenzylpenicillin, or the sodium salt thereof.

38. The compound according to claim 1 which is α-[(3-ethylsulphonyl-imidazolidin-2-on-1-yl)-carbonylamino]-α-thienyl(2)-methylpenicillin, or the sodium salt thereof.

39. The compound according to claim 1 which is α-[(3-ethylsulphonyl-imidazolidin-2-on-1-yl)-carbonylamino]-α-thienyl(3)-methylpenicillin, or the sodium salt thereof.

40. The compound according to claim 1 which is D(−)-α-[(3-methylsulphonyl-4-methyl-imidazolidin-2-on-1-yl)-carbonylamino]-benzylpenicillin, or the sodium salt thereof.

41. The compound according to claim 1 which is D(−)-α-[(3-methylsulphonyl-5-methyl-imidazolidin-2-on-1-yl)-carbonylamino]-benzylpenicillin, or the sodium salt thereof.

42. The compound according to claim 1 which is D(−)-α-[(3-propionyl-imidazolidin-2-on-1-yl)-carbonylamino]-benzylpenicillin, or the sodium salt thereof.

43. The compound according to claim 1 which is D(−)-α-[(3-acetyl-4-methyl-imidazolidin-2-on-1-yl)-carbonylamino]-benzylpenicillin, or the sodium salt thereof.

44. The compound according to claim 1 which is D(−)-α-[(3-acetyl-5-methyl-imidazolidin-2-on-1-yl)-carbonylamino]-benzylpenicillin, or the sodium salt thereof.

45. The compound according to claim 1 which is D(−)-α-[(3-acetyl-1,3-diaza-cyclohexan-2-on-1-yl)-carbonylamino]-benzylpenicillin, or the sodium salt thereof.

46. The compound according to claim 1 which is D(−)-α-[(3-n-propylsulphonyl-imidazolidin-2-on-1-yl)-carbonylamino]-benzylpenicillin, or the sodium salt thereof.

47. The compound according to claim 1 which is D(−)-α-[(3-ethylsulphonyl-4-methyl-imidazolidin-2-on-1-yl)-carbonylamino]-benzylpenicillin, or the sodium salt thereof.

48. The compound according to claim 1 which is D(−)-α-[(3-ethylsulphonyl-5-methyl-imidazolidin-2-on-1-yl)-carbonylamino]-benzylpenicillin, or the sodium salt thereof.

49. The compound according to claim 1 which is D(−)-α-[(3-ethylsulphonyl-1,3-diaza-cyclohexan-2-on-1-yl)-carbonylamino]-benzylpenicillin, or the sodium salt thereof.

50. The compound according to claim 1 which is D(−)-α-[(3-methylsulphonyl-1,3-diaza-cyclohexan-2-on-1-yl)-carbonylamino]-benzylpenicillin, or the sodium salt thereof.

51. The compound according to claim 1 which is D(−)-α-[(3-n-propylsulonyl-1,3-diaza-cyclohexan-2-on-1-yl)-carbonylamino]-benzylpenicillin, or the sodium salt thereof.

52. The compound according to claim 1 which is D(−)-α-[(3-i-propylsulphonyl-1,3-diaza-cyclohexan-2-on-1-yl)-carbonylamino]-benzylpenicillin, or the sodium salt thereof.

53. The compound according to claim 1 which is D(−)-α-[(3-i-propylsulphonyl-imidazolidin-2-on-1-yl)-carbonylamino]-benzylpenicillin, or the sodium salt thereof.

54. The compound according to claim 1 which is D(−)-α-[(3-i-propylsulphonyl-4-methyl-imidazolidin-2-on-1-yl)-carbonylamino]-benzylpenicillin, or the sodium salt thereof.

55. The compound according to claim 1 which is D(−)-α-[(3-i-propylsulphonyl-5-methyl-imidazolidin-2-on-1-yl)-carbonylamino]-benzylpenicillin, or the sodium salt thereof.

56. The compound according to claim 1 which is D(−)-α-[(3-n-propylsulphonyl-4-methyl-imidazolidin-2-on-1-yl)-carbonylamino]-benzylpenicillin, or the sodium salt thereof.

57. The compound according to claim 1 which is D(−)-α-[(3-n-propylsulphonyl-5-methyl-imidazolidin-2-on-1-yl)-carbonylamino]-benzylpenicillin, or the sodium salt thereof.

58. The compound according to claim 1 which is D(−)-α-[(3-methylsulphonyl-4,5-dimethyl-imidazolidin-2-on-1-yl)-carbonylamino]-benzylpenicillin, or the sodium salt thereof.

59. The compound according to claim 1 which is D(−)-α-[(3-methylsulphonyl-4,4-dimethyl-imidazolidin-2-on-1-yl)-carbonylamino]-benzylpenicillin, or the sodium salt thereof.

60. The compound according to claim 1 which is D(−)-α-[(3-methylsulphonyl-5,5-dimethyl-imidazolidin-2-on-1-yl)-carbonylamino]-benzylpenicillin, or the sodium salt thereof.

61. The compound according to claim 1 which is D(−)-α-[(3-pivaloyl-imidazolidin-2-on-1-yl)-carbonylamino]-benzylpenicillin, or the sodium salt thereof.

62. The compound according to claim 1 which is D(−)-α-[(3-methylsulphonyl-imidazolidin-2-on-1-ylcarbonylamino]-1,4-cyclohexadien-yl-1-methylpenicillin, or the sodium salt thereof.

63. The compound according to claim 1 which is L(+)-α-[(3-methylsulphonyl-imidazolidin-2-on-1-yl)-carbonylamino]-benzylpenicillin, or the sodium salt thereof.

64. The compound according to claim 1 which is α-[(3-methylsulphonyl-imidazolidin-2-on-1-yl)-carbonylamino]-2,6-dichloro-benzylpenicillin or the sodium salt thereof.

65. The compound according to claim 1 which is L(+)-α-[(3-acetyl-imidazolidin-2-on-1-yl)-carbonylamino]-benzylpenicillin, or the sodium salt thereof.

66. The compound according to claim 1 which is α-[(3-acetyl-imidazolidin-2-on-1-yl)-carbonylamino]-2,6-dichloro-benzylpenicillin, or the sodium salt thereof.

67. The compound according to claim 1 which is D(−)-α-[(3-ethylsulphonyl-imidazolidin-2-on-1-yl)-carbonylamino]-benzylpenicillin, or the sodium salt thereof.

68. The compound according to claim 1 which is D(−)-α-[(3-methylsulphonyl-imidazolidin-2-on-1-yl)-carbonylamino]-4-chloro-benzylpenicillin, or the sodium salt thereof.

69. The compound according to claim 1 which is D(−)-α-[(3-methylsulphonyl-imidazolidin-2-on-1-yl)-carbonylamino]-4-methyl-benzylpenicillin, or the sodium salt thereof.

70. The compound according to claim 1 which is D(−)-α-[(3-methylsulphonyl-imidazolidin-2-on-1-yl)-carbonylamino]-4-benzylpenicillin, or the sodium salt thereof.

71. The compound according to claim 1 which is D(−)-α-[(3-methylsulphonyl-imidazolidin-2-on-1-yl)-carbonylamino]-4-benzylpenicillin, or the sodium salt thereof.

72. The compound according to claim 1 which is D(−)-α-[(3-methylsulphonyl-imidazolidin-2-on-1-yl)-carbonylamino]-α-thienyl-(2)-methylpenicillin, or the sodium salt thereof.

73. The compound according to claim 1 which is α-[(3-methylsulphonyl-imidazolidin-2-on-1-yl)-carbonylamino]-4-methylsulphonyl-benzylpenicillin, or the sodium salt thereof.

74. The compound according to claim 1 which is D(−)-α-[(3-ethylsulphonyl-imidazolidin-2-on-1-yl)-carbonylamino]-4-chloro-benzylpenicillin, or the sodium salt thereof.

75. The compound according to claim 1 which D(−)-α-[(3-ethylsulphonyl-imidazolidin-2-on-1-yl)-carbonylamino]-4-methyl-benzylpenicillin, or the sodium salt thereof.

76. The compound according to claim 1 which is D(−)-α-[(3-ethylsulphonyl-imidazolidin-2-on-1-yl)-carbonylamino]-4-nitro-benzylpenicillin, or the sodium salt thereof.

77. The compound according to claim 1 which is D(−)-α-[(3-ethylsulphonyl-imidazolidin-2-on-1-yl)-carbonylamino]-4-hydroxy-benzylpenicillin, or the sodium salt thereof.

78. The compound according to claim 1 which is D(−)-α-[(3-ethylsulphonyl-imidazolidin-2-on-1-yl)-carbonylamino]-α-thienyl-(2)-methylpenicillin, or the sodium salt thereof.

79. The compound according to claim 1 which is α-[(3-ethylsulphonyl-imidazolidin-2-on-1-yl)-carbonylamino]-4-methylsulphonyl-benzylpenicillin, or the sodium salt thereof.

80. The compound according to claim 1 which is D(−)-α-[(3-acetyl-imidazolidin-2-on-1-yl)-carbonylamino]-4-chloro-benzylpenicillin, or the sodium salt thereof.

81. The compound according to claim 1 which is D(−)-α-[(3-acetyl-imidazolidin-2-on-1-yl)-carbonylamino]-4-methyl-benzylpenicillin, or the sodium salt thereof.

82. The compound according to claim 1 which is D(−)-α-[(3-acetyl-imidazolidin-2-on-1-yl)-carbonylamino]-4-nitro-benzylpenicillin, or the sodium salt thereof.

83. The compound according to claim 1 which is D(−)-α-[(3-acetyl-imidazolidin-2-on-1-yl)-carbonylamino]-4-hydroxy-benzylpenicillin, or the sodium salt thereof.

84. The compound according to claim 1 which is D(−)-α-[(3-acetyl-imidazolidin-2-on-1-yl)-carbonylamino]-α-thienyl-(2)-methylpenicillin, or the sodium salt thereof.

85. The compound according to claim 1 which is α-[(3-acetyl-imidazolidin-2-on-1-yl)-carbonylamino]-4-methylsulphonyl-benzylpenicillin, or the sodium salt thereof.

* * * * *